US010791692B2

(12) United States Patent
Tang et al.

(10) Patent No.: US 10,791,692 B2
(45) Date of Patent: Oct. 6, 2020

(54) FINE MAPPING AND VALIDATION OF QTL UNDERLYING FIBER CONTENT AND IDENTIFICATION OF SNP MARKERS FOR MARKER ASSISTED SELECTION

(71) Applicant: Dow AgroSciences LLC, Indianapolis, IN (US)

(72) Inventors: Shunxue Tang, Carmel, IN (US); Van L. Ripley, Saskatchewan (CA); Thomas G. Patterson, Indianapolis, IN (US); Michelle Wiggins, Indianapolis, IN (US); Joshua A. Flook, Indianapolis, IN (US); Cherie Ochsenfeld, Indianapolis, IN (US); Daniel Garcia, Indianapolis, IN (US); Syed Masood Rizvi, Saskatchewan (CA); Muhammad Tahir, Saskatchewan (CA); Ryan Preuss, Indianapolis, IN (US); Donna Carolynn Knievel, Saskatchewan (CA); Steve Rounsley, Indianapolis, IN (US); Zoe Christina Ehlert, Saskatchewan (CA)

(73) Assignee: Dow AgroSciences LLC, Indianapolis, IN (US)

( * ) Notice: Subject to any disclaimer, the term of this patent is extended or adjusted under 35 U.S.C. 154(b) by 159 days.

(21) Appl. No.: 15/731,561

(22) PCT Filed: Dec. 18, 2015

(86) PCT No.: PCT/US2015/066813
§ 371 (c)(1),
(2) Date: Jun. 27, 2017

(87) PCT Pub. No.: WO2016/100883
PCT Pub. Date: Jun. 23, 2016

(65) Prior Publication Data
US 2017/0332593 A1 Nov. 23, 2017

Related U.S. Application Data

(60) Provisional application No. 62/093,963, filed on Dec. 18, 2014.

(51) Int. Cl.
A01H 5/10 (2018.01)
C12Q 1/68 (2018.01)
C12Q 1/6895 (2018.01)
A01H 1/04 (2006.01)
A23L 19/00 (2016.01)

(52) U.S. Cl.
CPC .............. A01H 5/10 (2013.01); A01H 1/04 (2013.01); C12Q 1/6895 (2013.01); A23L 19/00 (2016.08); C12Q 2600/13 (2013.01); C12Q 2600/158 (2013.01)

(58) Field of Classification Search
None
See application file for complete search history.

(56) References Cited

U.S. PATENT DOCUMENTS

2010/0303999 A1* 12/2010 Chungu .................. A01H 5/10
426/630
2014/0220564 A1 8/2014 Zhang et al.

FOREIGN PATENT DOCUMENTS

WO 2016100883 6/2016

OTHER PUBLICATIONS

Badani et al., 2006, Colocalization of a partially dominant gene for yellow seed colour with a major QTL influencing acid detergent fibre (ADF) content in different crosses of oilseed rape (Brassica napus), Genome 49: 1499-1509.*
Predicted Brassica rapa 2-isopropylmalate synthase 1, chloroplastic-like (LOC103842698) sequence, NCBI/GenBank accession No. XM_009119363, published on Oct. 13, 2016.*
Predicted Brassica rapa post-GPI attachment to proteins factor 3-like (LOC103842843), transcript variant X1 sequence, NCBI/GenBank accession No. XM_009119508, published on Oct. 13, 2016.*
Badani et al., "Colocalization of a partially dominant gene for yellow seed color with a major QTL influencing acid detergent fibre (ADF) content in different crosses of oilseed rape (Brassica napus)," Genome, 2006, pp. 1499-1509, vol. 49.
International Search Report and Written Opinion for PCT/US2015/066813, dated Apr. 11, 2016.
Liu et al., "A high-density SNP map for accurate mapping of seed fibre QTL in Brassica napus L," PLoS One, 2013, pp. 1-9, vol. 8, Issue 12.
Nesi et al., "Genetic and molecular approaches to improve nutritional value of Brassica napus L seed," Comptes Rendus Biologies, 2008, pp. 763-771, vol. 331.
Yan et al., 'Co-location of seed oil content, seed hull content and seed coat color QTL in three different environments in Brassica napus L., Euphytica, 2009, pp. 355-364, vol. 170.

(Continued)

Primary Examiner — Bratislav Stankovic

(57) ABSTRACT

A method for identifying a quantitative trait locus associated with desirable nutritional traits in canola includes: analyzing a population of canola plants or germplasm for desirable nutritional traits; determining the genotype of the canola plants or germplasm using at least one marker selected from the group consisting of SEQ ID NO:1 through SEQ ID NO:111; mapping the canola plants or germplasm for the presence of a quantitative trait locus (QTL) associated with the markers; and associating the QTL with the desirable nutritional trait. An isolated and/or recombinant nucleic acid includes a sequence associated with a quantitative trait locus (QTL), wherein the QTL is associated with a desirable nutritional trait in a canola plant or germplasm and wherein the QTL is further associated with at least one marker selected from the group consisting of SEQ ID NO:1 through SEQ ID NO:111.

12 Claims, 8 Drawing Sheets
Specification includes a Sequence Listing.

(56) References Cited

OTHER PUBLICATIONS

"Infinium Assay Workflow," Illumina, <http://www.bea.ki.se/documents/workflow_infinium.pdf>, Oct. 11, 2012, 2 pages.

Akhov, Leonid, et al., "Proanthycyanidin biosynthesis in the seed coat of yellow-seeded, canola quality *brassica napus* YN001-29 is constrained at the committed step catalyzed by dihydroflavonon 4-reductase," Botany + Botanique, Jun. 2009, pp. 616-625, vol. 87, No. 6.

Relf-Eckstein, et al., Meal quality improvement in *Brassica napus* canola through the development of low fibre yellow-seeded) germplasm; Feed and Industrial Raw Material: pp. 289-291 (2007).

\* cited by examiner

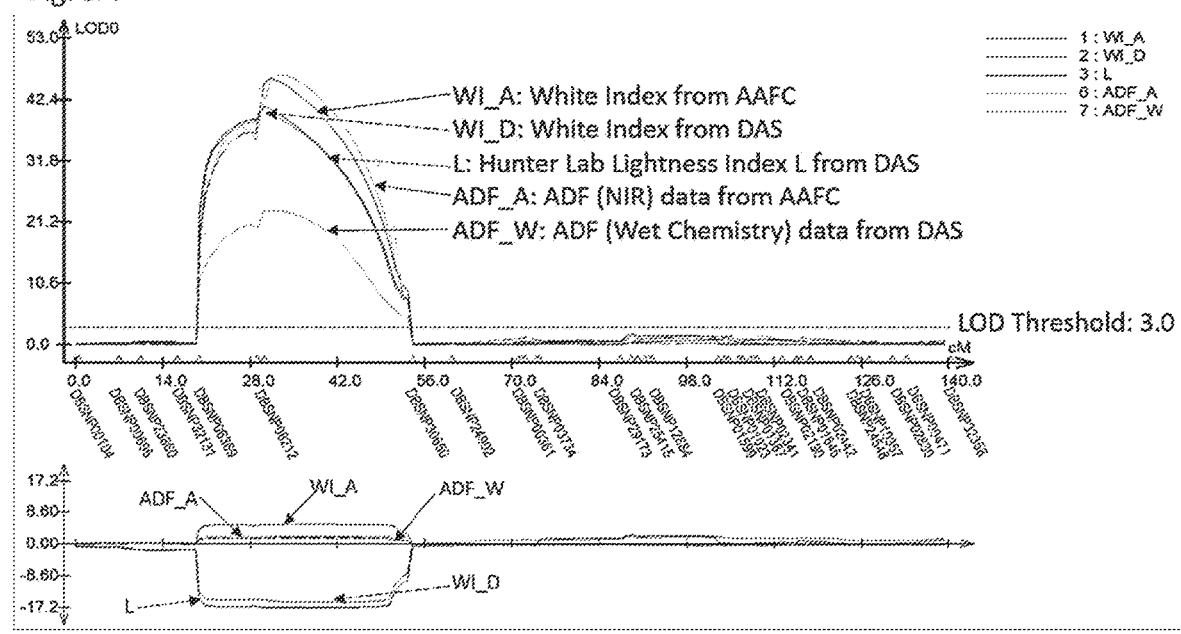

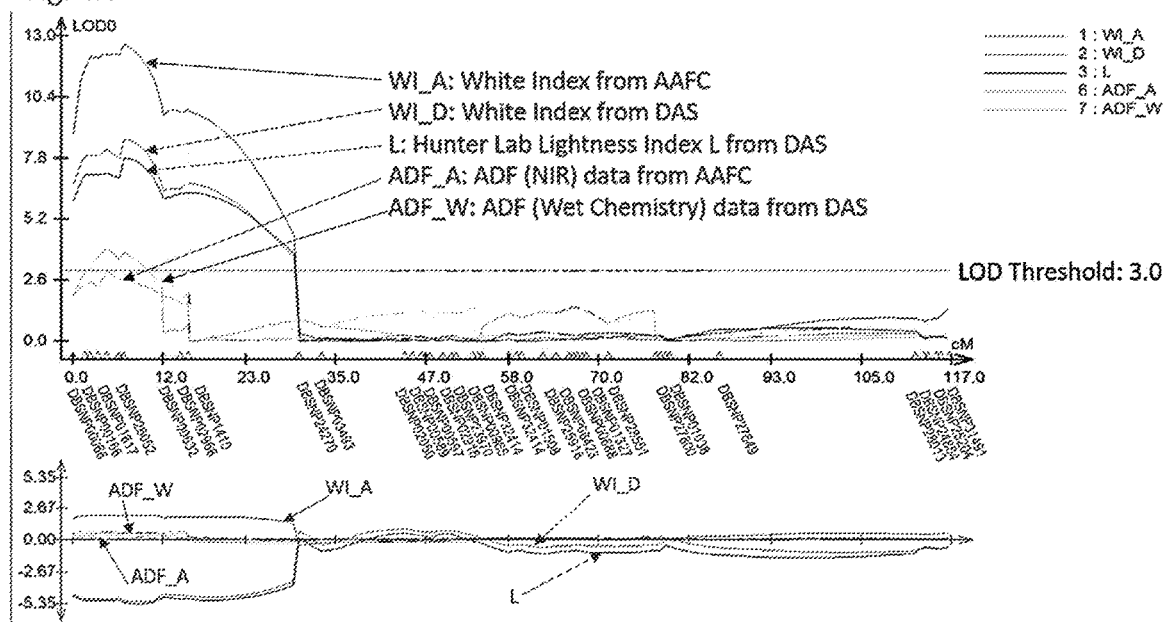

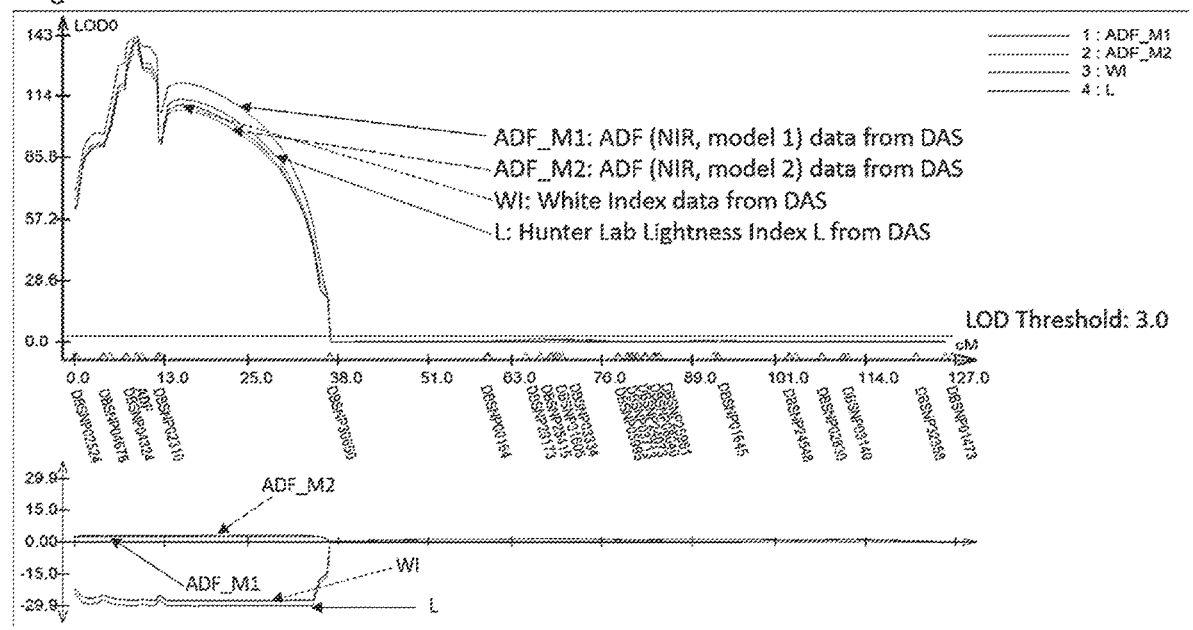

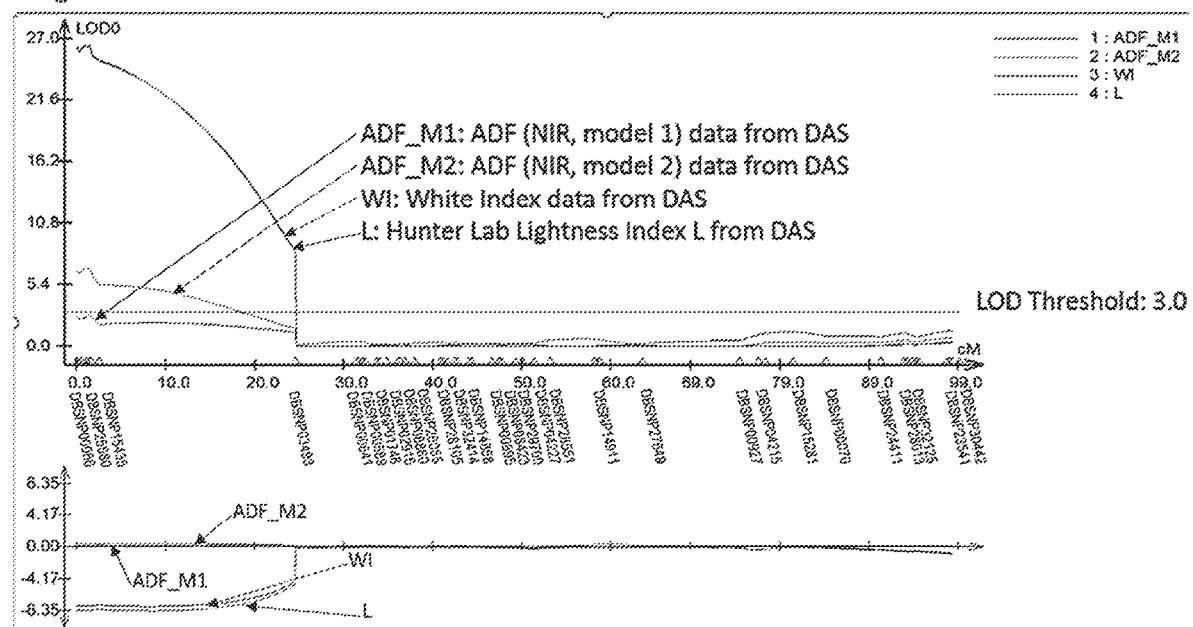

```
                    DBSNP01120 DBSNP357202 DBSNP357203
117.4    DBSNP222203 DBSNP357208
117.7    DBSNP357214 DBSNP222206
118.2    DBSNP357215 DBSNP357216 DBSNP357217 QTL_ADF_N9
         QTL_WI_N9 DBSNP357218
118.7    DBSNP357219
119.0    DBSNP357221 DBSNP357222 DBSNP357223 DBSNP357224
         DBSNP222208 DBSNP357226 DBSNP357227 DBSNP357228
119.3    DBSNP357229
         DBSNP357230 DBSNP357231 DBSNP357232 DBSNP357233
         DBSNP357234 DBSNP357235 DBSNP357236 DBSNP357237
         DBSNP357238 DBSNP357239 DBSNP357240 DBSNP357241
         DBSNP357242 DBSNP357244 DBSNP357245 DBSNP357246
         DBSNP357247 DBSNP04324 DBSNP357249 DBSNP357250
         DBSNP357251 DBSNP357252 DBSNP357253 DBSNP357254
         DBSNP357255 DBSNP357256 DBSNP357257 DBSNP357258
         DBSNP357259 DBSNP357260 DBSNP357262 DBSNP357263
         DBSNP357264 DBSNP357265 DBSNP357266 DBSNP357267
119.8    DBSNP357268 DBSNP357269 DBSNP357270 DBSNP357271
         DBSNP357272 DBSNP357273 DBSNP357274 DBSNP357275
         DBSNP357276 DBSNP357278 DBSNP357280 DBSNP357282
         DBSNP357286 DBSNP222210 DBSNP357287 DBSNP357288
         DBSNP357289 DBSNP357290 DBSNP357291 DBSNP357292
         DBSNP357293 DBSNP357294 DBSNP84508 DBSNP222211
         DBSNP222212 DBSNP222214 DBSNP222219 DBSNP222220
         DBSNP240715 DBSNP222222 DBSNP38295 DBSNP222225
         DBSNP222226 DBSNP08212 DBSNP08214 DBSNP222228
120.1    DBSNP222229 DBSNP42126 DBSNP222231 DBSNP65585
120.6    DBSNP222233 DBSNP222235 DBSNP146598 DBSNP212383
         DBSNP147032 DBSNP94819 DBSNP158066 DBSNP158078
121.4    DBSNP63288 DBSNP52362 DBSNP57623 DBSNP234290
         DBSNP222241 DBSNP222242 DBSNP189108 DBSNP234289
121.7    DBSNP222244
122.0    DBSNP222246
122.3    DBSNP02172
```

FINE MAPPING AND VALIDATION OF QTL UNDERLYING FIBER CONTENT AND IDENTIFICATION OF SNP MARKERS FOR MARKER ASSISTED SELECTION

CROSS-REFERENCE TO RELATED APPLICATIONS

This is a national phase entry under 35 U.S.C. § 371 of international Patent Application PCT/US2015/066813, filed Dec. 18, 2015, published in English as International Patent Publication No. WO2016100883 on Jun. 23, 2016, which claims priority to U.S. Patent Application No. 62/093,963 filed on Dec. 18, 2014, all of which are incorporated in their entirety by reference herein.

TECHNICAL FIELD

The disclosure relates to fine mapping of quantitative trait loci (QTLs) associated with low fiber content and YSC traits and identification of SNP markers for marker assisted selection of these traits in *Brassica napus*.

BACKGROUND

Canola (*Brassica napus* L., 2n=4x=38, AACC), an allotetraploid formed from diploids *B. rapa* (2n=2x=20, AA) and *B. oleracea* (2n=2x=18, CC), is one of the most important vegetable oilseed crops in the world, especially in China, Canada, the European Union and Australia. Canola meal, the fraction of the seed remaining after crushing and oil extraction, is approximately 55% of the volume of canola seed.

Canola meal consists of several components including protein, fiber, residual oil, carbohydrates, and anti-nutritional factors. Canola meal contains approximately 75% of the protein of 48% protein soybean meal, 80% of the energy value, and 300% of the crude fiber, as well as higher levels of anti-nutritional factors such as glucosinolates, tannins, phytic acid, sinapine and erucic acid, and is sold as livestock feed at 60%-70% of the price of soybean meal. See, e.g., Hickling (2007) Canola meal competitive situation and Canola Council of Canada goals, Canola Meal Research Meeting, Saskatoon, Canada; Newkirk (2009) Canola meal feed industry guide (4th Edition). The relatively high fiber content of canola meal is a significant limiting factor for its use in monogastric animal species (Hickling, 2007; Newkirk, 2009). Since meal comprises half of the seed volume of canola, and demand for biodiesel could drive a 67% increase in rapeseed seed production from 2006 to 2015 (Hickling, 2007), there is a need to modify the compositional properties of canola meal and thereby increasing its nutritional value relative to soybean.

Scientists at Agriculture and Agri-Foods Canada (AAFC) have developed yellow seed coat (YSC) lines (YN86-37, YN90-1016, YN97-262 and YN01-429) of low hull proportion with thinner seed coat, low fiber and high oil compared to the black seed coat (BSC) canola (Rakow et al., 2011). Feeding studies, comparing yellow seeded canola meal from AAFC line YN01-429 to *B. juncea*, *B. rapa*, and brown-seeded *B. napus*, demonstrated the advantages of YSC *B. napus* line such as higher protein, lower fiber, increased amino acid digestibility and metabolizable energy content, and improved nutrient and energy utilization based on feed to gain ratio in broiler chickens and monogastric animal species (Hickling, 2009; Slominski et al., 2010).

The breeding of low fiber content has been greatly hampered by a poor understanding of the inheritance and stability of the low fiber content traits, as well as a lack of robust, high-throughput markers tightly linked to the trait. Due to allotetraploidy, effect of multiple genes, maternal effects and environmental effects, the inheritance of low fiber content trait is complex, and identification of markers tightly linked to this trait is very challenging. Somers et al, (2001) reported identification of eight random amplified polymorphic DNA (RAPD) markers for a major gene (pigment1) associated with yellow seed coat trait from YSC line YN90-1016, the low fiber content source of YN97-262 and YN01-429 used in the applicant's Low Fiber breeding program (Rakow et al., 2011). The major gene explained 72.3% of the variation in seed color, while two additional genes that appeared to be additive explained 21.5% of the color variation (Somers et al., 2001).

It has been suggested that the low fiber content of AAFC YSC line YN01-429 and its lineage might be controlled by three recessive genes (Kubik and Thompson, 2009). Current selection of lower fiber canola lines has primarily been based on fiber content data obtained using cost and labor intensive analytical methods, or seed coat color, because of its high correlation with low fiber in the AAFC YSC lines YN97-262 and YN01-429.

SUMMARY OF DISCLOSURE

A particular embodiment of the invention includes a method for identifying quantitative trait locus associated with desirable nutritional traits in canola. The method includes analyzing a population of canola plants or germplasm for desirable nutritional traits. The genotype of the canola plants or germplasm is determined using at least one marker selected from the group consisting of SEQ ID NO:1 through SEQ ID NO:111. The canola plants or germplasm are mapped for the presence of a quantitative trait locus (QTL) associated with the markers. The QTL is associated with the desirable nutritional trait.

Another embodiment relates to an isolated and/or recombinant nucleic acid having a sequence associated with a QTL. The QTL is associated with a desirable nutritional trait in a canola plant or germplasm. The QTL is further associated with at least one marker selected from the group consisting of SEQ ID NO:1 through SEQ ID NO:111.

Yet another embodiment relates to a method for selecting a canola plant or germplasm that comprises desirable nutritional traits. The method includes detecting in the canola plant or germplasm at least one marker linked with a QTL that is selected from the group consisting of SEQ ID NO:1 through SEQ ID NO:111, wherein the QTL is associated with a desirable nutritional trait in the canola plant or germplasm. A canola plant or germplasm is then selected based on the presence of the marker.

The foregoing and other features will become more apparent from the following detailed description of several embodiments, which proceeds with reference to the accompanying figures.

BRIEF DESCRIPTION OF THE DRAWINGS

FIG. 3A shows the location (X-axis) and significance (LOD score on Y-axis) of the QTL identified on N09. FIG. 3B shows the additive effect of the QTL identified on N09.

FIG. 4A shows the location (X-axis) and significance (LOD score on Y-axis) of the QTL identified on N11. FIG. 4B shows the additive effect of the QTL identified on N09.

FIG. 5A shows the location (X-axis) and significance (LOD score on Y-axis) of the QTL identified on N09. FIG. 5B shows the additive effect of the QTL identified on N09.

FIG. 6A shows the location (X-axis) and significance (LOD score on Y-axis) of the QTL identified on N11. FIG. 6B shows the additive effect of the QTL identified on N11.

FIG. 7 shows a Map of the major ADF QTL interval on N09, constructed with the YDN DH population. Within the 4.9 cM QTL interval, 111 SNP markers were identified, including the flanking markers DBSNP01120 and DBSNP02172. The ADF_9 and WI_9 loci are also mapped within the interval.

DISCLOSURE

Described herein are high-throughput single nucleotide polymorphism (SNP) markers and high-density genetic maps for fine mapping and validation of quantitative trait loci (QTL) underlying fiber content and seed coat color traits. In some embodiments, SNP markers tightly linked to fiber content and seed coat color traits may be used for marker-assisted selection (MAS) of desirable nutritional traits in yellow-seeded canola (YSC) lines. In particular embodiments, the YSC line may be AAFC YSC line YN01-429 and its lineage.

Also disclosed is a method of leveraging SNP markers and high-density genetic maps based on fiber content and seed coat color traits from AAFC YSC line YN01-429, using an extensive set of phenotypic data of two DH populations. In a particular embodiment, a major QTL, which explains 59.2% to 74.7% of the variance of fiber content and seed coat color traits, is described on N09 in two DH populations, and a minor QTL, which explains 1.4% to 7.2% of the variance of fiber content and seed coat color traits, is described on N11 in two DH populations. High correlation ($R^2$=0.67-0.85) exists between seed coat color traits (WI and L) and ADF content in both populations.

Figure 8:
FIG. 8 shows a map of N09 constructed with N09 of YDN, YSC and TN DH populations, showing 18 SNP markers identified within 0.0-4.9 cM to a major QTL underlying fiber content (ADF_9) and seed coat color (WI_9) on N09.

Also disclosed herein are 18 SNP markers within 0.0-4.9 cM of the major fiber content and seed coat color QTL on N09 (see FIG. 8), and 40 SNP markers within 0.0-4.1 cM of the minor fiber content and seed coat color QTL on N11, which may be used in embodiments for marker-assisted selection of complex low fiber content and YSC traits from YSC line YN01-429 and its lineage, and thus may improve the breeding process of canola lines with low ADF content if YN01-429 or it lineage is used as a low fiber content source in breeding programs.

An Low Fiber product which aims to improve the nutritional value of commercial canola meal to 85-90% of the value of 48% protein soybean meal by increasing protein content (from 36% to 44%) and true metabolizable energy (TME) (a 16%-20% increase), and decreasing fiber content (from 15-19% to less than 10%) has been developed. These improvements are anticipated to increase the nutritive value of canola meal, particularly in monogastric species, and should allow increasing dietary inclusion rates.

YSC lines (YN86-37, YN90-1016, YN97-262 and YN01-429) of low hull proportion with a thinner seed coat, low fiber and high oil as compared to black seed coat (BSC) canola (Rakow et al., 2011) also have been developed. Feeding studies comparing yellow-seeded canola meal from AAFC line YN01-429 to *B. juncea, B. rapa*, and brown-seeded *B. napus* have demonstrated the advantages of the YSC *B. napus* line, including higher protein, lower fiber, increased amino acid digestibility and metabolizable energy content, and improved nutrient and energy utilization based on feed to gain ratio in broiler chickens and monogastric animal species (Hickling, 2009; Slominski et al., 2010).

Combinations of the yellow seeded/low fiber traits from YSC lines YN97-262 and YN01-419 with the Omega 9 fatty acid profile, as well as other desirable agronomic and seed quality attributes, have been studied.

I. Mapping and Validation of Low Fiber Content and YSC Traits from YN01-429

In a preferred embodiment, the disclosure describes a method for identifying and mapping quantitative trait loci (QTL) associated with low fiber content and yellow seed coat (YSC) traits in *Brassica napus* using single-nucleotide polymorphism (SNP) markers. In embodiments, the QTLs are defined in YSC line YN01-429. In some embodiments, the markers may be used for marker-assisted selection of low fiber content and YSC traits derived from YSC line YN01-429 and its lineage.

SNP markers and high-density genetic maps were leveraged, and fiber content and seed coat color traits were fine mapped and validated from AAFC YSC line YN01-429 with an extensive set of phenotypic data from two dihaploid (DH) populations. These experiments are outlined in greater detail in Examples 1-5. Two DH populations, YSC and YDN, were developed from spring canola line crosses. The 183 DH lines of the YSC population were developed from a cross between AAFC yellow seeded/low fiber line YN01-429 and DAS Nexera black seeded/high fiber variety Nex828, and grown along with the two parents in paired row plots at the AAFC Saskatoon research farm and the DAS Rosthern research farm in Canada in 2007 for phenotyping. Seed samples from two locations were analyzed by AAFC using near-infrared spectroscopy (NIR) ADF (named ADF_A in FIGS. 3 and 4) and using Hunter lab for seed coat color White Index (named WI_A in FIGS. 3 and 4) measurement in 2007. The population was also analyzed by DAS Analytical Technologies Group in Indianapolis for ADF (named ADF_A in FIGS. 3 and 4) using the AOAC reference method (AOAC Official Method 973.18) and by DAS Bioprocess Group in Indianapolis for seed coat color White Index (named WI_D in FIGS. 3 and 4) and Hunter Lab Lightness Index (named L in FIGS. 3 and 4) measurement in 2011. The 400 DH lines of the YDN population were developed from a cross between YN01-429 and DAS Nexera black seeded/high fiber variety DN051493. The YDN population was grown along with the two parents at Pike Lake and Cudworth, Canada in 2011 for phenotyping. Seed samples were analyzed for ADF (named ADF_M1 and ADF_M2 in FIGS. 5 and 6), seed coat color White Index (named WI in FIGS. 5 and 6) and Hunter lab Lightness Index (name L in the FIGS.

5 and 6). A third DH population of 181 DH lines (named TN population) from a cross between Tapidor (a European winter cultivar) and Ningyou7 (a Chinese semi-winter cultivar) was added for consensus map construction in addition to YSC and YDN populations for QTL mapping of fiber content and seed coat color traits; TN population did not segregate for fiber content and seed coat color traits. The three DH populations were genotyped with 12,000 SNP markers and a consensus map was constructed with individual map of the YSC, YDN and TN populations. Composite Interval Mapping (CIM) was used for a whole genome QTL scan. After QTL mapping, the SNP markers within 0.0-5.0 cM of the QTL underlying fiber content and seed coat color traits were converted to KASPar assays for MAS of these traits derived from YN01-429 and its lineage.

Figure 1:
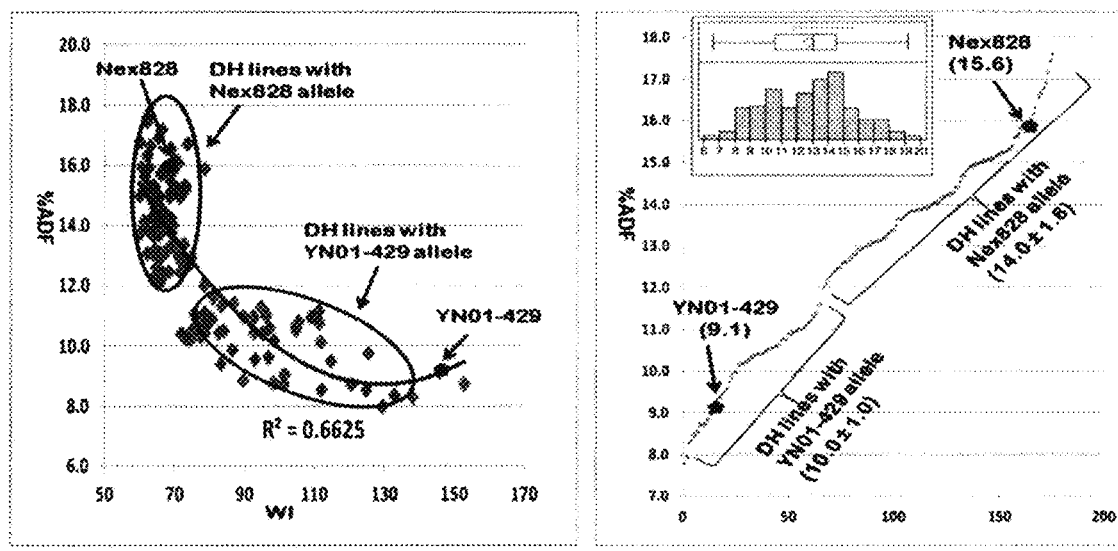
FIG. 1 shows the distribution of White Index (WI) and % ADF in Nex828×YN01-429 (YSC) DH lines. The left figure shows the White Index (WI) of seed coat color plotted against % of ADF in canola seed. The right figure shows the distribution of % ADF among DH lines. The number in bracket indicated % of ADF in canola seed.
Figure 2:
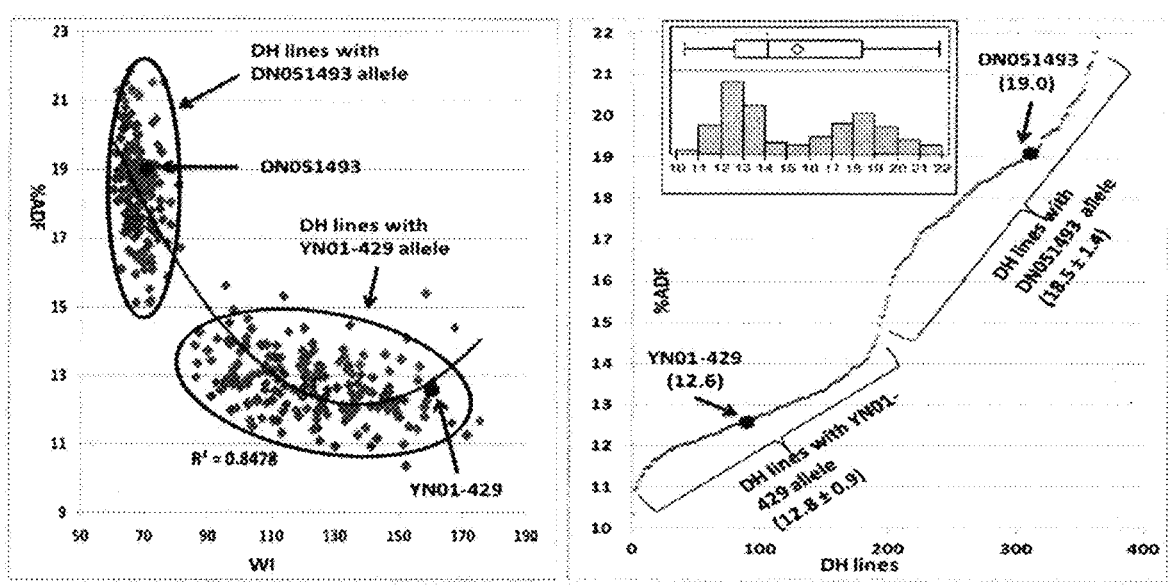
FIG. 2 shows the distribution of White Index (WI) and % ADF in DN051493×YN01-429 (YDN) DH lines. The left figure shows White Index (WI) of seed coat color plotted against % of ADF canola seed. The right figure shows the distribution of % ADF among DH lines. The number in bracket indicated % of ADF in canola seed.

High correlation was also observed between the seed coat color traits WI and L ($R^2$=0.81-0.99) and between seed coat color traits and ADF content ($R^2$=0.66-0.85) in both populations (FIGS. 1 and 2). Because of the large effect of the major QTL (R2=59.2%-74.7%) on N09, and bi-modal distributions of fiber content and seed coat color traits in DH lines (FIGS. 1 and 2), quantitative fiber content and seed coat color traits can be treated as qualitative traits. After conversion of the quantitative traits of ADF and WI into qualitative traits, the ADF (ADF_09) and WI (WI)09) were mapped to the same genomic region where the major QTL were located on N09 in both YSC and YDN populations. FIG. 7 shows the map location of major ADF and WI QTL, ADF_09 and WI_09 on the consensus map of N09 constructed with YSC, YDN and TN populations and 323 SNP markers.

Somers et al. (2001) and Rakow et al. (2011) indicated that the YSC line from AAFC delivers consistently low fiber content across multiple environments, and low lignin content is always associated with the yellow seed color. The YSC genetic map was constructed with 174 DH and 2,982 polymorphic SNP markers, a total length of 2,515.8 cM and an average length of 0.80 cM/marker. The YDN population was constructed with 397 DH lines and 2,972 SNP markers, a total length of 2,189 cM and an average length of 0.74 cM/marker. The TN genetic map was constructed with 181 DH lines and 2,716 polymorphic SNP markers, a total length of 1905.7 cM and an average length of 0.70 cM/marker. In embodiments, the disclosure describes a consensus map of 5,500 SNP markers with an average of 0.47 cM constructed with the YDN, YSC and TN populations (FIG. 7).

YSC and YDN populations segregated for fiber content and seed coat color traits and were used for QTL mapping, which further confirmed that seed coat color traits and fiber content traits were highly correlated (FIGS. 3-6). QTL mapping indicated that a major QTL was identified on linkage group (LG) N09 and a minor QTL was identified on LG N11 for all the seed coat color traits (WI and L) and ADF content in both populations (FIGS. 4-6).

In the YSC population, the major QTL identified on N09 explained 71.5% of ADF variance, and coincided with major QTL which explained 59.2% of WI and 60.8% of Lightness Index (L) variance at LOD scores ranged from 40 to 47 (FIG. 3). The minor QTL identified on N11 explained 2.4% of ADF variance, and coincided with the minor QTL which respectively explained 7.2% of WI and 6.3% of Lightness Index (L) variance at LOD scores ranged from 5 to 9 in Nex828×YN01-429 population (FIG. 4).

QTL analysis of YDN population further confirmed the results from YSC population. The major QTL identified on N09 explained 73.4% of ADF variance and coincided with the major QTL which respectively explained 74.0% of WI and 74.7% of Lightness Index (L) variance at LOD score 143 (FIG. 5). The minor QTL identified on N11 explained 1.4% of ADF variance, and coincided with the minor QTL which respectively explained 5.9% of WI and 5.7% of Lightness Index (L) variance at LOD scores ranged from 3 to 32 (FIG. 6). The results were in accordance with Somers et al. (2001) results, which indicated that a major gene explained 72.3% of the variation in seed color, as well as two additional genes that appeared to be additive and explained 21.5% of the color variation. Since seed coat color QTL (WI and L) perfectly coincided with QTL for fiber content and explained the almost the same percentage of phenotypic variance (R2=77.4%) as QTL for ADF content in both YN01-429 derived DH populations, seed coat color indexes (WI and L) were good indicators for the fiber content in canola seed if YSC line YN01-429 or its lineage is used as a low ADF content source in breeding programs.

II. SNP Markers and QTL Underlying Low Fiber Content and YSC Traits from YN01-429

In some embodiments, the disclosure describes a major QTL which explains 59.2-74.7% of the phenotypic variance of fiber content and seed coat color traits in two dihaploid (DH) plant populations. In particular embodiments, a minor QTL has been found to explain 1.4-7.2% of the phenotypic variance of these traits in two dihaploid plant populations. High correlation is disclosed between seed coat color traits (WI and L) and ADF content in both populations.

In an alternative embodiment, a set of high throughput markers closely linked to fiber content and seed coat color traits from YSC line YN01-419. In other embodiments, nucleic acid sequences linked to QTL's are associated with desirable nutritional traits. The sequence can be derived from yellow-seeded coat (YSC) line YN01-429 or its lineage. Particular embodiments related to a set of 18 SNP markers that lie within 0.0-4.9 cM of the major ADF and seed color (WI) QTL identified in Nex828×YN01-429 (YSC) and DN051493×YN01-429 (YDN) DH populations.

In a particular embodiment, the SNP markers include those markers identified as DBSNP357222 through DBSNP2222111 in FIG. 7, which flanked by DSNP01120 and DSNP02172. In another embodiment, the SNP markers include DBSNP357223, DBSNP357224, DBSNP357226, DBSNP357227, DBSNP357228, DBSNP357230, DBSNP357231, DBSNP357233, DBSNP357234, DBSNP357244, DBSNP357247, DBSNP357250, DBSNP357252, DBSNP357253, DBSNP357254, DBSNP357255, DBSNP357256, DBSNP357257, DBSNP357258, DBSNP357273, DBSNP357287, DBSNP357288, DBSNP357290, DBSNP357291, DBSNP357292, DBSNP357293, and DBSNP357294, as shown in FIG. 7.

III. Marker-Assisted Selection (MAS) of Low Fiber Content and YSC Traits from YN01-429

Certain embodiments related to a method for selecting canola plants or germplasm for a desirable nutritional trait associated with QTL's using marker-assisted selection (MAS). For example, the YSC line YN01-429 may be used. Seed color measurement may be used to replace costly and time-consuming wet chemistry analysis of fiber content. SNP markers disclosed to be within 4.9 cM of the major fiber content and seed coat color QTL on N09 or the minor fiber content and seed coat color QTL on N11 can be used for MAS, and will greatly expedite the breeding of canola lines with low fiber content, one of the most important components of DAS Low Fiber product concept.

Particular embodiments describe a method for using the identified QTL in marker-assisted selection (MAS) of the complex fiber content and seed coat color traits from the YSC line YN01-429 to facilitate breeding in *Brassica* and more efficient selection of desirable nutritional traits. Particular embodiments are directed to marker-assisted selection of canola varieties to increase the nutritive value of canola meal, particularly for feed animals, including monogastric animals and ruminants.

According to certain embodiments, the method may be used to select canola seed or germplasm comprising, on average, at least about 44% crude protein, and not more than about 14% acid detergent fiber as determined by NIR on a dry mass basis. In alternative embodiments, the canola seed or germplasm may further comprise, on average, at least about 49% crude protein content. In other embodiments, the canola seed or germplasm may comprise on average, not more than about 12% acid detergent fiber content. Additionally, the canola seed or germplasm selected by the disclosed method may further comprise the following traits: reduced glucosinolate content, low tannin content, and/or low residual cell wall content.

IV. Abbreviations

ADF acid detergent fiber
AME apparent metabolizable energy
DAS Dow AgroSciences
DH dihaploid
FAME fatty acid/fatty acid methyl esters
NMR nuclear magnetic resonance
NIR near-infrared spectroscopy
QTL quantitative trait locus
RAPD random amplified polymorphic DNA
SNP Single nucleotide polymorphism
RCW residual cell walls V. Terms Allotetraploid: As used herein, "allotetraploid" generally refers to a hybrid organism that has a chromosome set that is four times that of a haploid organism.

Canola oil: Canola oil refers to oil extracted from commercial varieties of rapeseed. To produce canola oil, seed is typically graded and blended at grain elevators to produce an acceptably uniform product. The blended seed is then crushed, and the oil is typically extracted with hexane and subsequently refined. The resulting oil may then be sold for use. Oil content is typically measured as a percentage of the whole dried seed, and particular oil contents are characteristic of different varieties of canola. Oil content can be readily and routinely determined using various analytical techniques, for example and without limitation: NMR; NIR; and Soxhlet extraction. The percent composition of total fatty acids is typically determined by extracting a sample of oil from seed, producing methyl esters of fatty acids present in the oil sample, and analyzing the proportions of the various fatty acids in the sample using gas chromatography. The fatty acid composition may also be a distinguishing characteristic of particular varieties.

Elite line: As used herein, the term "elite line" means any line that has resulted from breeding and selection for superior agronomic performance. An elite plant is any plant from an elite line.

Enhanced canola meal: As used herein, the term "enhanced canola meal" means canola meal, produced from canola seeds, which has decreased fiber content, and may have increased protein and true metabolizable energy content, as well as reduced anti-nutritional factors such as glucosinolates, tannins, phytic acid, sinapine and erucic acid. Meal with some or all of these characteristics could allow increasing inclusion rates in the diet of animal species especially in monogastric animals.

Plant line: As used herein, a "line" refers to a group of plants that display little genetic variation (e.g., no genetic variation) between individuals for at least one trait. Inbred lines may be created by several generations of self-pollination and selection or, alternatively, by vegetative propagation from a single parent using tissue or cell culture techniques. As used herein, the terms "cultivar," "variety," and "type" are synonymous, and these terms refer to a line that is used for commercial production.

Plant material: As used herein, the term "plant material" refers to any processed or unprocessed material derived, in whole or in part, from a plant. For example and without limitation, a plant material may be a plant part, a seed, a fruit, a leaf, a root, a plant tissue, a plant tissue culture, a plant explant, or a plant cell.

Quantitative trait: As used herein, a "quantitative trait" may refer to a trait or phenotype that is expressed in varying degrees, along a generally continuous gradient and is frequently linked to two or more genes and is affected by environment.

Quantitative trait locus: As used herein, a "quantitative trait locus" refers to a segment or region of DNA containing or linked to a gene or genes underlying a quantitative trait.

Seed color: In some embodiments, this disclosure refers to canola varieties (e.g., inbred canola lines and hybrids) characterized by seed color. Canola seed color rating or "seed color" is generally scored on a 1-5 scale, based on seeds obtained from healthy plants at or near complete seed maturity. "1" signifies a good yellow color. "2" signifies mainly yellow with some brown. "3" indicates a mixture of brown and yellow. "4" and "5" signify brown and black, respectively. Whiteness index (WI) scores also may be used to describe canola varieties. For example, yellow-seeded lines YN97-262 and 9592 have whiteness index scores of −34.6 and −33.2, respectively, and seed color scores of 1. Dark-seeded lines, Nex 715 and Nex 705, have whiteness index scores of −0.2 and −4.4, respectively, and seed color scores of 4. Dark-seeded lines 46A65 and Q2 have whiteness index scores of 0.3 and −3.9, respectively, and seed color scores of 5. Color of particular seeds may also be described in terms of a percentage, or other ratio, as compared to any of these lines.

Stability: As used herein, the term "stability," or "stable," refers to a given plant component that is maintained at substantially the same level through multiple generations. For example, a stable component may be maintained for at least three generations at substantially the same level. In this context, the term "substantially the same" may refer in some embodiments to a component maintained to within 25% between two different generations; within 20%; within 15%; within 10%; within 5%; within 3%; within 2%; and/or within 1%, as well as a component that is maintained perfectly between two different generations. In some embodiments, a stable plant component may be, for example and without limitation, an oil component; a protein component; a fiber component; a pigment component; a glucosinolate component; and a lignin component. The stability of a component may be affected by one or more environment factors. For example, the stability of an oil component may be affected by, for example and without limitation: temperature; location; stress; and the time of planting. Subsequent generations of a plant having a stable component under field conditions will be expected to produce the plant component in a similar manner, for example, as set forth above.

Trait or phenotype: The terms "trait" and "phenotype" are used interchangeably herein. For the purposes of the present disclosure, the traits of particular interest are low fiber content and seed coat color. Some canola varieties exhibit a yellow seed coat, while further varieties exhibit a dark (e.g., black, dark, and mottled) seed coat.

A "variety" or "cultivar" is a plant line that is used for commercial production which is distinct, stable and uniform in its characteristics when propagated.

Unless indicated otherwise, the terms "a" and "an" as used herein refer to at least one.

All references, including publications, patents, and patent applications, cited herein are hereby incorporated by reference to the extent they are not inconsistent with the explicit details of this disclosure, and are so incorporated to the same extent as if each reference were individually and specifically indicated to be incorporated by reference and were set forth in its entirety herein. The references discussed herein are provided solely for their disclosure prior to the filing date of the present application. Nothing herein is to be construed as an admission that the inventors are not entitled to antedate such disclosure by virtue of prior invention.

EXAMPLES

The following Examples are provided to illustrate certain particular features and/or aspects. These Examples should not be construed to limit the disclosure to the particular features or aspects described.

Example 1: Plant Material and DNA Extraction

For fine mapping and validation of low fiber content and seed coat color traits from yellow seed coat (YSC) line YN01-429, two dihaploid (DH) populations, YSC and YDN, were developed from crosses between spring canola lines in 2007 and 2010, respectively. The 176 DH lines of YSC population were developed from a cross between the Agriculture and Agri-Food Canada (AAFC) yellow seeded, low fiber line YN01-429 and the DAS Nexera black seeded, high fiber variety Nex828. The 399 DH lines of the YDN population were developed from a cross between YN01-429 and DAS Nexera black seeded, high fiber variety DN051493. The DH population, TN, was derived from a cross between the European winter cultivar Tapidor and the Chinese semi-winter cultivar Ningyou7. This population was a reference mapping population widely used for trait mapping and genomics studies by the international canola research community (Shi et al. 2009), and was not segregating for fiber content and seed coat color traits. It was used for consensus map construction along with the YSC and YDN populations to identify more Single Nucleotide Polymorphic (SNP) markers tightly linked to the fiber content and seed coat color traits.

Genomic DNA for the populations was extracted from 8 leaf punches per sample using the DAS Biocel extraction method (Bohl et al. 2009). DNA samples were quantified with Quant-iT™ PicoGreen® Quantification Kit (Invitrogen, Carlsbad, Calif.) using the manufacturer's instructions or with the Nanodrop 8000 Spectrophotometer (Thermo Scientific, Waltham, Mass.) per manufacturer's instructions.

Example 2: Phenotypic Data

The 176 DH lines from the YSC population were grown along with the two parents as checks in paired row plots at the AAFC Saskatoon research farm and the DAS Rosthern research farm at Canada in 2007 for phenotyping. Seed samples from all established plots were collected from both locations and analyzed by AAFC using Near Infrared Spectroscopy (NIR) for Acid Detergent Fiber (ADF) and seed coat color White Index (WI). The population was also analyzed for ADF using the AOAC reference method (AOAC Official Method 973.18) in 2007 and for seed coat color White Index and Hunter Lab Lightness Index (L) in 2011.

The YDN population was grown along with the two parents as checks in paired row plots at Pike Lake and Cudworth, Canada in 2011 for phenotyping. Seed samples from 361 DH lines were analyzed for ADF using two NIR models and for seed coat color White Index and the HunterLab Lightness Index in 2011.

Significant differences were observed between the two mapping parents for fiber content and seed coat color for both populations, as illustrated in Table 1. Distributions of fiber content in DH lines revealed bi-modal distributions skewed towards the higher fiber range in both populations (FIGS. 1 and 2). High correlation was observed between the seed coat color traits WI and L ($R^2$=0.81-0.99) and between seed coat color traits and fiber content traits ($R^2$=0.66-0.85) in both populations (FIGS. 1 and 2).

TABLE 1

The % ADF and seed coat color data, WI and L of the parents and DH lines in YSC and YDN populations.

| | YSC population | | | | YDN population | | | |
|---|---|---|---|---|---|---|---|---|
| Trait | Nex828 | YN01-429 | DH lines with Nex828 alleles | DH lines with YN01-429 alleles | DN051493 | YN01-429 | DH lines with DN051493 alleles | DH lines with YN01-429 alleles |
| % ADF | 15.6% | 9.1% | 14.0 ± 1.6% | 10.0 ± 1.0% | 19.0% | 12.6% | 18.5 ± 1.4% | 12.8 ± 0.9% |
| WI | 68.0 | 145.6 | 67.1 ± 4.2 | 100.4 ± 19.2 | 67.9 | 159.3 | 68.0 ± 5.0 | 123.5 ± 19.6 |
| L | 74.4 | 157.7 | 73.1 ± 5.0 | 109.9 ± 20.8 | 74.4 | 172.1 | 74.1 ± 5.9 | 134.8 ± 20.8 |

Example 3: Genotypic Data

The three DH populations, YSC, YDN, and TN, were genotyped with 12,000 SNP markers developed at DAS on two Illumina Infinium chips on the BeadStation 500 G per manufacturer's protocol (Illumina, San Diego, Calif.). Genotypic data was analyzed using the GenomeStudio Genotyping Analysis Module v1.8.4 (Illumina, San Diego, Calif.), which converts fluorescent signals for each SNP into A and B signals whose values reflect the relative abundance of arbitrarily assigned A and B alleles. Signal is converted into polar coordinates, using the Manhattan distance metric for the intensity R, and with Theta∈[0,1] representing angle∈[0,90] degrees. Each marker is clustered in Cartesian coordinates, and the genotypes {AA, AB, BB} are assigned to samples in clusters close to Theta={0, ½, 1}.

Example 4: Linkage Map and Consensus Map Construction

The individual maps of the YSC, YDN and TN populations were constructed with MAPMAKER/EXP 3.0 (Lander et al. 1987; Lincoln et al. 1992) at LOD score 10.0 and Haldane's mapping function, and the consensus map was constructed with Phenomap Enterprise 3.0 (GeneFlow Inc., Centreville, Va.).

The YSC genetic map was constructed with 176 DH lines and 2,982 polymorphic SNP markers, and had a total length of 2,515.8 cM and an average length of 0.80 cM/marker. The YDN genetic map was constructed with 399 DH lines and 2,972 SNP markers, and had a total length of 2,189 cM and an average of 0.74 cM/marker. The TN genetic map was constructed with 181 DH lines and 2,716 polymorphic SNP markers, and had a total length of 1905.7 cM and an average of 0.70 cM/marker. A consensus map of 5,500 SNP markers was constructed with the YDN, YSC and TN populations.

Example 5: QTL Mapping

The Composite Interval Mapping (CIM), as implemented in QTL Cartographer V2.5 (Wang et al. 2011), was used for QTL mapping. A LOD score of 3.0 was used as threshold to identify genomic regions significantly affecting the seed coat color and fiber content traits.

TABLE 2

The phenotypic variance explained (R2) by significant QTL underlying ADF content and seed coat color traits (WI and L) in YSC and YDN populations with LOD scores ≥3.

| Population | Trait | Linkage Group | % of Variance Explained ($R^2$) | LOD |
|---|---|---|---|---|
| YSC (n = 176) | Seed coat color_L | N09 | 60.8 | 41 |
| | Seed coat color_WI | N09 | 59.2 | 40 |

TABLE 2-continued

The phenotypic variance explained (R2) by significant QTL underlying ADF content and seed coat color traits (WI and L) in YSC and YDN populations with LOD scores ≥3.

| Population | Trait | Linkage Group | % of Variance Explained ($R^2$) | LOD |
|---|---|---|---|---|
| | Fiber content_ADF | N09 | 71.5 | 47 |
| | Seed coat color_L | N11 | 6.3 | 8 |
| | Seed coat color_WI | N11 | 7.2 | 9 |
| | Fiber content_ADF | N11 | 2.4 | 3 |
| YDN (n = 399) | Seed coat color_L | N09 | 74.7 | 143 |
| | Seed coat color_WI | N09 | 74 | 141 |
| | Fiber content_ADF | N09 | 73.4 | 136 |
| | Seed coat color_L | N11 | 5.7 | 26 |
| | Seed coat color_WI | N11 | 5.9 | 26 |
| | Fiber content_ADF | N11 | 1.4 | 7 |

Example 6: Mapping of ADF and Seed Coat Color as Qualitative Traits

Because of the large effect of the major QTL ($R^2$=59.2%-74.7%) on N09, and the bi-modal distributions of fiber content and seed coat color traits in the DH lines (FIGS. 1 and 2), quantitative fiber content and seed coat color traits can be treated as qualitative traits. Based on their ADF content and seed coat color WI, DH lines of both populations were divided into two groups, one with low fiber/high WI and homozygous YN01-429 alleles and the other group with high fiber/low WI and homozygous Nex828 or DN051493 alleles (FIGS. 1 and 2).

Example 7: Fine-Mapping of the Major QTL on N09

The YDN population was later used for fine mapping and validation of the major QTL on N09. A new genetic map of N09 was constructed with 1387 SNPs. Flanking markers DBSNP01120 and DBSNP02172 defined a QTL interval of 4.9 cM, corresponding to 0.46 Mb on the B. napus reference genome, DH12075, which was sequenced at AAFC through an industry consortium. The major QTL has an $R^2$ of 75% on N09. Blind screenings of the markers within the QTL interval with multiple DAS proprietary DH populations from the breeding program confirmed that the concordance between marker-predicated phenotype and actual phenotype was ≥98%. FIG. 3 shows the genetic map of the ADF QTL interval along with the ADF_09 and WI_09 loci.

Within the 4.9 cM QTL interval on N09, 111 SNP markers were identified, including the flanking markers DBSNP01120 and DBSNP02172. Table 3 lists the SNPs, their genetic positions in cM, the YN01-429 allele as well as the physical positions of the SNPs on the B. napus reference genome (DH12075).

TABLE 3

SNP markers within the 4.9 cM QTL interval for ADF mapped on N09 with the YDN population.

| SNP_Name | SEQ ID NO: | Map Position (cM) | SNP_Type | SNP_Forward | YN01429 genotype | Physical Pos on Ref Genome (bp) |
|---|---|---|---|---|---|---|
| DBSNP01120 | 1 | 117.4 | SNP | [T/G] | GG | N9:35982462..35983088 |
| DBSNP357202 | 2 | 117.4 | SNP | [C/G] | GG | N9:35982582..35984072 |
| DBSNP357203 | 3 | 117.4 | SNP | [T/G] | TT | N9:35982826..35984316 |
| DBSNP222203 | 4 | 117.4 | SNP | [A/C] | AC | N9:35987647..35987947 |

TABLE 3-continued

SNP markers within the 4.9 cM QTL interval for ADF mapped on N09 with the YDN population.

| SNP_Name | SEQ ID NO: | Map Position (cM) | SNP_Type | SNP_Forward | YN01429 genotype | Physical Pos on Ref Genome (bp) |
|---|---|---|---|---|---|---|
| DBSNP357208 | 5 | 117.4 | SNP | [T/G] | GG | N9:35994219...35995219 |
| DBSNP357214 | 6 | 117.7 | SNP | [A/G] | AA | N9:36025967...36026963 |
| DBSNP222206 | 7 | 117.7 | SNP | [A/G] | AA | N9:36027874...36028174 |
| DBSNP357215 | 8 | 118.2Q | INDEL | [-/A] | AA | N9:36030593...36031612 |
| DBSNP357216 | 9 | 118.2Q | SNP | [T/G] | TG | N9:36030597...36031616 |
| DBSNP357217 | 10 | 118.2Q | INDEL | [+/ATCACGCACCTGCAAATGT] | ATCACGCACCTGCAAATGT | N9:36030617...36031636 |
| DBSNP357218 | 11 | 118.2Q | SNP | [A/G] | GG | N9:36030736...36031756 |
| DBSNP357219 | 12 | 118.7 | SNP | [A/G] | GG | N9:36030916...36031808 |
| DBSNP357221 | 13 | 119 | SNP | [C/G] | CC | N9:36038430...36039006 |
| DBSNP357222 | 14 | 119 | SNP | [T/G] | TT | N9:36038430...36039335 |
| DBSNP357223 | 15 | 119 | SNP | [A/G] | GG | N9:36038516...36039516 |
| DBSNP357224 | 16 | 119 | SNP | [T/C] | CC | N9:36038712...36039712 |
| DBSNP222208 | 17 | 119 | SNP | [T/C] | CC | N9:36039152...36039272 |
| DBSNP357226 | 18 | 119 | SNP | [C/G] | GG | N9:36039465...36040465 |
| DBSNP357227 | 19 | 119 | SNP | [A/C] | CC | N9:36039710...36040708 |
| DBSNP357228 | 20 | 119 | SNP | [T/C] | CC | N9:36039738...36040726 |
| DBSNP357229 | 21 | 119.3 | SNP | [T/G] | GG | N9:36040629...36041743 |
| DBSNP357230 | 22 | 119.8 | SNP | [T/C] | CC | N9:36041302...36042269 |
| DBSNP357231 | 23 | 119.8 | SNP | [A/G] | AA | N9:36041326...36042293 |
| DBSNP357232 | 24 | 119.8 | SNP | [T/C] | CC | N9:36041431...36042398 |
| DBSNP357233 | 25 | 119.8 | SNP | [T/C] | CC | N9:36041470...36042437 |
| DBSNP357234 | 26 | 119.8 | SNP | [T/C] | CC | N9:36041587...36042554 |
| DBSNP357235 | 27 | 119.8 | SNP | [A/T] | AA | N9:36042193...36043188 |
| DBSNP357236 | 28 | 119.8 | INDEL | [+/TT] | TT | N9:36042318...36043314 |
| DBSNP357237 | 29 | 119.8 | SNP | [T/C] | TT | N9:36042320...36043316 |
| DBSNP357238 | 30 | 119.8 | SNP | [A/T] | TT | N9:36042626...36043621 |
| DBSNP357239 | 31 | 119.8 | SNP | [T/C] | TT | N9:36042629...36043624 |
| DBSNP357240 | 32 | 119.8 | INDEL | [+/A] | + | N9:36042765...36043760 |
| DBSNP357241 | 33 | 119.8 | SNP | [A/G] | AG | N9:36043110...36044110 |
| DBSNP357242 | 34 | 119.8 | INDEL | [-/T] | T | N9:36043117...36044117 |
| DBSNP357244 | 35 | 119.8 | SNP | [T/C] | TT | N9:36043219...36044219 |
| DBSNP357245 | 36 | 119.8 | SNP | [T/C] | CC | N9:36043480...36044475 |
| DBSNP357246 | 37 | 119.8 | SNP | [A/T] | TT | N9:36044691...36045691 |
| DBSNP357247 | 38 | 119.8 | SNP | [A/T] | TT | N9:36045200...36046200 |
| DBSNP04324 | 39 | 119.8 | SNP | [T/C] | CC | N9:36046568...36047839 |
| DBSNP357249 | 40 | 119.8 | SNP | [A/G] | AA | N9:36046761...36047762 |

TABLE 3-continued

SNP markers within the 4.9 cM QTL interval for ADF mapped on N09 with the YDN population.

| SNP_Name | SEQ ID NO: | Map Position (cM) | SNP_Type | SNP_Forward | YN01429 genotype | Physical Pos on Ref Genome (bp) |
|---|---|---|---|---|---|---|
| DBSNP357250 | 41 | 119.8 | SNP | [A/G] | AA | N9:36046762...36047763 |
| DBSNP357251 | 42 | 119.8 | SNP | [A/G] | AA | N9:36046778...36047779 |
| DBSNP357252 | 43 | 119.8 | SNP | [A/G] | GG | N9:36046868...36047869 |
| DBSNP357253 | 44 | 119.8 | SNP | [A/G] | GG | N9:36046920...36047921 |
| DBSNP357254 | 45 | 119.8 | INDEL | [+/T] | + | N9:36047652...36048534 |
| DBSNP357255 | 46 | 119.8 | SNP | [T/C] | TT | N9:36047710...36048534 |
| DBSNP357256 | 47 | 119.8 | SNP | [A/G] | GG | N9:36047752...36048534 |
| DBSNP357257 | 48 | 119.8 | SNP | [T/C] | CC | N9:36047876...36048534 |
| DBSNP357258 | 49 | 119.8 | SNP | [A/G] | AA | N9:36047941...36048534 |
| DBSNP357259 | 50 | 119.8 | SNP | [T/C] | TT | N9:36048002...36048534 |
| DBSNP357260 | 51 | 119.8 | SNP | [C/G] | GG | N9:36048012...36048534 |
| DBSNP357262 | 52 | 119.8 | INDEL | [+/A] | + | N9:36048530...36049322 |
| DBSNP357263 | 53 | 119.8 | SNP | [A/T] | TT | N9:36048530...36049347 |
| DBSNP357264 | 54 | 119.8 | SNP | [A/T] | TT | N9:36048530...36049442 |
| DBSNP357265 | 55 | 119.8 | SNP | [A/G] | AG | N9:36048530...36049520 |
| DBSNP357266 | 56 | 119.8 | SNP | [A/G] | AA | N9:36048564...36049565 |
| DBSNP357267 | 57 | 119.8 | SNP | [C/G] | CG | N9:36048641...36049642 |
| DBSNP357268 | 58 | 119.8 | SNP | [A/C] | CC | N9:36048645...36049646 |
| DBSNP357269 | 59 | 119.8 | SNP | [T/C] | TC | N9:36048651...36049652 |
| DBSNP357270 | 60 | 119.8 | SNP | [C/G] | CC | N9:36048792...36049793 |
| DBSNP357271 | 61 | 119.8 | SNP | [T/C] | CC | N9:36048794...36049795 |
| DBSNP357272 | 62 | 119.8 | INDEL | [+/A] | + | N9:36048932...36049933 |
| DBSNP357273 | 63 | 119.8 | SNP | [A/T] | TT | N9:36048985...36049986 |
| DBSNP357274 | 64 | 119.8 | SNP | [A/G] | AG | N9:36049082...36050083 |
| DBSNP357275 | 65 | 119.8 | SNP | [T/C] | TC | N9:36049455...36050457 |
| DBSNP357276 | 66 | 119.8 | SNP | [A/G] | AA | N9:36049482...36050484 |
| DBSNP357278 | 67 | 119.8 | SNP | [C/G] | CC | N9:36049554...36050556 |
| DBSNP357280 | 68 | 119.8 | SNP | [T/G] | TT | N9:36049653...36050643 |
| DBSNP357282 | 69 | 119.8 | SNP | [T/G] | TT | N9:36049758...36050643 |
| DBSNP357286 | 70 | 119.8 | SNP | [A/G] | AA | N9:36054018...36055018 |
| DBSNP222210 | 71 | 119.8 | SNP | [A/G] | AG | N9:36054461...36054578 |
| DBSNP357287 | 72 | 119.8 | SNP | [A/T] | TT | N9:36054757...36055757 |
| DBSNP357288 | 73 | 119.8 | SNP | [A/G] | GG | N9:36054789...36055789 |
| DBSNP357289 | 74 | 119.8 | SNP | [T/C] | CC | N9:36054810...36055810 |
| DBSNP357290 | 75 | 119.8 | SNP | [A/G] | AA | N9:36054813...36055813 |
| DBSNP357291 | 76 | 119.8 | SNP | [A/C] | AA | N9:36054956...36055956 |
| DBSNP357292 | 77 | 119.8 | SNP | [C/G] | CC | N9:36054966...36055966 |

TABLE 3-continued

SNP markers within the 4.9 cM QTL interval for ADF mapped on N09 with the YDN population.

| SNP_Name | SEQ ID NO: | Map Position (cM) | SNP_Type | SNP_Forward | YN01429 genotype | Physical Pos on Ref Genome (bp) |
|---|---|---|---|---|---|---|
| DBSNP357293 | 78 | 119.8 | SNP | [T/C] | TT | N9:36054983..36055983 |
| DBSNP357294 | 79 | 119.8 | SNP | [T/C] | TT | N9:36055008..36056008 |
| DBSNP84508 | 80 | 119.8 | SNP | [A/C] | AC | N9:36055121..36055879 |
| DBSNP222211 | 81 | 119.8 | SNP | [A/G] | GG | N9:36060768..36060968 |
| DBSNP222212 | 82 | 119.8 | SNP | [A/G] | GG | N9:36061805..36061924 |
| DBSNP222214 | 83 | 119.8 | SNP | [A/G] | AA | N9:36076182..36076301 |
| DBSNP222219 | 84 | 119.8 | SNP (dominant) | [T/G] | -- | N9:36096659..36096732 |
| DBSNP222220 | 85 | 119.8 | SNP (dominant) | [A/C] | -- | N9:36096733..36096814 |
| DBSNP240715 | 86 | 119.8 | SNP | [A/G] | AG | N9:36100799..36100917 |
| DBSNP222222 | 87 | 119.8 | SNP | [A/G] | GG | N9:36119793..36119830 |
| DBSNP38295 | 88 | 119.8 | SNP | [A/G] | GG | N9:36132536..36133536 |
| DBSNP222225 | 89 | 119.8 | SNP | [A/G] | GG | N9:36132936..36133136 |
| DBSNP222226 | 90 | 119.8 | SNP | [A/G] | AA | N9:36136254..36136558 |
| DBSNP08212 | 91 | 119.8 | SNP | [A/G] | AA | N9:36143105..36143329 |
| DBSNP08214 | 92 | 119.8 | SNP | [T/G] | TT | N9:36143105..36143329 |
| DBSNP222228 | 93 | 119.8 | SNP | [T/C] | CC | N9:36147820..36147940 |
| DB SNP222229 | 94 | 120.1 | SNP | [A/G] | AA | N9:36156553..36156673 |
| DBSNP42126 | 95 | 120.1 | SNP | [T/G] | GG | N9:36157370..36158339 |
| DBSNP222231 | 96 | 120.1 | SNP | [T/C] | TT | N9:36165969..36166169 |
| DBSNP222233 | 97 | 120.6 | SNP | [A/G] | AA | N9:36175905..36176121 |
| DBSNP222235 | 98 | 120.6 | SNP | [A/G] | AA | N9:36190213..36190333 |
| DBSNP146598 | 99 | 120.6 | SNP | [T/C] | TC | N9:36207823..36208597 |
| DBSNP147032 | 100 | 120.6 | SNP | [A/G] | AG | N9:36212362..36213110 |
| DBSNP94819 | 101 | 120.6 | SNP | [T/G] | TG | N9:36213988..36214561 |
| DBSNP158066 | 102 | 120.6 | SNP | [A/T] | TA | N9:36214885..36215409 |
| DBSNP158078 | 103 | 120.6 | SNP | [T/C] | CC | N9:36214926..36215606 |
| DBSNP63288 | 104 | 121.4 | SNP | [T/G] | TG | N9:36278558..36279063 |
| DBSNP52362 | 105 | 121.4 | SNP | [T/C] | + | N9:36279239..36280186 |
| DBSNP222241 | 106 | 121.4 | SNP | [T/C] | -- | N9:36291810..36291930 |
| DBSNP222242 | 107 | 121.4 | SNP | [T/C] | TT | N9:36308543..36308663 |
| DBSNP189108 | 108 | 121.4 | SNP | [T/C] | TC | N9:36308946..36309355 |
| DBSNP222244 | 109 | 121.7 | SNP | [T/C] | CC | N9:36353147..36353447 |
| DBSNP222246 | 110 | 122 | SNP | [T/G] | TT | N9:36372163..36372403 |
| DBSNP02172 | 111 | 122.3 | SNP | [C/G] | CC | N9:36447139..36448664 |

Within the 4.9 cm ADF QTL interval, flanked by DBSNP01120 and DBSNP02172, a sub-interval was defined in which the markers are most desired for marker assisted selection. Flanking markers DBSNP35722 and DBSNP222211 define a 0.5 cM sub-interval haplotype region unique to the donor YN01-429. The DBSNP35722 and DBSNP222211 flanking markers and the markers within the sub-interval can be used for marker assisted selection to track the QTL on N09 when breeding for enhanced ACM attributes.

We claim:

1. A method for marker-assisted canola plant selection, the method comprising:
   crossing a first canola plant with a second, different canola plant, wherein the first canola plant is from canola line YN01-429 or its lineage or canola line YN97-262 or its lineage, and wherein the first canola plant comprises a haplotype associated with decreased fiber comprising marker alleles at a locus within the canola N09 chromosomal interval comprising and flanked by SEQ ID NO:1 and SEQ ID NO:111, thereby producing a progeny plant population; and
   detecting in a plant of the progeny population the haplotype associated with decreased fiber.

2. The method according to claim 1, the method further comprising:
   backcrossing the plant of the progeny population comprising the haplotype associated with decreased fiber with the first or second canola plant.

3. The method according to claim 1, wherein the marker alleles are at a locus comprising and flanked by SEQ ID NO:14 and SEQ ID NO:81.

4. The method according to claim 1, wherein the first canola plant is from canola line YN01-429.

5. The method according to claim 1, wherein the marker allele is a single-nucleotide polymorphism (SNP).

6. The method according to claim 1, wherein the first canola plant is from canola line YN97-262.

7. The method according to claim 3, wherein the marker alleles are selected from the group consisting of a thymine (T) at position 501 of SEQ ID NO:14, a guanine (G) at position 501 of SEQ ID NO:15, a cytosine (C) at position 501 of SEQ ID NO:16, a C at position 61 of SEQ ID NO:17, a G at position 501 of SEQ ID NO:18, a C at position 501 of SEQ ID NO:19, a C at position 501 of SEQ ID NO:20, a G at position 501 of SEQ ID NO:21, a C at position 501 of SEQ ID NO:22, an adenine (A) at position 501 of SEQ ID NO:23, a C at position 501 of SEQ ID NO:24, a C at position 501 of SEQ ID NO:25, a C at position 501 of SEQ ID NO:26, an A at position 501 of SEQ ID NO:27, a TT at position 502 of SEQ ID NO:28, a T at position 501 of SEQ ID NO:29, a T at position 501 of SEQ ID NO:30, a T at position 501 of SEQ ID NO:31, a T at position 502 of SEQ ID NO:32, a T at position 501 of SEQ ID NO:34, a T at position 501 of SEQ ID NO:35, a C at position 501 of SEQ ID NO:36, a T at position 501 of SEQ ID NO:37, a T at position 501 of SEQ ID NO:38, a C at position 536 of SEQ ID NO:39, an A at position 501 of SEQ ID NO:40, an A at position 501 of SEQ ID NO:41, an A at position 501 of SEQ ID NO:42, a G at position 501 of SEQ ID NO:43, a G at position 501 of SEQ ID NO:44, an A at position 502 of SEQ ID NO:45, a T at position 501 of SEQ ID NO:46, a G at position 501 of SEQ ID NO:47, a C at position 501 of SEQ ID NO:48, an A at position 501 of SEQ ID NO:49, a T at position 501 of SEQ ID NO:50, a G at position 501 of SEQ ID NO:51, a C at position 502 of SEQ ID NO:52, a Tat position 501 of SEQ ID NO:53, a Tat position 501 of SEQ ID NO:54, an A at position 501 of SEQ ID NO:56, a C at position 501 of SEQ ID NO:58, a C at position 501 of SEQ ID NO:60, a C at position 501 of SEQ ID NO:61, a C at position 502 of SEQ ID NO:62, a T at position 501 of SEQ ID NO:63, an A at position 501 of SEQ ID NO:66, a C at position 501 of SEQ ID NO:67, a T at position 501 of SEQ ID NO:68, a T at position 501 of SEQ ID NO:69, an A at position 501 of SEQ ID NO:70, a T at position 501 of SEQ ID NO:72, a G at position 501 of SEQ ID NO:73, a C at position 501 of SEQ ID NO:74, an A at position 501 of SEQ ID NO:75, an A at position 501 of SEQ ID NO:76, a C at position 501 of SEQ ID NO:77, a T at position 501 of SEQ ID NO:78, a T at position 501 of SEQ ID NO:79, and a G at position 101 of SEQ ID NO:81.

8. The method according to claim 7, wherein the first canola plant is from canola line YN01-429.

9. The method according to claim 7, wherein the first canola plant is from canola line YN97-262.

10. The method according to claim 1, wherein the marker alleles are selected from the group consisting of a guanine (G) at position 283 of SEQ ID NO:1, a guanine (G) at position 501 of SEQ ID NO:2, a thymine (T) at position 501 of SEQ ID NO:3, a G at position 501 of SEQ ID NO:5, an adenine (A) at position 501 of SEQ ID NO:6, an A at position 151 of SEQ ID NO:7, an A at position 501 of SEQ ID NO:8, a 19 nucleotide insertion at position 502 of SEQ ID NO:10, a G at position 501 of SEQ ID NO:11, a G at position 501 of SEQ ID NO:12, a cytosine (C) at position 501 of SEQ ID NO:13, a G at position 61 of SEQ ID NO:82, an A at position 61 of SEQ ID NO:83, a G at position 61 of SEQ ID NO:87, a G at position 501 of SEQ ID NO:88, a G at position 101 of SEQ ID NO:89, an A at position 151 of SEQ ID NO:90, an A at position 153 of SEQ ID NO:91, a T at position 48 of SEQ ID NO:92, a C at position 61 of SEQ ID NO:93, an A at position 61 of SEQ ID NO:94, a G at position 501 of SEQ ID NO:95, a T at position 101 of SEQ ID NO:96, an A at position 151 of SEQ ID NO:97, an A at position 61 of SEQ ID NO:98, a C at position 328 of SEQ ID NO:103, a T at position 61 of SEQ ID NO:107, a C at position 151 of SEQ ID NO:109, a T at position 151 of SEQ ID NO:110, and a C at position 848 of SEQ ID NO:111.

11. The method according to claim 10, wherein the first canola plant is from canola line YN01-429.

12. The method according to claim 10, wherein the first canola plant is from canola line YN97-262.

\* \* \* \* \*

SEQUENCE LISTING

```
<160> NUMBER OF SEQ ID NOS: 111

<210> SEQ ID NO 1
<211> LENGTH: 532
<212> TYPE: DNA
<213> ORGANISM: Brassica napus
<220> FEATURE:
<221> NAME/KEY: misc_feature
<222> LOCATION: (295)..(295)
<223> OTHER INFORMATION: where n is a, t, c, or g
<220> FEATURE:
<221> NAME/KEY: misc_feature
<222> LOCATION: (369)..(369)
<223> OTHER INFORMATION: where n is a, t, c, or g
<220> FEATURE:
<221> NAME/KEY: misc_feature
<222> LOCATION: (441)..(441)
<223> OTHER INFORMATION: where n is a, t, c, or g
<220> FEATURE:
<221> NAME/KEY: misc_feature
<222> LOCATION: (452)..(452)
<223> OTHER INFORMATION: where n is a, t, c, or g
<220> FEATURE:
<221> NAME/KEY: misc_feature
<222> LOCATION: (473)..(473)
<223> OTHER INFORMATION: where n is a, t, c, or g

<400> SEQUENCE: 1
gaatttccgg gtcgacatca tcgaggccgg gttccccgcc gcgtccaaag acgacttcga      60
ggcggtcaag accatttccg aaaccgtcgg aaacgccgtc gacgagaacg gttacgtccc     120
cgtcatctgc ggtctctcga ggtgcaacga gagagatatc cagacggctt gggaggctgt     180
gagatacgcc aaaaggccta ggatccatac gttcatcgcc acgagtgata ttcacttgga     240
gtataagctc aagaagagta aacaagaagt catcgagatc gckaggagca tggtntaggt     300
tcgctaggag cttggggtgt gatgacgtgg agtttagtcc tgaagatgca ggaaggtcgg     360
agagagagnt ttttgtatga gattcttgga gaagtgataa aagctggagc gacgacactt     420
aatattcctg atactgttgg ntatcacttt gncctagtga gtttggtcag ttngattgct     480
gatataaagg ctaataccc tgggattgag aacgttgtca tctcgactca tt             532

<210> SEQ ID NO 2
<211> LENGTH: 1001
<212> TYPE: DNA
<213> ORGANISM: Brassica napus

<400> SEQUENCE: 2
ctccagcttt tatcacttct ccaagaatct catacaaaaa ctctctctcc gacctgttaa      60
acaaattaaa ataaatataa acagttacag agaaagtgaa agcttggtaa tcaagattag     120
aactaattaa aataaataaa agataattaa accccccacc ttcctgcatc ttcaggacta     180
aactccacgt catcacaccc caagctccta gcgaacctaa ccatgctcct cgcgatctcg     240
atgacttctt gtttactctt cttgagctta tactccaagt gaatatcact cgtggcgatg     300
aacgtatgga tcctaggcct tttggcgtat ctcacagcct cccaagccgt ctggatatct     360
ctctcgttgc acctcgagag accgcagatg acggggacgt aaccgttctc gtcgacggcg     420
tttccgacgg tttcggaaat ggtcttgacc gcctcgaagt cgtctttgga cgcggcgggg     480
```

```
aacccggcct cgatgatgtc sacgccgagc ttcgcgagct gccgcgcgat gtcgagcttc    540
tccttggagg tgagggtggc gccgggggac tgctcgccgt cgcggagcgt ggtgtcgaag    600
atgcggacgt agttggggtc ggaaatgcgg ttggggatgt agtccgggcg gcggcggcgg    660 aggggggtggg gagggagagg gggcggtgga tctgagatgg agcaggagag gcggagggag    720
gcggaggagg agcggcggcg gtggtgggat ggtgggaaac ggaaggagag tggtgtggtg    780
attgttgtgg agaaggtggg gagagaaggt gttgttgttg atgatgagag tgaagggttt    840
ctgagaaggg aagacgccat ggagacgat tgtgagaaga atggtaaacc taagagaga     900 gagagatgaa ggtttgaacg tggcggcggc agctacttgg ttaagctcta tctgttcgtt    960
cgtgtcactc ttctctttat ttgacaaaaa caaatctttt t                       1001
```

<210> SEQ ID NO 3
<211> LENGTH: 1001
<212> TYPE: DNA
<213> ORGANISM: Brassica napus

<400> SEQUENCE: 3

```
cttcttgttt actcttcttg agcttatact ccaagtgaat atcactcgtg gcgatgaacg     60
tatggatcct aggccttttg gcgtatctca cagcctccca agccgtctgg atatctctct    120
cgttgcacct cgagagaccg cagatgacgg ggacgtaacc gttctcgtcg acggcgtttc    180
cgacggtttc ggaaatggtc ttgaccgcct cgaagtcgtc tttggacgcg gcggggaacc    240
cggcctcgat gatgtcgacg ccgagcttcg cgagctgccg cgcgatgtcg agcttctcct    300
tggaggtgag ggtggcgccg ggggactgct cgccgtcgcg gagcgtggtg tcgaagatgc    360
ggacgtagtt ggggtcggaa atgcggttgg ggatgtagtc cgggcggcgg cggcggaggg    420
ggtggggagg gagaggggc ggtggatctg agatggagca ggagaggcgg agggaggcgg    480
aggaggagcg gcggcggtgg kgggatggtg ggaaacggaa ggagagtggt gtggtgattg    540
ttgtggagaa ggtggggaga gaaggtgttg ttgttgatga tgagagtgaa gggtttctga    600
gaagggaaga cgccattgga gacgattgtg agaagaatgg taaacctaaa gagagagaga    660
gatgaaggtt tgaacgtggc ggcggcagct acttggttaa gctctatctg ttcgttcgtg    720
tcactcttct ctttatttga caaaaacaaa tcttttttt tggtcccact tgaatattct    780
ccacttaaaa aaatgagtac gacaactgtg ttatacttta acggcgtcg ttataggata    840 caatagaaaa agtcgaccgg caacgataag gacgatgagt cgattgaaca gtttagaaag    900
gacgtagaac catgagattc accaataagc attgaacaag aagacatgga gatggaaagt    960
tgttaaaaca ttttttaaat gaacttaaca tgtcacattg t                       1001
```

<210> SEQ ID NO 4
<211> LENGTH: 301
<212> TYPE: DNA
<213> ORGANISM: Brassica napus

<400> SEQUENCE: 4

```
caaracattt tcacatatat cacttycatg ctcacytcca ccaaccacaa aaaaatgacg     60
agtactataa agcaagaagg acaaagcata cccaatatt ataaataaat cccaccagct    120
gagtgcatct acatcgcctg agtattaaaa mataaaacaa ggagggccga taagaaggaa    180
gggaacgcaa taacattatc tatgaagata agacttcaga aggcagagag accaagtaag    240
aaaattatgt aggcaagcat tcaagagata caacattacc agtaagcttty aggaggataa    300 a                                                                   301
```

<210> SEQ ID NO 5
<211> LENGTH: 1001
<212> TYPE: DNA
<213> ORGANISM: Brassica napus

<400> SEQUENCE: 5

| | | | | | |
|---|---|---|---|---|---|
| tagcatgccc | agtagtagca | aaagaagtga | gcacctaaca | cgaaaaaacg | ccaaagtcat | 60 |
| gctgctttca | caagagcagg | tagaaaacaa | agaaaaggg | aatatacagg | attcttagcc | 120 |
| atgaacaatg | cctggaactt | tgtattttc | aaacattagc | tctgccgccc | tgtcaagcat | 180 |
| acaatttgag | aacatcagta | acacactcaa | agatgaacta | acataagaca | aaagtaaata | 240 |
| tctataagca | gataaatcag | acttctctct | atgctgttga | gtgtttaaag | gaggctcagc | 300 |
| tagcagcatg | ggctgctcct | taggatcaat | catcaaacaa | ctccttcaga | cataaaaaaa | 360 |
| catattagag | atgacatcaa | acaataattt | atgagaaaaa | actaaagctt | tatacagttt | 420 |
| acctgaatgc | atgttcccat | ttttgtttat | taaaatattg | caaaaataat | tgactaaatc | 480 |
| ttcatataca | aaattttgac | kgaaaactgc | agctttcatc | ttcttcctgg | agatttaggt | 540 |
| ttatatctcc | aattggattg | gatttgttct | cttgaaggga | ttaaaacgaa | aaagagggaa | 600 |
| aacaaaataa | aacgccgttg | ccggggatcg | aacccgggtc | accgcgtga | caggcgtgaa | 660 |
| tacttaccac | tatactacaa | cgactcagtt | gattaaagat | tcaatcaaaa | tatactgaaa | 720 |
| taaaaagtt | tacgctttga | aatgggagac | agagctcaac | gtacgcactc | acgagattct | 780 |
| ccagcctcgc | aaccaactcc | atcagtagcg | aagcgaatca | aaatttactg | aaataaaaaa | 840 |
| aaggttacac | tttgaaactt | actttctaag | taattgacaa | tacaatatac | aaagaaatgg | 900 |
| catattaaag | tctctttatc | gctgtcttaa | tcttcttggt | tccactcttg | ctccattcag | 960 |
| ctagtcagct | ctcgcccaag | gtccgagttg | taacggcccg | g | | 1001 |

<210> SEQ ID NO 6
<211> LENGTH: 1001
<212> TYPE: DNA
<213> ORGANISM: Brassica napus

<400> SEQUENCE: 6

| | | | | | |
|---|---|---|---|---|---|
| ctttgccttt | gtcttattat | ttgatcttct | ttacagctgt | gtacgagtca | gctaaacatt | 60 |
| gctccgttac | tcctctccag | tattaaatca | tgccaggcca | gcgcaagatt | gttatttgac | 120 |
| tacttttcct | tccaattacg | ttggattact | tcttgatttt | agttgtgccg | caagatctca | 180 |
| gatttctaaa | ctctgatgca | tcaccttctc | ctctattggg | tttaaaagag | ttaattaacc | 240 |
| agaagatcaa | acatataatt | tggatttgtg | tttgttttga | ccataaatat | gttgaaagca | 300 |
| gcgtacatgc | tactgctttt | atctgggaat | ggtgttagct | taatatggaa | agcgatcatg | 360 |
| attaggagca | accttagacc | ctatatttc | tacacatggc | tgaaggtgat | atggtacgag | 420 |
| ataatataat | tctattttatt | tgtagttaat | acccttctac | atatatttga | tgcagaatca | 480 |
| tcaaaccgta | actctcccgc | rgtaatttga | aggccatgga | agtaatgtt | tctttactc | 540 |
| attgtaactt | aatcatatgc | tcttttcatg | ttcgtcacat | ctcacaactt | aagaaatcgt | 600 |
| tgctacagtt | cttcactttt | ttccttgtgg | taaagtatat | tttactatt | ctttcataca | 660 |
| tctctttgta | gttaaagtag | caagagaatt | atgagtctga | tgtaggatac | aagaggtatc | 720 |
| cccaaagaag | attaactgcc | caaaacaca | tgatatctac | taaccagcct | ctaattacca | 780 |
| aagtagtatc | tttttctaat | gcatatatac | attgattttt | atctatgtag | gtttagtcac | 840 |

```
tatatatata ggaggtgcga ctagccatca tttgaattta ttcccactct cattgcagtt    900
tgatcactgg tcagaaatgg gacggttaca cgatctgatt ggtagtagag gcacgcgcag    960
gggggggggg ggtacactta cagccatagt cggagaagtc t                       1001
```

<210> SEQ ID NO 7
<211> LENGTH: 301
<212> TYPE: DNA
<213> ORGANISM: Brassica napus

<400> SEQUENCE: 7

```
aacatcagca agaaggtaac ttgtacacaa ttgaggttta tgttctggta ctttcggtta     60
ggtttgcact tggtgggcaa gaaattgtgg cttttgacct ggaattagtg tgtcacaata    120
ggcaaacaac ttcagtgacc catcttaaac rtaatgctaa gaagcagtgt atttgtttcg    180
tgcttttgaa gtttgaatat attttttctt tctcctttt attaccacaa actactctta    240
tttcctggtt aaaagataaa acgtatggga agcctggtcg tcttactga gtcattatgc     300 a                                                                   301
```

<210> SEQ ID NO 8
<211> LENGTH: 1001
<212> TYPE: DNA
<213> ORGANISM: Brassica napus
<220> FEATURE:
<221> NAME/KEY: misc_feature
<222> LOCATION: (501)..(501)
<223> OTHER INFORMATION: where n is an insertion/deletion [-/A]

<400> SEQUENCE: 8

```
caagttcaat gagaagggaa aaaataaca gcgttaacac accttaaaag tattatcatc     60
aggaaacatc tcaagagcct gaccctggt cacttcaatc ctttcaaatg gatgtccttc    120
ctaagatgtc agaggaataa actcaaagct ttgtaaaaga agcaaagaaa tatactgtaa    180
ggagaaatac agagatatca aaaataaaga tatgacaaga ctgaataaga agcagtactc    240
gagcatcccc tgcttcagtt tcgggaaagt gttgctcgtt taaacccaga tcgccataga    300
atgcatcgta gaagaaaccc tggatagaca accaaacaaa taatagagag gcaagcacaa    360
agacacagac aaaaagaatc gctgcaggct cttagtctta cctcatctct agctttgcag    420
ggtccaacgc acagcttaca accatactcc tgttcgagaa ccatggtcaa tgtttaccac    480
aatcaagacg agataaaaaa ngtgttttta ccagggcgag aatgtgagcg ctagaacgcc    540
agaaagtatc acggcctttg tcgctgtcaa aactgaaaaa ctcaagcgaa caatcagctt    600
ccagtggcct attcatgtcc cagaggacat cgtttaccga agagatcagc gctgagtttg    660
ccaatcccac agaaatttgc ctcgcgattt ctgctggagt cgtctcccat ctcttccctt    720
ctttcacgtt tccaccatct cgaattgtaa ccctaattaa gttcacagca gaacaacatt    780
actgtagccc tagctacgca aagtatatat cagcatctat tgtgtttact tgatcggctc    840
gtgtggccga gactgaatct ccgcgagctg cttcgcttgg aactcctcga agagcctgat    900
acgcttctcg atgacggctg agagataagc ctcgtccctg ggatgttcat ccgccatcgt    960
tggacttgga ggagcacaga aagtgacgaa aggccaaggg a                      1001
```

<210> SEQ ID NO 9
<211> LENGTH: 1001
<212> TYPE: DNA
<213> ORGANISM: Brassica napus

<400> SEQUENCE: 9

```
ttcaatgaga agggaaaaaa ataacagcgt taacacacct taaaagtatt atcatcagga         60
aacatctcaa gagcctgacc cctggtcact tcaatccttt caaatggatg tccttcctaa        120
gatgtcagag gaataaactc aaagctttgt aaaagaagca agaaatata ctgtaaggag         180 aaatacagag atatcaaaaa taaagatatg acaagactga ataagaagca gtactcgagc        240
atcccctgct tcagtttcgg gaaagtgttg ctcgtttaaa cccagatcgc catagaatgc        300
atcgtagaag aaaccctgga tagacaacca aacaaataat agagaggcaa gcacaaagac        360
acagacaaaa agaatcgctg caggctctta gtcttacctc atctctagct ttgcagggtc        420
caacgcacag cttacaacca tactcctgtt cgagaaccat ggtcaatgtt taccacaatc        480
aagacgagat aaaaaaagtg kttttaccag ggcgagaatg tgagcgctag aacgccagaa        540
agtatcacgg cctttgtcgc tgtcaaaact gaaaaactca agcgaacaat cagcttccag        600
tggcctattc atgtcccaga ggacatcgtt taccgaagag atcagcgctg agtttgccaa        660
tcccacagaa atttgcctcg cgatttctgc tggagtcgtc tcccatctct tcccttcttt        720
cacgtttcca ccatctcgaa ttgtaaccct aattaagttc acagcagaac aacattactg        780
tagccctagc tacgcaaagt atatatcagc atctattgtg tttacttgat cggctcgtgt        840
ggccgagact gaatctccgc gagctgcttc gcttggaact cctcgaagag cctgatacgc        900
ttctcgatga cggctgagag ataagcctcg tccctgggat gttcatccgc catcgttgga        960
cttggaggag cacagaaagt gacgaaaggc caagggatga t                          1001

<210> SEQ ID NO 10
<211> LENGTH: 1002
<212> TYPE: DNA
<213> ORGANISM: Brassica napus
<220> FEATURE:
<221> NAME/KEY: misc_feature
<222> LOCATION: (502)..(502)
<223> OTHER INFORMATION: where n is an insertion/deletion
      [+/ATCACGCACCTGCAAATGT]

<400> SEQUENCE: 10
ataacagcgt taacacacct taaaagtatt atcatcagga aacatctcaa gagcctgacc         60
cctggtcact tcaatccttt caaatggatg tccttcctaa gatgtcagag gaataaactc        120
aaagctttgt aaaagaagca agaaatata ctgtaaggag aaatacagag atatcaaaaa        180
taaagatatg acaagactga ataagaagca gtactcgagc atcccctgct tcagtttcgg        240
gaaagtgttg ctcgtttaaa cccagatcgc catagaatgc atcgtagaag aaaccctgga        300
tagacaacca aacaaataat agagaggcaa gcacaaagac acagacaaaa agaatcgctg        360
caggctctta gtcttacctc atctctagct ttgcagggtc caacgcacag cttacaacca        420
tactcctgtt cgagaaccat ggtcaatgtt taccacaatc aagacgagat aaaaaaagtg        480
tttttaccag ggcgagaatg tngagcgcta aacgccaga aagtatcacg gcctttgtcg        540
ctgtcaaaac tgaaaaactc aagcgaacaa tcagcttcca gtggcctatt catgtcccag        600
aggacatcgt ttaccgaaga gatcagcgct gagtttgcca atcccacaga atttgcctc        660 gcgatttctg ctggagtcgt ctcccatctc ttcccttctt tcacgtttcc accatctcga        720
attgtaaccc taattaagtt cacagcagaa caacattact gtagccctag ctacgcaaag        780
tatatatcag catctattgt gtttacttga tcggctcgtg tggccgagac tgaatctccg        840
cgagctgctt cgcttggaac tcctcgaaga gcctgatacg cttctcgatg acggctgaga        900
gataagcctc gtccctggga tgttcatccg ccatcgttgg acttggagga gcacagaaag        960
```
tgacgaaagg ccaagggatg attttttaaa cgacgaatga ga        1002

<210> SEQ ID NO 11
<211> LENGTH: 1001
<212> TYPE: DNA
<213> ORGANISM: Brassica napus

<400> SEQUENCE: 11
caaagctttg taaagaagc aagaaatat actgtaagga gaaatacaga gatatcaaaa         60
ataaagatat gacaagactg aataagaagc agtactcgag catcccctgc ttcagtttcg       120
ggaaagtgtt gctcgtttaa acccagatcg ccatagaatg catcgtagaa gaaaccctgg       180
atagacaacc aaacaaataa tagagaggca agcacaaaga cacagacaaa aagaatcgct       240
gcaggctctt agtcttacct catctctagc tttgcagggt ccaacgcaca gcttacaacc       300
atactcctgt tcgagaacca tggtcaatgt ttaccacaat caagacgaga taaaaaagt        360
gttttttacca gggcgagaat gtgagcgcta gaacgccaga aagtatcacg gcctttgtcg      420
ctgtcaaaac tgaaaaactc aagcgaacaa tcagcttcca gtggcctatt catgtcccag       480
aggacatcgt ttaccgaaga ratcagcgct gagtttgcca atcccacaga aatttgcctc      540
gcgatttctg ctggagtcgt ctcccatctc ttcccttctt tcacgtttcc accatctcga       600
attgtaaccc taattaagtt cacagcagaa caacattact gtagccctag ctacgcaaag      660
tatatatcag catctattgt gtttacttga tcggctcgtg tggccgagac tgaatctccg      720
cgagctgctt cgcttggaac tcctcgaaga gcctgatacg cttctcgatg acggctgaga     780
gataagcctc gtccctggga tgttcatccg ccatcgttgg acttggagga gcacagaaag      840
tgacgaaagg ccaagggatg attttttaaa cgacgaatga gagcagacgg gacgatttta      900
tgacaccact ttaccaaagt ttttagtatt taagatttt ttcaaaaaaa aaaaaaagaa        960
tttaattaat ttgcctatttt tcacagattt aattccttg c                          1001

<210> SEQ ID NO 12
<211> LENGTH: 1001
<212> TYPE: DNA
<213> ORGANISM: Brassica napus

<400> SEQUENCE: 12
atagacaacc aaacaaataa tagagaggca agcacaaaga cacagacaaa aagaatcgct       60
gcaggctctt agtcttacct catctctagc tttgcagggt ccaacgcaca gcttacaacc      120
atactcctgt tcgagaacca tggtcaatgt ttaccacaat caagacgaga taaaaaaagt     180
gttttttacca gggcgagaat gtgagcgcta gaacgccaga aagtatcacg gcctttgtcg     240
ctgtcaaaac tgaaaaactc aagcgaacaa tcagcttcca gtggcctatt catgtcccag      300
aggacatcgt ttaccgaaga gatcagcgct gagtttgcca atcccacaga aatttgcctc      360
gcgatttctg ctggagtcgt ctcccatctc ttcccttctt tcacgtttcc accatctcga      420
attgtaaccc taattaagtt cacagcagaa caacattact gtagccctag ctacgcaaag     480
tatatatcag catctattgt rtttacttga tcggctcgtg tggccgagac tgaatctccg     540
cgagctgctt cgcttggaac tcctcgaaga gcctgatacg cttctcgatg acggctgaga    600
gataagcctc gtccctggga tgttcatccg ccatcgttgg acttggagga gcacagaaag     660
tgacgaaagg ccaagggatg attttttaaa cgacgaatga gagcagacgg gacgatttta    720
tgacaccact ttaccaaagt ttttagtatt taagatttt ttcaaaaaaa aaaaaaagaa       780

```
tttaattaat ttgcctattt tcacagattt aattcctttg ctactacaga tttgttgttt    840 cttttctttta attctaattc atttacatgt atactagatt cgttttccgc gctacgcgcg    900
gattacatga ttcaaatttg ttaatttaca aaaaatttca ctacatttac aatattacta    960
attgtttata aaacatttta aaacacaata attttatagt t                        1001
```

<210> SEQ ID NO 13
<211> LENGTH: 1001
<212> TYPE: DNA
<213> ORGANISM: Brassica napus

<400> SEQUENCE: 13

```
gaagattttt cgaaagaatt ttttcagctt tttttttttt tttttttggg gtttatgggg     60
aattcttctt tggtttcatt tgttttatat tttgattttc aggcgtctga atacctgggt    120
tgttggatta agcttgaaag aaaaagtaaa cttgagaaat aagttaactt ctaatcctac    180
tgagttatgg tttaaaggat tagaaaatat ccgaataaat tatcctaatg aatttaggat    240
taagaaaaag gaaatatgtg ttttctaatg agtttaggaa atttgattta tatataagga    300
gatgcaaggg tgttgcataa cttatgagtt ttgtgattgt gtgagagctt gaggttttg     360 agtgagtttt cctcaagaga ttaataagag agttattctt attatagagt ttatacaatt    420
cgagattcta tatgggtatg gaatcgctcg tggaactcac cacccagtca ttggcaaatt    480
atctcaaagg caagaatccc stcaccattc gatctttgtg gaaggtggaa ggcgacctca    540
ctgctgagga ggaagctaag gcgttggcga tgggcgtggc gaaattagga cattaagtcc    600
attgatgctc tacaaaatct tatgtgatta ctgaagtctg aagaagtttg tccaagtgtc    660
gtttgtttga agtcaaaaat aaagatgtag caggattatc aagttctgat cattaaaagt    720
cctattataa tttctatgtt tcatcatcac tttgaagttc agttaatcaa aagtacgatt    780
caagaatatt ccagtactgt ttctcgatcc attattacca aaaagtttag ctaattatct    840
tcctggaaac ttcttctgtt ccccccatag agaaagttgt cctgccttta gttccagatt    900
aaataagatg agtatcaagt acccatatgt attttcttcc aaaatataag aacataatat    960
ccaactataa tttaagaaaa aacaaagatt agtggagaac g                        1001
```

<210> SEQ ID NO 14
<211> LENGTH: 1001
<212> TYPE: DNA
<213> ORGANISM: Brassica napus

<400> SEQUENCE: 14

```
tttgtgattg tgtgagagct tgaggttttt gagtgagttt tcctcaagag attaataaga     60
gagttattct tattatagag tttatacaat tcgagattct atatgggtat ggaatcgctc    120
gtggaactca ccacccagtc attggcaaat tatctcaaag gcaagaatcc cctcaccatt    180
cgatctttgt ggaaggtgga aggcgacctc actgctgagg aggaagctaa ggcgttggcg    240
atgggcgtgg cgaaattagg acattaagtc cattgatgct ctacaaaatc ttatgtgatt    300
actgaagtct gaagaagttt gtccaagtgt cgtttgtttg aagtcaaaaa taaagatgta    360
gcaggattat caagttctga tcattaaaag tcctattata atttctatgt ttcatcatca    420
ctttgaagtt cagttaatca aaagtacgat tcaagaatat tccagtactg tttctcgatc    480
cattattacc aaaaagttta kctaattatc ttcctggaaa cttcttctgt tccccccata    540
gagaaagttg tcctgccttt agttccagat taaataagat gagtatcaag tacccatatg    600
tattttcttc caaaatataa gaacataata tccaactata atttaagaaa aacaaagat    660
```

```
tagtggagaa cgttaaaaaa tactcttata taaaagttta atatatttta tgaatattta      720
aattttagtt ttttttaaaa aaaaagtctc aaaatcaatg acagagaggg tgacattaaa      780
ttaattaatc tttctttatt tggcctgaga tgcatgctgc ttataatagt tagttgcttc      840
cagaggaaac acatattcaa acagacaaga ttagctacga cagttgcctg gtaatatttt      900 ttatttt tattt aggcttcgtt tggaatgatt attataatt ggtatatgat agagagcttg      960
ggctgtgttc tcacattatt caaggtacat tctttctcac t                         1001
```

<210> SEQ ID NO 15
<211> LENGTH: 1001
<212> TYPE: DNA
<213> ORGANISM: Brassica napus

<400> SEQUENCE: 15

```
gatctttgtg aaggtggaa ggcgacctca ctgctgagga ggaagctaag gcgttggcga       60
tgggcgtggc gaaattagga cattaagtcc attgatgctc tacaaaatct tatgtgatta     120
ctgaagtctg aagaagtttg tccaagtgtc gtttgtttga agtcaaaaat aaagatgtag     180
caggattatc aagttctgat cattaaaagt cctattataa tttctatgtt tcatcatcac     240
tttgaagttc agttaatcaa aagtacgatt caagaatatt ccagtactgt ttctcgatcc     300
attattacca aaaagtttag ctaattatct tcctggaaac ttcttctgtt cccccccatag    360 agaaagttgt cctgcctta gttccagatt aaataagatg agtatcaagt acccatatgt      420
attttcttcc aaaatataag aacataatat ccaactataa tttaagaaaa aacaaagatt     480
agtggagaac gttaaaaaat rctcttatat aaaagtttaa tatattttat gaatatttaa     540
attttagttt tttttaaaaa aaaagtctca aaatcaatga cagagagggt gacattaaat     600
taattaatct ttctттtattт ggcctgagat gcatgctgct tataatagtt agttgcttcc    660
agaggaaaca catattcaaa cagacaagat tagctacgac agttgcctgg taatattttt    720
tattttatta ggcttcgttt ggaatgatta ttataatttg gtatatgata gagagcttgg    780
gctgtgttct cacattattc aaggtacatt ctttctcact ataattttct ttttacgtta     840
aattcaactc aaaaccaatt gctcaagtaa tactaatttc accattaatt ttgcaatatt     900
ttggtagcaa tcgacgagac caattttggg acgaatcggt ttattgatcg tattgcatgg     960
acaccatatt attttaggta aactttcaac gcaaaaccaa t                        1001
```

<210> SEQ ID NO 16
<211> LENGTH: 1001
<212> TYPE: DNA
<213> ORGANISM: Brassica napus

<400> SEQUENCE: 16

```
tgatcattaa aagtcctatt ataatттtcta tgtttcatca tcactttgaa gttcagttaa      60
tcaaaagtac gattcaagaa tattccagta ctgtttctcg atccattatt accaaaaagt     120

ttagctaatt atcttcctgg aaactt cttc тgттccccccc atagagaaag ttgtcctgcc    180

tttagttcca gatt aaataa gatgagtatc aagtacccat atgtatttt c ttccaaaata   240

taagaacata atatccaact ataatt taag aaaaacaaa gatt agtgga gaacgttaaa     300 aaatactctt atataaagt taatatatt ttatgaatat ttaaatttta gttttttta        360 aaaaaaagt ctcaaaatca atgacagaga gggtgacatt aaatt aatt а атcттт cтттт  420

atttggcctg agatgcatgc тgcтт атаат агтт агт т gc т tcc agagga aacacatatt  480
```

```
caaacagaca agattagcta ygacagttgc ctggtaatat ttttttatttt attaggcttc      540 gtttggaatg attattataa tttggtatat gatagagagc ttgggctgtg ttctcacatt      600
attcaaggta cattctttct cactataatt ttcttttttac gttaaattca actcaaaacc     660
aattgctcaa gtaatactaa tttcaccatt aattttgcaa tattttggta gcaatcgacg      720
agaccaattt tgggacgaat cggtttattg atcgtattgc atggacacca tattatttta     780
ggtaaacttt caacgcaaaa ccaatagacc ttaatgataa atcgtttcaa acttttgatt     840
taacttttca tttcagtgca aacgttatcg cttttagatt ccttgttaaa ctttcaggca    900
aataaactgg aagcagactc aaaacgataa ggaaagagct cgaagaacca actgaagtgg   960
aaagtgaact gaaacgaaga cttgaccagc taactaatca t                       1001
```

<210> SEQ ID NO 17
<211> LENGTH: 121
<212> TYPE: DNA
<213> ORGANISM: Brassica napus

<400> SEQUENCE: 17

```
tgcttataat agttagttgc ttccagaggr aacacatatt caaacagaca agattagcta      60
ygacagttgc ctggtaatat ttttttatttt attaggcttc gtttggaatg attattataa    120
t                                                                     121
```

<210> SEQ ID NO 18
<211> LENGTH: 1001
<212> TYPE: DNA
<213> ORGANISM: Brassica napus

<400> SEQUENCE: 18

```
gtattgcatg gacaccatat tattttaggt aaactttcaa cgcaaaacca atagacctta      60
atgataaatc gtttcaaact tttgatttaa cttttcattt cagtgcaaac gttatcgctt    120
ttagattcct tgttaaactt tcaggcaaat aaactggaag cagactcaaa acgataagga    180
aagagctcga agaaccaact gaagtggaaa gtgaactgaa acgaagactt gaccagctaa    240
ctaatcatct tactcaaaaa caatcccagg tatatgaata cttttaaata aaagagaatt    300
cagacaaaac taatatatata aa acttccaact ctcctgccaa atttaccaag tcgactttcc   360
tcataggaag caactctatc gtttagaatc catattttaa ctacttcaca ctattctctc    420
cataatctct ctctcataca aatacattga aggttttgac aacaaacaca aagctctaga    480
actcaagcag gagcaattga sactcttttca atctcaacta catactccag cgaagcagaa    540
ggcggtatct gaaaacccga ttcaagttca gcaccctctt ctccaaatcc taaagctggt    600
ggaacgatca ctctccttt acctccggcc ttcatcgacc tcagaacata atctacgcct    660
tcgcataatc ctttgctata tggctttgaa cccaccacaa gtgccaatgg cttcttattc     720
ttgtctttgc ttccaaatgt gtcaacaaac acttgtcccg tttcttgcac ttgtcccttc     780
atattaatca ctaccaaatc acctgctctt ggtgttgccc ctcctccaag ccgtagatca    840
tagtacctgc atagtttgat tcaatatagt ccaagacttg accgaagcta aggagaccca    900
ttgacaaaat gtacctaatg ccattgggca agacaatctc cttctcttct tcgacgtctc   960
tacaaacaca ccatacaaaa gcagttccaa agctttgtga g                      1001
```

<210> SEQ ID NO 19
<211> LENGTH: 1001
<212> TYPE: DNA
<213> ORGANISM: Brassica napus

<400> SEQUENCE: 19

```
atcatcttac tcaaaaacaa tcccaggtat atgaatactt ttaaataaaa gagaattcag      60
acaaaactaa tataaaaact tccaactctc ctgccaaatt taccaagtcg actttcctca     120
taggaagcaa ctctatcgtt tagaatccat attttaacta cttcacacta ttctctccat     180
aatctctctc tcatacaaat acattgaagg ttttgacaac aaacacaaag ctctagaact     240
caagcaggag caattgagac tctttcaatc tcaactacat actccagcga agcagaaggc     300
ggtatctgaa aacccgattc aagttcagca ccctcttctc caaatcctaa agctggtgga     360
acgatcactc tccttttacc tccggccttc atcgacctca aacataatc tacgccttcg      420
cataatcctt tgctatatgg ctttgaaccc accacaagtg ccaatggctt cttattcttg     480
tctttgcttc caaatgtgtc macaaacact tgtcccgttt cttgcacttg tcccttcata     540
ttaatcacta ccaaatcacc tgctcttggt gttgcccctc ctccaagccg tagatcatag     600
tacctgcata gtttgattca atatagtcca agacttgacc gaagctaagg agacccattg     660
acaaaatgta cctaatgcca ttgggcaaga caatctcctt ctcttcttcg acgtctctac     720
aaacacacca tacaaaagca gttccaaagc tttgtgagag tgatgacaac taagacagta     780
acttgaagct atggagatgt gaaaaccttg tgttagcttc ttcttgagaa acctcaagcc     840
gtgttttgat ctgctcggag atcacaccga aagctagaaa ccccgcccag gcaagacccg     900
caccgattcc aaaccgtctg gtcaaagaag aagcgaccca atccgtcgtc tcaacgctgg     960
tcttcttcct cttctgttgc gatgcgaggg gttgctccgt c                        1001
```

<210> SEQ ID NO 20
<211> LENGTH: 1001
<212> TYPE: DNA
<213> ORGANISM: Brassica napus

<400> SEQUENCE: 20

```
atgaatactt taaataaaa gagaattcag acaaaactaa tataaaaact tccaactctc       60
ctgccaaatt taccaagtcg actttcctca taggaagcaa ctctatcgtt tagaatccat     120
attttaacta cttcacacta ttctctccat aatctctctc tcatacaaat acattgaagg     180
ttttgacaac aaacacaaag ctctagaact caagcaggag caattgagac tctttcaatc     240
tcaactacat actccagcga agcagaaggc ggtatctgaa aacccgattc aagttcagca     300
ccctcttctc caaatcctaa agctggtgga acgatcactc tccttttacc tccggccttc     360
atcgacctca aacataatc tacgccttcg cataatcctt tgctatatgg ctttgaaccc      420
accacaagtg ccaatggctt cttattcttg tctttgcttc caaatgtgtc aacaaacact     480
tgtcccgttt cttgcacttg ycccttcata ttaatcacta ccaaatcacc tgctcttggt     540
gttgcccctc ctccaagccg tagatcatag tacctgcata gtttgattca atatagtcca     600
agacttgacc gaagctaagg agacccattg acaaaatgta cctaatgcca ttgggcaaga     660
caatctcctt ctcttcttcg acgtctctac aaacacacca tacaaaagca gttccaaagc     720
tttgtgagag tgatgacaac taagacagta acttgaagct atggagatgt gaaaaccttg     780
tgttagcttc ttcttgagaa acctcaagcc gtgttttgat ctgctcggag atcacaccga     840
aagctagaaa ccccgcccag gcaagacccg caccgattcc aaaccgtctg gtcaaagaag     900
aagcgaccca atccgtcgtc tcaacgctgg tcttcttcct cttctgttgc gatgcgaggg     960
gttgctccgt ctttacggat tgagtcggag tagaagaaga c                        1001
```

<210> SEQ ID NO 21
<211> LENGTH: 1001
<212> TYPE: DNA
<213> ORGANISM: Brassica napus

<400> SEQUENCE: 21

| | | | | | | |
|---|---|---|---|---|---|---|
| tcaaagaaga | agcgacccaa | tccgtcgtct | caacgctggt | cttcttcctc | ttctgttgcg | 60 |
| atgcgagggg | ttgctccgtc | tttacggatt | gagtcggagt | agaagaagac | tctggctgag | 120 |
| aaggagggtt | ctgctccgga | ggagtggaag | aagaggcgca | acagaggtga | tacggcgccg | 180 |
| tcttcgtgaa | cggctttgaa | aggaacggag | ctgtaacggt | gaatagattc | gccatttcgg | 240 |
| cataaaataa | aataaaaacc | tcagctttat | tataagtata | taaacgctta | tcctgttcgt | 300 |
| gtgattcatt | ttaaagacag | aagtcaagcc | aagttcttgt | cactgtcagt | gataaaccga | 360 |
| atccggttag | gctaaaccgg | gtcgtcgaaa | ttattaaaaa | aaattaaatt | gtttcttctt | 420 |
| cttcttctcc | tttctctctc | caatcagtta | ggaagaaggt | cgtgacccac | tccgaaggac | 480 |
| aaaaccgaga | gacgatccga | kaaataaggt | gaatttgacg | agaatcatta | ggctgagaag | 540 |
| gaaactcgga | gacccaaaat | cgtaaatcac | caatctttaa | tctgttttc | taattcagta | 600 |
| gtagtagttg | atgggtggtg | gtgggaatct | cgtcgacggt | gttcgtcgtt | ggcttttca | 660 |
| acgaccctct | tcttccaata | ataatcctca | cgaacccatt | gttccaaagt | ctgatacttt | 720 |
| ttctattccc | catcatcaat | ctgagcttat | cattaccgaa | gatctcgatt | tctctggtct | 780 |
| caagcttatc | aaagttccca | acgtcatca | cttacccatg | gatcctcaaa | agaaggtacc | 840 |
| ttttggcgcg | atcactgatt | gtgtagacat | catttgatct | gtgatctttg | tttgattgaa | 900 |
| gtttacttct | attaatgttt | tgtacattgt | tcaacaagta | gctagatttt | gattaggcct | 960 |
| tttatagggt | gttattgatt | attgatttat | ttatttattt | g | | 1001 |

<210> SEQ ID NO 22
<211> LENGTH: 1001
<212> TYPE: DNA
<213> ORGANISM: Brassica napus

<400> SEQUENCE: 22

| | | | | | | |
|---|---|---|---|---|---|---|
| attaggctga | gaaggaaact | cggagaccca | aaatcgtaaa | tcaccaatct | ttaatctgtt | 60 |
| tttctaattc | agtagtagta | gttgatgggt | ggtggtggga | atctcgtcga | cggtgttcgt | 120 |
| cgttggcttt | ttcaacgacc | ctcttcttcc | aataataatc | ctcacgaacc | cattgttcca | 180 |
| aagtctgata | cttttctat | tccccatcat | caatctgagc | ttatcattac | cgaagatctc | 240 |
| gatttctctg | gtctcaagct | tatcaaagtt | cccaaacgtc | atcacttacc | catggatcct | 300 |
| caaaagaagg | tacctttgg | cgcgatcact | gattgtgtag | acatcatttg | atctgtgatc | 360 |
| tttgttgat | tgaagtttac | ttctattaat | gttttgtaca | ttgttcaaca | agtagctaga | 420 |
| ttttgattag | gcctttata | gggtgttatt | gattattgat | ttatttattt | atttgattgg | 480 |
| atcctactgt | ttgttcaggg | ygtgcaggaa | aaggacttct | tcacggagta | cggagaagca | 540 |
| aacaggtacc | aggttcaaga | agtcgttggt | aaaggaagct | acggtgttgt | ggcctctgct | 600 |
| ctagacacac | acactggcga | aagagttgct | atcaagaaga | tcaacgacgt | ctttgagcat | 660 |
| gtctctgatg | caaccaggat | tctcagggag | atcaagctgc | tgaggttgct | taagcatccg | 720 |
| gatgttgtgg | agattaagca | tattatgctg | cctccttctc | gtagagagtt | cagggatatt | 780 |
| tacgttgtgt | tgagctgat | ggagtctgat | cttcatcagg | tgattaaggc | gaatgatgat | 840 |
| ttgactcctg | atcattatca | gttcttcttg | tatcagcttc | tccgtggtct | caaatatgtc | 900 |

```
cacgcaggtt aagtttctgg ttttaaaaca gtcttctctt ttgtctgtct ttattgaaac    960
gtttgtgtgt tttcagctaa tgtgtttcat cgggatttga a                        1001
```

<210> SEQ ID NO 23
<211> LENGTH: 1001
<212> TYPE: DNA
<213> ORGANISM: Brassica napus

<400> SEQUENCE: 23

```
gacccaaaat cgtaaatcac caatctttaa tctgtttttc taattcagta gtagtagttg     60
atgggtggtg gtgggaatct cgtcgacggt gttcgtcgtt ggcttttttca acgaccctct   120
tcttccaata ataatcctca cgaacccatt gttccaaagt ctgatacttt ttctattccc    180
catcatcaat ctgagcttat cattaccgaa gatctcgatt tctctggtct caagcttatc    240
aaagttccca aacgtcatca cttacccatg gatcctcaaa agaaggtacc ttttggcgcg    300
atcactgatt gtgtagacat catttgatct gtgatctttg tttgattgaa gtttacttct    360
attaatgttt tgtacattgt tcaacaagta gctagatttt gattaggcct tttataggt    420
gttattgatt attgatttat ttatttattt gattggatcc tactgtttgt tcagggtgtg    480
caggaaaagg acttcttcac rgagtacgga gaagcaaaca ggtaccaggt tcaagaagtc    540
gttggtaaag gaagctacgg tgttgtggcc tctgctctag acacacacac tggcgaaaga    600
gttgctatca agaagatcaa cgacgtcttt gagcatgtct ctgatgcaac caggattctc    660
agggagatca agctgctgag gttgcttaag catccggatg ttgtggagat taagcatatt    720
atgctgcctc cttctcgtag agagttcagg gatatttacg ttgtgtttga gctgatggag    780
tctgatcttc atcaggtgat taaggcgaat gatgatttga ctcctgatca ttatcagttc    840
ttcttgtatc agcttctccg tggtctcaaa tatgtccacg caggttaagt ttctggtttt    900
aaaacagtct tctctttgt ctgtctttat tgaaacgttt gtgtgttttc agctaatgtg    960
tttcatcggg atttgaaacc aagaacatt ctagctaatg c                        1001
```

<210> SEQ ID NO 24
<211> LENGTH: 1001
<212> TYPE: DNA
<213> ORGANISM: Brassica napus

<400> SEQUENCE: 24

```
tttcaacgac cctcttcttc caataataat cctcacgaac ccattgttcc aaagtctgat     60
acttttctcta ttccccatca tcaatctgag cttatcatta ccgaagatct cgatttctct   120
ggtctcaagc ttatcaaagt tcccaaacgt catcacttac ccatggatcc tcaaaagaag    180
gtaccttttg gcgcgatcac tgattgtgta gacatcattt gatctgtgat ctttgtttga    240
ttgaagttta cttctattaa tgttttgtac attgttcaac aagtagctag attttgatta    300
ggcctttat agggtgttat tgattattga tttatttatt tatttgattg gatcctactg    360
tttgttcagg gtgtgcagga aaaggacttc ttcacggagt acggagaagc aaacaggtac    420
caggttcaag aagtcgttgg taaggaagc tacggtgttg tggcctctgc tctagacaca    480
cacactggcg aaagagttgc yatcaagaag atcaacgacg tctttgagca tgtctctgat    540
gcaaccagga ttctcaggga gatcaagctg ctgaggttgc ttaagcatcc ggatgttgtg    600
gagattaagc atattatgct gcctccttct cgtagagagt tcaggatat ttacgttgtg    660
tttgagctga tggagtctga tcttcatcag gtgattaagg cgaatgatga tttgactcct    720
```

| | |
|---|---|
| gatcattatc agttcttctt gtatcagctt ctccgtggtc tcaaatatgt ccacgcaggt | 780 |
| taagtttctg gttttaaaac agtcttctct tttgtctgtc tttattgaaa cgtttgtgtg | 840 |
| ttttcagcta atgtgtttca tcgggatttg aaaccaaaga acattctagc taatgctgat | 900 |
| tgcaagttga agatctgtga ttttggactc gctcgtgtct cttttaacga cgcaccaact | 960 |
| gctatattct ggactgtgag tcctctaatt tgaatgcagc a | 1001 |

<210> SEQ ID NO 25
<211> LENGTH: 1001
<212> TYPE: DNA
<213> ORGANISM: Brassica napus

<400> SEQUENCE: 25

| | |
|---|---|
| cccattgttc caaagtctga tacttttttct attccccatc atcaatctga gcttatcatt | 60 |
| accgaagatc tcgatttctc tggtctcaag cttatcaaag ttcccaaacg tcatcactta | 120 |
| cccatggatc ctcaaaagaa ggtaccttt ggcgcgatca ctgattgtgt agacatcatt | 180 |
| tgatctgtga tctttgtttg attgaagttt acttctatta atgttttgta cattgttcaa | 240 |
| caagtagcta gattttgatt aggccttta tagggtgtta ttgattattg atttattat | 300 |
| ttatttgatt ggatcctact gtttgttcag ggtgtgcagg aaaaggactt cttcacggag | 360 |
| tacggagaag caaacaggta ccaggttcaa gaagtcgttg gtaaaggaag ctacggtgtt | 420 |
| gtggcctctg ctctagacac acacactggc gaaagagttg ctatcaagaa gatcaacgac | 480 |
| gtctttgagc atgtctctga ygcaaccagg attctcaggg agatcaagct gctgaggttg | 540 |
| cttaagcatc cggatgttgt ggagattaag catattatgc tgcctcctc tcgtagagag | 600 |
| ttcaggata tttacgttgt gtttgagctg atggagtctg atcttcatca ggtgattaag | 660 |
| gcgaatgatg atttgactcc tgatcattat cagttcttct gtatcagct ctccgtggt | 720 |
| ctcaaatatg tccacgcagg ttaagtttct ggttttaaaa cagtcttctc ttttgtctgt | 780 |
| ctttattgaa acgtttgtgt gttttcagct aatgtgtttc atcgggattt gaaaccaaag | 840 |
| aacattctag ctaatgctga ttgcaagttg aagatctgtg attttggact cgctcgtgtc | 900 |
| tcttttaacg acgcaccaac tgctatattc tggactgtga gtcctctaat ttgaatgcag | 960 |
| cagagcttct cattaaactg tttgtgaact cactctttta t | 1001 |

<210> SEQ ID NO 26
<211> LENGTH: 1001
<212> TYPE: DNA
<213> ORGANISM: Brassica napus

<400> SEQUENCE: 26

| | |
|---|---|
| ttacccatgg atcctcaaaa gaaggtacct tttggcgcga tcactgattg tgtagacatc | 60 |
| atttgatctg tgatctttgt tgattgaag tttacttcta ttaatgtttt gtacattgtt | 120 |
| caacaagtag ctagattttg attaggcctt ttatagggtg ttattgatta ttgatttatt | 180 |
| tatttatttg attggatcct actgtttgtt cagggtgtgc aggaaaagga cttcttcacg | 240 |
| gagtacggag aagcaaacag gtaccaggtt caagaagtcg ttggtaaagg aagctacggt | 300 |
| gttgtggcct ctgctctaga cacacacact ggcgaaagag ttgctatcaa gaagatcaac | 360 |
| gacgtctttg agcatgtctc tgatgcaacc aggattctca gggagatcaa gctgctgagg | 420 |
| ttgcttaagc atccggatgt tgtggagatt aagcatatta tgctgcctcc ttctcgtaga | 480 |
| gagttcaggg atatttacgt ygtgtttgag ctgatggagt ctgatcttca tcaggtgatt | 540 |
| aaggcgaatg atgatttgac tcctgatcat tatcagttct tcttgtatca gcttctccgt | 600 |

```
ggtctcaaat atgtccacgc aggttaagtt tctggtttta aaacagtctt ctcttttgtc    660
tgtctttatt gaaacgtttg tgtgttttca gctaatgtgt ttcatcggga tttgaaacca    720
aagaacattc tagctaatgc tgattgcaag ttgaagatct gtgattttgg actcgctcgt    780
gtctctttta acgacgcacc aactgctata ttctggactg tgagtcctct aatttgaatg    840
cagcagagct tctcattaaa ctgtttgtga actcactctt ttatctatgt tttgtaggat    900
tatgtagcta ctcggtggta ccgtgcccct gaactctgtg gatcgttttt ctccaaagta    960
agattctttt tttttgttta ttcactgaac ctctctgtat c                      1001
```

<210> SEQ ID NO 27
<211> LENGTH: 1001
<212> TYPE: DNA
<213> ORGANISM: Brassica napus

<400> SEQUENCE: 27

```
aaaacagtct tctcttttgt ctgtctttat tgaaacgttt gtgtgttttc agctaatgtg     60
tttcatcggg atttgaaacc aaagaacatt ctagctaatg ctgattgcaa gttgaagatc    120
tgtgattttg gactcgctcg tgtctctttt aacgacgcac caactgctat attctggact    180
gtgagtcctc taatttgaat gcagcagagc ttctcattaa actgtttgtg aactcactct    240
tttatctatg ttttgtagga ttatgtagct actcggtggt accgtgcccc tgaactctgt    300
ggatcgtttt tctccaaagt aagattcttt tttttgttt attcactgaa cctctctgta    360
tcacaagaac ggacttcttg atctaggtcc tatattttca taagatatac cgtctaatgc    420
taagttaact ttcagtacac tcctgcgatt gatatatgga gtgttggttg cattttttgcg    480 gaaatgatat tgggaaagcc wttgtttccc gggaagaacg tggtgcacca acttgatctt    540
atgactgact ttcttggcac tcctccgcct gagtccatat caagggttag tcactcaaac    600
atgtgttaca ttcccatcat ttgagagcta gttaatgagt ttttttttgtt ttttttttgca    660 atcttgaaat tatgacagat aagaaatgaa aaggcgagga gatatctaag cagcatgagg    720
aagaaacagc cggttccttt ctctcacaag ttccctaaag ctgatccttt ggctctccgc    780
cttctcgaac gccttattgc ctttgatcct aaagatcgtg tctcagctga agatgtaagc    840
gacaagcaac tttcattttt tttttaatta caaagactta aaactctcaa gttcattatt    900
ctgatttggt tatttacagg cactagctga tccttatttc agtggtctgt caaactcaga    960
gcgtgaacca tcaacgcagc caatctcaaa gcttgagttt g                      1001
```

<210> SEQ ID NO 28
<211> LENGTH: 1002
<212> TYPE: DNA
<213> ORGANISM: Brassica napus
<220> FEATURE:
<221> NAME/KEY: misc_feature
<222> LOCATION: (502)..(502)
<223> OTHER INFORMATION: where n is an insertion/deletion [+/TT]

<400> SEQUENCE: 28

```
ttttggactc gctcgtgtct cttttaacga cgcaccaact gctatattct ggactgtgag     60
tcctctaatt tgaatgcagc agagcttctc attaaactgt ttgtgaactc actcttttat    120
ctatgttttg taggattatg tagctactcg gtggtaccgt gcccctgaac tctgtggatc    180 gttttttctcc aaagtaagat tcttttttttt tgttttattca ctgaacctct ctgtatcaca    240
agaacggact tcttgatcta ggtcctatat tttcataaga tataccgtct aatgctaagt    300
```

```
taactttcag tacactcctg cgattgatat atggagtgtt ggttgcattt ttgcggaaat      360
gatattggga aagcctttgt ttcccgggaa gaacgtggtg caccaacttg atcttatgac      420
tgactttctt ggcactcctc cgcctgagtc catatcaagg gttagtcact caaacatgtg      480
ttacattccc atcatttgag angctagtta atgagttttt tttgttttttt tttgcaatct      540 tgaaattatg acagataaga aatgaaaagg cgaggagata tctaagcagc atgaggaaga      600
aacagccggt tcctttctct cacaagttcc ctaaagctga tcctttggct ctccgccttc      660
tcgaacgcct tattgccttt gatcctaaag atcgtgtctc agctgaagat gtaagcgaca      720
agcaactttc attttttttt taattacaaa gacttaaaac tctcaagttc attattctga      780
tttggttatt tacaggcact agctgatcct tatttcagtg gtctgtcaaa ctcagagcgt      840
gaaccatcaa cgcagccaat ctcaaagctt gagtttgatt ttgagagaaa gaagttgaac      900
aaagatgacg tcagagaatt aatctaccga gaggtaacac aaaaaaaaat gcttttgact      960
atgtcttatt gttctcttca ttgatctaac attcacttta tc                       1002

<210> SEQ ID NO 29
<211> LENGTH: 1001
<212> TYPE: DNA
<213> ORGANISM: Brassica napus

<400> SEQUENCE: 29
ttggactcgc tcgtgtctct tttaacgacg caccaactgc tatattctgg actgtgagtc       60
ctctaatttg aatgcagcag agcttctcat taaactgttt gtgaactcac tcttttatct      120
atgttttgta ggattatgta gctactcggt ggtaccgtgc ccctgaactc tgtggatcgt      180
ttttctccaa agtaagattc tttttttttg tttattcact gaacctctct gtatcacaag      240
aacggacttc ttgatctagg tcctatattt tcataagata taccgtctaa tgctaagtta      300
actttcagta cactcctgcg attgatatat ggagtgttgg ttgcattttt gcggaaatga      360
tattgggaaa gcctttgttt cccgggaaga acgtggtgca ccaacttgat cttatgactg      420
actttcttgg cactcctccg cctgagtcca tatcaagggt tagtcactca aacatgtgtt      480
acattcccat catttgagag ytagttaatg agttttttttt gttttttttt gcaatcttga      540
aattatgaca gataagaaat gaaaaggcga ggagatatct aagcagcatg aggaagaaac      600
agccggttcc tttctctcac aagttcccta aagctgatcc tttggctctc cgccttctcg      660
aacgccttat tgcctttgat cctaaagatc gtgtctcagc tgaagatgta agcgacaagc      720
aactttcatt ttttttttaa ttacaaagac ttaaaactct caagttcatt attctgatt     780 ggttatttac aggcactagc tgatccttat ttcagtggtc tgtcaaactc agagcgtgaa      840
ccatcaacgc agccaatctc aaagcttgag tttgattttg agagaaagaa gttgaacaaa      900
gatgacgtca gagaattaat ctaccgagag gtaacacaaa aaaaatgct tttgactatg      960 tcttattgtt ctcttcattg atctaacatt cactttatct t                       1001

<210> SEQ ID NO 30
<211> LENGTH: 1001
<212> TYPE: DNA
<213> ORGANISM: Brassica napus

<400> SEQUENCE: 30
agtacactcc tgcgattgat atatggagtg ttggttgcat ttttgcggaa atgatatttgg       60 gaaagccttt gtttcccggg aagaacgtgg tgcaccaact tgatcttatg actgactttc      120
ttggcactcc tccgcctgag tccatatcaa gggttagtca ctcaaacatg tgttacattc      180
```

```
ccatcatttg agagctagtt aatgagtttt ttttgttttt ttttgcaatc ttgaaattat      240
gacagataag aaatgaaaag gcgaggagat atctaagcag catgaggaag aaacagccgg      300
ttcctttctc tcacaagttc cctaaagctg atcctttggc tctccgcctt ctcgaacgcc      360
ttattgcctt tgatcctaaa gatcgtgtct cagctgaaga gtaagcgac aagcaacttt       420 cattttttt ttaattacaa agacttaaaa ctctcaagtt cattattctg atttggttat       480
ttacaggcac tagctgatcc wtatttcagt ggtctgtcaa actcagagcg tgaaccatca      540
acgcagccaa tctcaaagct tgagtttgat tttgagagaa agaagttgaa caaagatgac      600
gtcagagaat taatctaccg agaggtaaca caaaaaaaaa tgcttttgac tatgtcttat      660
tgttctcttc attgatctaa cattcacttt atctttggga aaaacattta gatattggag      720
tatcatcctc agatgctgga ggagtacaag cgcggtggtg atcagctcag cttcatgtac      780
cctaggttag ctaattaaac acctcatgaa ctataattcc ctgaaaacag aatgaaacca      840
agaactcttc tgttgtttac gcagtggggt tgatcggttc aagaggcagt ttgctcacct      900
tgaagagaat caaggtaaac caggagcagg ggcaggagga ggaagaagta ctgcaatgca      960
tagacaccat gcttccttgc caatgtaatg tcttttcac a                          1001

<210> SEQ ID NO 31
<211> LENGTH: 1001
<212> TYPE: DNA
<213> ORGANISM: Brassica napus

<400> SEQUENCE: 31
acactcctgc gattgatata tggagtgttg gttgcatttt tgcggaaatg atattgggaa       60
agcctttgtt tcccgggaag aacgtggtgc accaacttga tcttatgact gactttcttg      120
gcactcctcc gcctgagtcc atatcaaggg ttagtcactc aaacatgtgt tacattccca      180
tcatttgaga gctagttaat gagtttttt tgtttttttt tgcaatcttg aaattatgac       240
agataagaaa tgaaaaggcg aggagatatc taagcagcat gaggaagaaa cagccggttc      300 cttctctca caagttccct aaagctgatc ctttggctct ccgccttctc gaacgcctta      360
ttgcctttga tcctaaagat cgtgtctcag ctgaagatgt aagcgacaag caactttcat      420 tttttttta attacaaaga cttaaaactc tcaagttcat tattctgatt tggttattta      480
caggcactag ctgatcctta yttcagtggt ctgtcaaact cagagcgtga accatcaacg      540
cagccaatct caaagcttga gtttgatttt gagagaaaga gttgaacaa agatgacgtc      600 agagaattaa tctaccgaga ggtaacacaa aaaaaatgc ttttgactat gtcttattgt       660
tctcttcatt gatctaacat tcactttatc tttgggaaaa acatttagat attggagtat      720
catcctcaga tgctggagga gtacaagcgc ggtggtgatc agctcagctt catgtaccct      780
aggttagcta attaaacacc tcatgaacta taattccctg aaaacagaat gaaaccaaga      840
actcttctgt tgtttacgca gtggggttga tcggttcaag aggcagtttg ctcaccttga      900
agagaatcaa ggtaaaccag gagcaggggc aggaggagga agaagtactg caatgcatag      960
acaccatgct tccttgccaa tgtaatgtct ttttcacaga a                         1001

<210> SEQ ID NO 32
<211> LENGTH: 1002
<212> TYPE: DNA
<213> ORGANISM: Brassica napus
<220> FEATURE:
<221> NAME/KEY: misc_feature
<222> LOCATION: (502)..(502)
```

<223> OTHER INFORMATION: where n is an insertion/deletion [+/A]

<400> SEQUENCE: 32

```
gtccatatca agggttagtc actcaaacat gtgttacatt cccatcattt gagagctagt      60
taatgagttt ttttttgtttt ttttttgcaat cttgaaatta tgacagataa gaaatgaaaa   120
ggcgaggaga tatctaagca gcatgaggaa gaaacagccg gttcctttct ctcacaagtt    180
ccctaaaagct gatcctttgg ctctccgcct tctcgaacgc ttattgcct ttgatcctaa     240
agatcgtgtc tcagctgaag atgtaagcga caagcaactt tcatttttt tttaattaca    300
aagacttaaa actctcaagt tcattattct gatttggtta tttacaggca ctagctgatc    360
cttatttcag tggtctgtca aactcagagc gtgaaccatc aacgcagcca atctcaaagc    420
ttgagtttga ttttgagaga aagaagttga acaaagatga cgtcagagaa ttaatctacc    480
gagaggtaac acaaaaaaaa antgcttttg actatgtctt attgttctct tcattgatct    540
aacattcact ttatctttgg gaaaaacatt tagatattgg agtatcatcc tcagatgctg    600
gaggagtaca agcgcggtgg tgatcagctc agcttcatgt accctaggtt agctaattaa    660
acacctcatg aactataatt ccctgaaaac agaatgaaac caagaactct tctgttgttt    720
acgcagtggg gttgatcggt tcaagaggca gtttgctcac cttgaagaga atcaaggtaa    780
accaggagca ggggcaggag gaggaagaag tactgcaatg catagacacc atgcttcctt    840
gccaatgtaa tgtcttttc acagaatctc ttgctttgct ctctcttct ctgaaagcgt     900
tgggcttctt tgtgattgtg tgttgcagag agagagttcc tgctcagagt ggtcagactg    960
tagaagaaag cagtgatgtt gagagaagag cagcagctgc tg                      1002
```

<210> SEQ ID NO 33
<211> LENGTH: 1001
<212> TYPE: DNA
<213> ORGANISM: Brassica napus

<400> SEQUENCE: 33

```
ctagctgatc cttatttcag tggtctgtca aactcagagc gtgaaccatc aacgcagcca      60
atctcaaagc ttgagtttga ttttgagaga aagaagttga acaaagatga cgtcagagaa   120
ttaatctacc gagaggtaac acaaaaaaaa atgcttttga ctatgtctta ttgttctctt    180
cattgatcta acattcactt tatctttggg aaaaacattt agatattgga gtatcatcct    240
cagatgctgg aggagtacaa gcgcggtggt gatcagctca gcttcatgta ccctaggtta    300
gctaattaaa cacctcatga actataattc cctgaaaaca gaatgaaacc aagaactctt    360
ctgttgttta cgcagtgggg ttgatcggtt caagaggcag tttgctcacc ttgaagagaa    420
tcaaggtaaa ccaggagcag gggcaggagg aggaagaagt actgcaatgc atagacacca    480
tgcttccttg ccaatgtaat rtcttttttca gaatctctg ctttgctc tctctttctc     540
tgaaagcgtt gggcttcttt tgtgattgtgt gttgcagaga gagagttcct gctcagagtg    600
gtcagactgt agaagaaagc agtgatgttg agagaagagc agcagctgct gtggcttcaa    660
ctttggaatc tgaggaagca gacaatggag gaggttacag tgctcgtagc ctcatgaaga    720
gttcgagcat cagtggttct aaatgcatcg gtgtccaatc taaaaccgac aaagaggtta    780
gttagttagt tagttagtgg agttaaaaaaa acagaggatc ttgaaaggaa catggagatg    840
gagtttgctt acttactgtt gtttctgttc tgtgttgtag acaccatag ctgaggaagg    900
agatgatgaa tcagtggcgg agcttactga tagagttgct tctcttcgta attcttaaaa    960
cgttttgttt tttttttttg gcgtttggtg aaagctttct g                       1001
```

<210> SEQ ID NO 34
<211> LENGTH: 1001
<212> TYPE: DNA
<213> ORGANISM: Brassica napus
<220> FEATURE:
<221> NAME/KEY: misc_feature
<222> LOCATION: (501)..(501)
<223> OTHER INFORMATION: where n is an insertion/deletion [-/T]

<400> SEQUENCE: 34

```
atccttattt cagtggtctg tcaaactcag agcgtgaacc atcaacgcag ccaatctcaa      60
agcttgagtt tgattttgag agaaagaagt tgaacaaaga tgacgtcaga gaattaatct     120
accgagaggt aacacaaaaa aaaatgcttt tgactatgtc ttattgttct cttcattgat     180
ctaacattca ctttatcttt gggaaaaaca tttagatatt ggagtatcat cctcagatgc     240
tggaggagta caagcgcggt ggtgatcagc tcagcttcat gtaccctagg ttagctaatt     300
aaacacctca tgaactataa ttccctgaaa acagaatgaa accaagaact cttctgttgt     360
ttacgcagtg gggttgatcg gttcaagagg cagtttgctc accttgaaga gaatcaaggt     420
aaaccaggag caggggcagg aggaggaaga agtactgcaa tgcatagaca ccatgcttcc     480
ttgccaatgt aatgtctttt ncacagaatc tcttgctttg ctctctcttt ctctgaaagc     540
gttgggcttc tttgtgattg tgtgttgcag agagagagtt cctgtcaga gtggtcagac      600
tgtagaagaa agcagtgatg ttgagagaag agcagcagct gctgtggctt caactttgga     660
atctgaggaa gcagacaatg gaggaggtta cagtgctcgt agcctcatga agagttcgag     720
catcagtggt tctaaatgca tcggtgtcca atctaaaacc gacaaagagg ttagttagtt     780
agttagttag tggagttaaa aaaacagagg atcttgaaag gaacatggag atggagtttg     840
cttacttact gttgtttctg ttctgtgttg taggacacca tagctgagga aggagatgat     900
gaatcagtgg cggagcttac tgatagagtt gcttctcttc gtaattctta aaacgttttt     960
gttttttttt ttggcgtttg gtgaaagctt tctggtgaaa a                       1001
```

<210> SEQ ID NO 35
<211> LENGTH: 1001
<212> TYPE: DNA
<213> ORGANISM: Brassica napus

<400> SEQUENCE: 35

```
acgtcagaga attaatctac cgagaggtaa cacaaaaaaa aatgcttttg actatgtctt      60
attgttctct tcattgatct aacattcact ttatctttgg gaaaaacatt tagatattgg     120
agtatcatcc tcagatgctg gaggagtaca agcgcggtgg tgatcagctc agcttcatgt     180
accctaggtt agctaattaa cacctcatg aactataatt ccctgaaaac agaatgaaac      240
caagaactct tctgttgttt acgcagtggg gttgatcggt tcaagaggca gtttgctcac     300
cttgaagaga atcaaggtaa accaggagca ggggcaggag gaggaagaag tactgcaatg     360
catagacacc atgcttcctt gccaatgtaa tgtctttttc acagaatctc ttgctttgct     420
ctctctttct ctgaaagcgt tgggcttctt tgtgattgtg tgttgcagag agagagttcc     480
tgctcagagt ggtcagactg yagaagaaag cagtgatgtt gagagaagag cagcagctgc     540
tgtggcttca actttggaat ctgaggaagc agacaatgga ggaggttaca gtgctcgtag     600
cctcatgaag agttcgagca tcagtggttc taaatgcatc ggtgtccaat ctaaaaccga     660
caaagaggtt agttagttag ttagttagtg gagttaaaaa aacagaggat cttgaaagga     720
```

| | |
|---|---:|
| acatggagat ggagtttgct tacttactgt tgtttctgtt ctgtgttgta ggacaccata | 780 |
| gctgaggaag gagatgatga atcagtggcg gagcttactg atagagttgc ttctcttcgt | 840 |
| aattcttaaa acgtttttgt tttttttttt ggcgtttggt gaaagctttc tggtgaaaat | 900 |
| tggtttctac attttatttt cacttcttcc acatctatct tcgtggttgg gtttgatttg | 960 |
| ttggatttaa tagtttgggg gcgagaatga gacctttta a | 1001 |

<210> SEQ ID NO 36
<211> LENGTH: 1001
<212> TYPE: DNA
<213> ORGANISM: Brassica napus

<400> SEQUENCE: 36

| | |
|---|---:|
| acgcagtggg gttgatcggt tcaagaggca gtttgctcac cttgaagaga atcaaggtaa | 60 |
| accaggagca ggggcaggag gaggaagaag tactgcaatg catagacacc atgcttcctt | 120 |
| gccaatgtaa tgtcttttc acagaatctc ttgctttgct ctctcttct ctgaaagcgt | 180 |
| tgggcttctt tgtgattgtg tgttgcagag agagagttcc tgctcagagt ggtcagactg | 240 |
| tagaagaaag cagtgatgtt gagagaagag cagcagctgc tgtggcttca actttggaat | 300 |
| ctgaggaagc agacaatgga ggaggttaca gtgctcgtag cctcatgaag agttcgagca | 360 |
| tcagtggttc taaatgcatc ggtgtccaat ctaaaaccga caaagaggtt agttagttag | 420 |
| ttagttagtg gagttaaaaa aacagaggat cttgaaagga acatggagat ggagtttgct | 480 |
| tacttactgt tgtttctgtt ytgtgttgta ggacaccata gctgaggaag gagatgatga | 540 |
| atcagtggcg gagcttactg atagagttgc ttctcttcgt aattcttaaa acgtttttgt | 600 |
| tttttttttt ggcgtttggt gaaagctttc tggtgaaaat tggtttctac attttatttt | 660 |
| cacttcttcc acatctatct tcgtggttgg gtttgatttg ttggatttaa tagtttgggg | 720 |
| gcgagaatga gacctttta ataagaacat ctatctccat gtaatttctt ttatccttt | 780 |
| ctataaattg ttctttcaat cttttttaccg attcagtttg cttaagtaca tcatgaaatc | 840 |
| agaattaaac taaaaatag tatactaaaa aaggaaaaca tccaaaaaac ctttatagtt | 900 |
| gaagtaaaca tatatatata tatatatata tatatgcagt ttgctttata ttatgatctg | 960 |
| aattagttat atatacatac taagtgtttt tcaaaaatag t | 1001 |

<210> SEQ ID NO 37
<211> LENGTH: 1001
<212> TYPE: DNA
<213> ORGANISM: Brassica napus

<400> SEQUENCE: 37

| | |
|---|---:|
| agataccacc ttcaccggtt gaaaacaagt tttgcgagaa tcacgttcga gtaaaatta | 60 |
| tgcacttcat ttaaatatta caagtgttta tttattcgac tataaatgtt cgtaaagacc | 120 |
| acaattcatt tgaagattta ttttattttt cactctcata aaatcctttt gtattcacca | 180 |
| gggtcatcaa tatacataca ctcatctgat ttatatagtt gcatggcagt taattgcaat | 240 |
| ttagtcctag gtgatttgtt ctattataaa tcaaaccaag agagttgcat gttttccatg | 300 |
| acgaagtatc ttctactagt agattactgg cagttggtgt aatagttacc accagtagaa | 360 |
| actagtttac caacgagtac aacgaggatc atccacgtgc aaggagtgat cctcgtaact | 420 |
| gacggcagga atgatgtaac gtggcaggac gaaccaaagg gatcgtgggt aacagctgag | 480 |
| accgtgatac ggcacgtgtc wtgtttgtgg atgaaaagaa gtgtgaaatg gcctatgcat | 540 |
| ggtctatagg ttacactaat ctgaccaaaa gcttctttta acctttcct tttgtttctt | 600 |

```
ctttcgctta taaccaagtg agaaactgta ttgtatttcc ctgaaaacat tagattaagt    660
atgagggatt acatatactt aaggcatctt taaccttagt ttatttatga taaagttagt    720
ttcagagtaa tatagcatta ttagctttga tggtttgtac aatagtgatg aatttggaca    780
tgaccataaa ctacaagaca cgagtggatt ctcataatat ttgcaccact aaggacaaaa    840
taactcatca tgctactttg ttgaaatata ttaccattat tattaatgta ttataaaaat    900
acgaacaagt tattattgaa ttgggtttac agctttcaag atatatttta tataaaaatg    960
aaaataaaaa caagaatttg tttacatata aaaagcaaac a                        1001
```

<210> SEQ ID NO 38
<211> LENGTH: 1001
<212> TYPE: DNA
<213> ORGANISM: Brassica napus

<400> SEQUENCE: 38

```
gatgaaaaga agtgtgaaat ggcctatgca tggtctatag gttacactaa tctgaccaaa     60
agcttctttt aaccttttcc ttttgtttct tctttcgctt ataaccaagt gagaaactgt    120
attgtatttc cctgaaaaca ttagattaag tatgagggat tacatatact taaggcatct    180
ttaaccttag tttatttatg ataaagttag tttcagagta atatagcatt attagctttg    240
atggtttgta caatagtgat gaatttggac atgaccataa actacaagac acgagtggat    300
tctcataata tttgcaccac taaggacaaa ataactcatc atgctacttt gttgaaatat    360
attaccatta ttattaatgt attataaaaa tacgaacaag ttattattga attgggttta    420
cagctttcaa gatatatttt atataaaaat gaaaataaaa acaagaattt gtttacatat    480
aaaaagcaaa cacgcatgta waataaattg gactgcatgt aaatcattgt tcaaattcat    540
tgtatttgtc gatggattaa ttaaatatct ttttgctata aaataaaatt ttatctttta    600
accaaaaaaa ataaaaaaaa taaaaaaaaa taaaattttta tctatataaa ccattacata    660
gatgtccatc ccaatacgga catgcgctga acacaacaaa cgattctttt taagagaatc    720
tctctctctc tattctctcc acttctctct ctgtggatcg atggcagctt cggttgatcc    780
tttggtggtt ggaagagtga tcggagatgt gttggacatg ttcatcccca ccgccaacat    840
gtctgtctac tttggcccca acacataac taacggctgc gagatcaaac cctctgccgc    900
agtcaaccct ccaaaagtca acatctccgg caactccaat gagctttaca ctctcgtata    960
catattaatc ttctcgcttc tatccatttt ttgtgctagc t                        1001
```

<210> SEQ ID NO 39
<211> LENGTH: 685
<212> TYPE: DNA
<213> ORGANISM: Brassica napus

<400> SEQUENCE: 39

```
tgtggatcga tggcagcttc ggttgatcct ttggtggttg aagagtgat cggagatgtg     60 ttggacatgt tcatccccac cgccaacatg tctgtctact ttggccccaa acacataact    120
aacggctgcg agatcaaacc ctctgccgca gtcaaccctc caaaagtcaa catctccggc    180
aactccaatg agctttacac tctcgtgatg actgacccgg acgcacctag cccgagtgag    240
ccgaacatga gagaatgggt ccattggatt gtcgtggata tcccgggagg caccaacccc    300
tcaaaaggaa aggagatact gccatatatg gagccgagac caccggtggg gattcaccgt    360
tacatatttg tactttttcag gcagaactca ccggtgggta tgatggtgca gcagccgcct    420
```

| | |
|---|---|
| tcgcgagcca acttcagcac ccgaatgttc gctggacatc tcgatcttgg tttgcctgtg | 480 |
| gccacagttt acttcaacgc ccagaaagag ccagcttcac gcagacgctg atgcaygtca | 540 |
| accaaaataa aagagagagc cttttccggt tttacctaaa aaccggaccg gaaagaaata | 600 |
| tggggtttat atatcaaacc atattttgta tcatccggtt ctcgactata tatatgtgta | 660 |
| gatgcatata caattataca aatat | 685 |

<210> SEQ ID NO 40
<211> LENGTH: 1001
<212> TYPE: DNA
<213> ORGANISM: Brassica napus

<400> SEQUENCE: 40

| | |
|---|---|
| atgatttatt atgtttcagg attgtcgtgg atatcccggg aggcaccaac ccctcaaaag | 60 |
| gtatgaaaat aaaagccaaa actaaatttt cgattttga attttaattg tttcgctatt | 120 |
| ttccggaatc tcttaattat tattttttcta aactttttttt acaaatgaat ttcactttttt | 180 |
| aactcacttt ctaactcact tgcttagata taaaataacg ttagtgtgaa agccactaag | 240 |
| aacacatgat aatggttaac tatgtccatg aagacgtgtt tgaatctaat tgaaaaatcc | 300 |
| gatacactag tatgttttat tcatttaaac atattatctg tgcaacgtgg tgctttcggt | 360 |
| ttgatatgaa atggattccc cgtattgcac gatattgatt ggttcaacaa cacaaatatg | 420 |
| catgactctc acatgcatat aggtataaga gtcactatgt aatttttcctt ggtttcaagt | 480 |
| tatgccccaa aataatacgt ratgtcttct aaaaccaaca tctaatgtat gtctgtacgt | 540 |
| gtacactgat gtatatcaac taaacaacgg acacatgtct tcataaaaaa accttaaaca | 600 |
| tgacaaagca taagtgaata gaggatgata attattttat ttttattatt agtaccacgg | 660 |
| gaaactttga aatcgatata ctagcatgtt tttcatttta ggaaaggaga tactgccata | 720 |
| tatggagccg agaccaccgg tggggattca ccgttacata tttgtacttt tcaggcagaa | 780 |
| ctcaccggtg gtatgatgg tgcagcagcc gccttcgcga gccaacttca gcacccgaat | 840 |
| gttcgctgga catctcgatc ttggtttgcc tgtggccaca gtttacttca acgcccagaa | 900 |
| agagccagct tcacgcagac gctgatgcac gcaaccaaaa taaagagagag agcctttttcc | 960 |
| ggttttacct aaaaaccgga ccggaaagaa atatgggggtt t | 1001 |

<210> SEQ ID NO 41
<211> LENGTH: 1001
<212> TYPE: DNA
<213> ORGANISM: Brassica napus

<400> SEQUENCE: 41

| | |
|---|---|
| tgatttatta tgtttcagga ttgtcgtgga tatcccggga ggcaccaacc cctcaaaagg | 60 |
| tatgaaaata aaagccaaaa ctaaattttc gattttgaa ttttaattgt ttcgctattt | 120 |
| tccggaatct cttaattatt atttttctaa actttttttta caaatgaatt tcactttta | 180 |
| actcactttc taactcactt gcttagatat aaaataacgt tagtgtgaaa gccactaaga | 240 |
| acacatgata atggttaact atgtccatga agacgtgttt gaatctaatt gaaaaatccg | 300 |
| atacactagt atgttttatt catttaaaca tattatctgt gcaacgtggt gctttcggtt | 360 |
| tgatatgaaa tggattcccc gtattgcacg atattgattg gttcaacaac acaaatatgc | 420 |
| atgactctca catgcatata ggtataagag tcactatgta atttttccttg gtttcaagtt | 480 |
| atgccccaaa aataatacgta rtgtcttcta aaaccaacat ctaatgtatg tctgtacgtg | 540 |
| tacactgatg tatatcaact aaacaacgga cacatgtctt cataaaaaaa ccttaaacat | 600 |

```
gacaaagcat aagtgaatag aggatgataa ttatttttatt tttattatta gtaccacggg      660
aaactttgaa atcgatatac tagcatgttt ttcattttag gaaaggagat actgccatat      720
atggagccga gaccaccggt ggggattcac cgttacatat ttgtacttttt caggcagaac     780 tcaccggtgg gtatgatggt gcagcagccg ccttcgcgag ccaacttcag cacccgaatg      840
ttcgctggac atctcgatct tggtttgcct gtggccacag tttacttcaa cgcccagaaa      900
gagccagctt cacgcagacg ctgatgcacg caaccaaaat aaaagagaga gccttttccg      960
gttttaccta aaaaccggac cggaaagaaa tatggggttt a                          1001
```

<210> SEQ ID NO 42
<211> LENGTH: 1001
<212> TYPE: DNA
<213> ORGANISM: Brassica napus

<400> SEQUENCE: 42

```
aggattgtcg tggatatccc gggaggcacc aaccccctcaa aaggtatgaa aataaaagcc     60
aaaactaaat tttcgatttt tgaattttaa ttgtttcgct attttccgga atctcttaat      120
tattattttt ctaaactttt tttacaaatg aatttcactt tttaactcac tttctaactc     180
acttgcttag atataaaata cgttagtgt gaaagccact aagaacacat gataatggtt      240
aactatgtcc atgaagacgt gtttgaatct aattgaaaaa tccgatacac tagtatgttt     300
tattcattta aacatattat ctgtgcaacg tggtgctttc ggtttgatat gaaatggatt     360
ccccgtattg cacgatattg attggttcaa caacacaaat atgcatgact ctcacatgca     420
tataggtata agagtcacta tgtaatttttc cttggtttca agttatgccc caaaataata     480
cgtaatgtct tctaaaacca rcatctaatg tatgtctgta cgtgtacact gatgtatatc      540
aactaaacaa cggacacatg tcttcataaa aaaaccttaa acatgacaaa gcataagtga      600
atagaggatg ataattattt tatttttatt attagtacca cgggaaactt tgaaatcgat      660
atactagcat gttttttcatt ttaggaaagg agatactgcc atatatggag ccgagaccac     720
cggtggggat tcaccgttac atatttgtac ttttcaggca gaactcaccg gtgggtatga     780
tggtgcagca gccgccttcg cgagccaact tcagcacccg aatgttcgct ggacatctcg      840
atcttggttt gcctgtggcc acagtttact tcaacgccca gaaagagcca gcttcacgca     900
gacgctgatg cacgcaacca aaataaaaga gagagccttt tccggttttta cctaaaaacc     960 ggaccggaaa gaaatatggg gtttatatat caaaccatat t                          1001
```

<210> SEQ ID NO 43
<211> LENGTH: 1001
<212> TYPE: DNA
<213> ORGANISM: Brassica napus

<400> SEQUENCE: 43

```
ttgtttcgct attttccgga atctcttaat tattattttt ctaaactttt tttacaaatg      60
aatttcactt tttaactcac tttctaactc acttgcttag atataaaata cgttagtgt      120 gaaagccact aagaacacat gataatggtt aactatgtcc atgaagacgt gtttgaatct     180
aattgaaaaa tccgatacac tagtatgttt tattcattta aacatattat ctgtgcaacg     240
tggtgctttc ggtttgatat gaaatggatt ccccgtattg cacgatattg attggttcaa     300
caacacaaat atgcatgact ctcacatgca tataggtata agagtcacta tgtaatttttc    360 cttggtttca agttatgccc caaaataata cgtaatgtct tctaaaacca acatctaatg     420
```

| | |
|---|---|
| tatgtctgta cgtgtacact gatgtatatc aactaaacaa cggacacatg tcttcataaa | 480 |
| aaaaccttaa acatgacaaa rcataagtga atagaggatg ataattattt tattttattt | 540 |
| attagtacca cgggaaactt tgaaatcgat atactagcat gtttttcatt ttaggaaagg | 600 |
| agatactgcc atatatggag ccgagaccac cggtggggat tcaccgttac atatttgtac | 660 |
| ttttcaggca gaactcaccg gtgggtatga tggtgcagca gccgccttcg cgagccaact | 720 |
| tcagcacccg aatgttcgct ggacatctcg atcttggttt gcctgtggcc acagtttact | 780 |
| tcaacgccca gaaagagcca gcttcacgca gacgctgatg cacgcaacca aaataaaaga | 840 |
| gagagccttt tccggtttta cctaaaaacc ggaccggaaa gaaatatggg gtttatatat | 900 |
| caaaccatat tttgtatcat ccggttctcg actatatata tgtgtagatg catatacaat | 960 |
| tatacaaata tgtttatgtt tgtgtgttat attaagtggc t | 1001 |

<210> SEQ ID NO 44
<211> LENGTH: 1001
<212> TYPE: DNA
<213> ORGANISM: Brassica napus

<400> SEQUENCE: 44

| | |
|---|---|
| tacaaatgaa tttcactttt taactcactt tctaactcac ttgcttagat ataaaataac | 60 |
| gttagtgtga aagccactaa gaacacatga taatggttaa ctatgtccat gaagacgtgt | 120 |
| ttgaatctaa ttgaaaaatc cgatacacta gtatgtttta ttcatttaaa catattatct | 180 |
| gtgcaacgtg gtgctttcgg tttgatatga aatggattcc ccgtattgca cgatattgat | 240 |
| tggttcaaca acacaaatat gcatgactct cacatgcata taggtataag agtcactatg | 300 |
| taatttttcct tggtttcaag ttatgcccca aataatacg taatgtcttc taaaaccaac | 360 |
| atctaatgta tgtctgtacg tgtacactga tgtatatcaa ctaaacaacg gacacatgtc | 420 |
| ttcataaaaa aaccttaaac atgacaaagc ataagtgaat agaggatgat aattatttta | 480 |
| tttttattat tagtaccacg rgaaactttg aaatcgatat actagcatgt ttttcatttt | 540 |
| aggaaaggag atactgccat atatggagcc gagaccaccg gtggggattc accgttacat | 600 |
| atttgtactt tcaggcaga actcaccggt gggtatgatg tgcagcagc cgccttcgcg | 660 |
| agccaacttc agcacccgaa tgttcgctgg acatctcgat cttggtttgc ctgtggccac | 720 |
| agtttacttc aacgcccaga aagagccagc ttcacgcaga cgctgatgca cgcaaccaaa | 780 |
| ataaaagaga gagccttttc cggttttacc taaaaaccgg accggaaaga aatatgggt | 840 |
| ttatatatca aaccatattt tgtatcatcc ggttctcgac tatatatatg tgtagatgca | 900 |
| tatacaatta tacaaatatg tttatgtttg tgtgttatat taagtggctt gcgtataata | 960 |
| tatggttttc gttttctttt atctttaaat aaactaaaaa a | 1001 |

<210> SEQ ID NO 45
<211> LENGTH: 1002
<212> TYPE: DNA
<213> ORGANISM: Brassica napus
<220> FEATURE:
<221> NAME/KEY: misc_feature
<222> LOCATION: (502)..(502)
<223> OTHER INFORMATION: where n is an insertion/deletion [+/T]

<400> SEQUENCE: 45

| | |
|---|---|
| cgcccagaaa gagccagctt cacgcagacg ctgatgcacg caaccaaaat aaaagagaga | 60 |
| gccttttccg gttttaccta aaaaccggac cggaaagaaa tatggggttt atatatcaaa | 120 |
| ccatattttg tatcatccgg ttctcgacta tatatatgtg tagatgcata taattata | 180 |

```
caaatatgtt tatgtttgtg tgttatatta agtggcttgc gtataatata tggttttcgt      240
tttcttttat ctttaaataa actaaaaaat aaaggtatgt atcaaattat aaagaaacaa      300
gaagagagga taaacaaaaa aaatgaaaat tctagtatac tgccttatta aaaaaaaaaa      360
atactattag ttcttaaacc gaaattcaga aatataaatg tcggttacaa atttgattcg      420
aacaaaatga accatttccc gtttaaataa actagtttca accaccacat ttaagttaaa      480
atatatcata ttattaattt tnaacccaaa actcaagaat acaaatgtca gttacaagct      540
taattccaac aaaatgattt aattctaact taaataaact agcttgcttg accgccggct      600
gacttaaata aactagcttt tcttgttgat cattagcctt cttctcctct gaacctatgt      660
agcttgtttt ctaaagattt tgatccacgc actctccttg aatttcaact acatcttctg      720
tggactcata tctttccttc tctctattct cagagtcttg ttttattcca gaatcatcaa      780
agcttggaca aatcgaatgt aacttcacgt tgatccactg aaaaatcttg ttcgtaagag      840
tttggtgttg aagtaacatc tagtgcttcg ccattggttt cttagagcat gattattgca      900
aagacccata ttaggggttc ttattatttt ttaatgcttt taagtacaaa aagtgattta      960
agagacaaat ttaagaaacc ctaacattta attgctccat tg                       1002

<210> SEQ ID NO 46
<211> LENGTH: 1001
<212> TYPE: DNA
<213> ORGANISM: Brassica napus

<400> SEQUENCE: 46
agagcctttt ccggttttac ctaaaaaccg gaccggaaag aaatatgggg tttatatatc       60
aaaccatatt ttgtatcatc cggttctcga ctatatatat gtgtagatgc atatacaatt      120
atacaaatat gtttatgttt gtgtgttata ttaagtggct tgcgtataat atatggtttt      180
cgttttcttt tatctttaaa taaactaaaa aataaaggta tgtatcaaat tataaagaaa      240
caagaagaga ggataaacaa aaaaaatgaa aattctagta tactgcctta ttaaaaaaaa      300
aaaatactat tagttcttaa accgaaattc agaaatataa atgtcggtta caaatttgat      360
tcgaacaaaa tgaaccattt cccgtttaaa taaactagtt caaccaccac atttaagtt       420 aaaatatatc atattattaa ttttaaccca aaactcaaga atacaaatgt cagttacaag      480
cttaattcca acaaaatgat ytaattctaa cttaaataaa ctagcttgct tgaccgccgg      540
ctgacttaaa taaactagct tttcttgttg atcattagcc ttcttctcct ctgaacctat      600
gtagcttgtt ttctaaagat tttgatccac gcactctcct tgaatttcaa ctacatcttc      660
tgtggactca tatctttcct tctctctatt ctcagagtct tgtttattc cagaatcatc      720 aaagcttgga caaatcgaat gtaacttcac gttgatccac tgaaaaatct tgttcgtaag      780
agtttggtgt tgaagtaaca tctagtgctt cgccattggt ttcttagagc atgattattg      840
caaagaccca tattaggggt tcttattatt ttttaatgct tttaagtaca aaaagtgatt      900
taagagacaa atttaagaaa ccctaacatt taattgctcc attgcaaggt tcttacaaca      960
ttactttcac tcttcttact tgatcttctt tagccaatgt t                         1001

<210> SEQ ID NO 47
<211> LENGTH: 1001
<212> TYPE: DNA
<213> ORGANISM: Brassica napus

<400> SEQUENCE: 47
```

```
atatggggtt tatatatcaa accatatttt gtatcatccg gttctcgact atatatatgt      60
gtagatgcat atacaattat acaaatatgt ttatgtttgt gtgttatatt aagtggcttg     120
cgtataatat atggttttcg ttttcttttta tctttaaata aactaaaaaa taaaggtatg     180
tatcaaatta taaagaaaca agaagagagg ataaacaaaa aaaatgaaaa ttctagtata     240
ctgccttatt aaaaaaaaaa aatactatta gttcttaaac cgaaattcag aaatataaat     300
gtcggttaca aatttgattc gaacaaaatg aaccatttcc cgtttaaata aactagtttc     360
aaccaccaca tttaagttaa aatatatcat attattaatt ttaacccaaa actcaagaat     420
acaaatgtca gttacaagct taattccaac aaaatgattt aattctaact taaataaact     480
agcttgcttg accgccggct ractaaaata aactagcttt tcttgttgat cattagcctt     540
cttctcctct gaacctatgt agcttgtttt ctaaagattt tgatccacgc actctccttg     600
aatttcaact acatcttctg tggactcata tctttccttc tctctattct cagagtcttg     660
ttttattcca gaatcatcaa agcttggaca atcgaatgt aacttcacgt tgatccactg     720
aaaaatcttg ttcgtaagag tttggtgttg aagtaacatc tagtgcttcg ccattggttt     780
cttagagcat gattattgca aagacccata ttaggggttc ttattatttt ttaatgcttt     840
taagtacaaa aagtgattta agagacaaat ttaagaaacc ctaacattta attgctccat     900
tgcaaggttc ttacaacatt actttcactc ttcttacttg atcttcttta gccaatgttg     960
ttccaatgtc aaagacgatg aaacagaaac aagaaaacct c                        1001
```

<210> SEQ ID NO 48
<211> LENGTH: 1001
<212> TYPE: DNA
<213> ORGANISM: Brassica napus

<400> SEQUENCE: 48

```
taatatatgg ttttcgtttt cttttatctt taaataaact aaaaaataaa ggtatgtatc      60
aaattataaa gaaacaagaa gagaggataa acaaaaaaaa tgaaaattct agtatactgc     120
cttattaaaa aaaaaaaata ctattagttc ttaaaccgaa attcagaaat ataaatgtcg     180
gttacaaatt tgattcgaac aaaatgaacc atttcccgtt taaataaact agtttcaacc     240
accacattta agttaaaata tcatatta ttaattttaa cccaaaactc aagaatacaa     300
atgtcagtta caagcttaat tccaacaaaa tgatttaatt ctaacttaaa taaactagct     360
tgcttgaccg ccggctgact aaataaact agcttttctt gttgatcatt agccttcttc     420
tcctctgaac ctatgtagct tgttttctaa agattttgat ccacgcactc tccttgaatt     480
tcaactacat cttctgtgga ytcatatctt tccttctctc tattctcaga gtcttgtttt     540
attccagaat catcaaagct tggacaaatc gaatgtaact tcacgttgat ccactgaaaa     600
atcttgttcg taagagtttg gtgttgaagt aacatctagt gcttcgccat ggtttctta     660 gagcatgatt attgcaaaga cccatattag gggttcttat tatttttaa tgcttttaag     720 tacaaaaagt gatttaagag acaaatttaa gaaaccctaa catttaattg ctccattgca     780
aggttcttac aacattactt tcactcttct tacttgatct tctttagcca atgttgttcc     840
aatgtcaaag acgatgaaac agaaacaaga aaacctcaat aaaatgaatc aataaccaga     900
accttgaaac atgaaacaaa acaacaaagc atatcattct cattactcaa acagaacaag     960
aacattaaca tgaaacagag acagaataag caaaacaacg t                        1001
```

<210> SEQ ID NO 49
<211> LENGTH: 1001

```
<212> TYPE: DNA
<213> ORGANISM: Brassica napus

<400> SEQUENCE: 49
ataaagaaac aagaagagag gataaacaaa aaaaatgaaa attctagtat actgccttat      60
taaaaaaaaa aaatactatt agttcttaaa ccgaaattca gaaatataaa tgtcggttac     120
aaatttgatt cgaacaaaat gaaccatttc ccgtttaaat aaactagttt caaccaccac     180
atttaagtta aaatatatca tattattaat tttaacccaa aactcaagaa tacaaatgtc     240
agttacaagc ttaattccaa caaaatgatt taattctaac ttaaataaac tagcttgctt     300
gaccgccggc tgacttaaat aaactagctt ttccttgttga tcattagcct tcttctcctc    360
tgaacctatg tagcttgttt tctaaagatt ttgatccacg cactctcctt gaatttcaac    420
tacatcttct gtggactcat atctttcctt ctctctattc tcagagtctt gttttattcc    480
agaatcatca aagcttggac raatcgaatg taacttcacg ttgatccact gaaaaatctt    540
gttcgtaaga gtttggtgtt gaagtaacat ctagtgcttc gccattggtt tcttagagca    600
tgattattgc aaagacccat attaggggtt cttattattt tttaatgctt ttaagtacaa    660
aaagtgattt aagagacaaa tttaagaaac cctaacattt aattgctcca ttgcaaggtt    720
cttacaacat tactttcact cttcttactt gatcttcttt agccaatgtt gttccaatgt    780
caaagacgat gaaacagaaa caagaaaacc tcaataaaat gaatcaataa ccagaacctt    840
gaaacatgaa acaaaacaac aaagcatatc attctcatta ctcaaacaga acaagaacat    900
taacatgaaa cagagacaga ataagcaaaa caacgtgtag ttccccgtac gtcttgtgca    960
gcattgtaat tcttcacgga atcagtagta aaagttattt a                      1001

<210> SEQ ID NO 50
<211> LENGTH: 1001
<212> TYPE: DNA
<213> ORGANISM: Brassica napus

<400> SEQUENCE: 50
attaaaaaaa aaaatactca ttagttctta accgaaatt cagaatatata aatgtcggtt     60
acaaatttga ttcgaacaaa atgaaccatt tcccgtttaa ataaactagt ttcaaccacc    120
acatttaagt taaatatatat catattatta attttaaccc aaaactcaag aatacaaatg    180
tcagttacaa gcttaattcc aacaaaatga tttaattcta acttaaataa actagcttgc    240
ttgaccgccg gctgacttaa ataaactagc ttttcttgtt gatcattagc cttcttctcc    300
tctgaaccta tgtagcttgt tttctaaaga ttttgatcca cgcactctcc ttgaatttca    360
actacatctt ctgtggactc atatctttcc ttctctctat tctcagagtc ttgttttatt    420
ccagaatcat caaagcttgg acaaatcgaa tgtaacttca cgttgatcca ctgaaaaatc    480
ttgttcgtaa gagtttggtg ytgaagtaac atctagtgct tcgccattgg tttcttagag    540
catgattatt gcaaagaccc atattagggg ttccttattat tttttaatgc ttttaagtac    600
aaaaagtgat ttaagagaca aatttaagaa accctaacat ttaattgctc cattgcaagg    660
ttcttacaac attactttca ctcttcttac ttgatcttct ttagccaatg ttgttccaat    720
gtcaaagacg atgaaacaga acaagaaaa cctcaataaa atgaatcaat aaccagaacc    780
ttgaaacatg aaacaaaaca caaagcata tcattctcat tactcaaaca gaacaagaac    840
attaacatga acagagaca gaataagcaa acaacgtgt agttccccgt acgtcttgtg    900
cagcattgta attcttcacg gaatcagtag taaaagttat ttattaaacc gttctaacag    960
```
tagtaaacaa acatccaggt gctgtgaaaa aaatctatca a                1001

<210> SEQ ID NO 51
<211> LENGTH: 1001
<212> TYPE: DNA
<213> ORGANISM: Brassica napus

<400> SEQUENCE: 51
tactattagt tcttaaaccg aaattcagaa atataaatgt cggttacaaa tttgattcga    60
acaaaatgaa ccatttcccg tttaaataaa ctagtttcaa ccaccacatt taagttaaaa   120
tatatcatat tattaatttt aacccaaaac tcaagaatac aaatgtcagt tacaagctta   180
attccaacaa aatgatttaa ttctaactta aataaactag cttgcttgac cgccggctga   240
cttaaataaa ctagctttc ttgttgatca ttagccttct tctcctctga acctatgtag    300
cttgttttct aaagattttg atccacgcac tctccttgaa tttcaactac atcttctgtg   360
gactcatatc tttccttctc tctattctca gagtcttgtt ttattccaga atcatcaaag   420
cttggacaaa tcgaatgtaa cttcacgttg atccactgaa aaatcttgtt cgtaagagtt   480
tggtgttgaa gtaacatcta stgcttcgcc attggtttct tagagcatga ttattgcaaa   540
gacccatatt aggggttctt attatttttt aatgctttta agtacaaaaa gtgatttaag   600
agacaaattt aagaacccct aacatttaat tgctccattg caaggttctt acaacattac   660
tttcactctt cttacttgat cttctttagc caatgttgtt ccaatgtcaa agacgatgaa   720
acagaaacaa gaaaacctca ataaaatgaa tcaataacca gaaccttgaa acatgaaaca   780
aaacaacaaa gcatatcatt ctcattactc aaacagaaca agaacattaa catgaaacag   840
agacagaata agcaaaacaa cgtgtagttc cccgtacgtc ttgtgcagca ttgtaattct   900
tcacggaatc agtagtaaaa gttatttatt aaaccgttct aacagtagta aacaaacatc   960
caggtgctgt gaaaaaaatc tatcaattga aacaacgatc t                     1001

<210> SEQ ID NO 52
<211> LENGTH: 1002
<212> TYPE: DNA
<213> ORGANISM: Brassica napus
<220> FEATURE:
<221> NAME/KEY: misc_feature
<222> LOCATION: (502)..(502)
<223> OTHER INFORMATION: where n is an insertion/deletion [+/A]

<400> SEQUENCE: 52
tggtggaaga agaagactca gctttgttgt tgttgcagag ataaccgcgg ctcagaggta    60
aggacgaaga agaatgcgac agctgtctca taagagacgt cccttgcgga gccaaattaa   120
gagacgtctt ctccgtgttt tgtatttttc attttttttt aatcacaata acctaagaga   180
catgcttagg agactgcgat aatggtgctc ttacagaccc cacgacagga gggcttgttc   240
actgtattct aattggtgga aaagaaagct acgggaaaga aatactcttg tgagcacata   300
tgttgttgtt caattctaag ggcagaaacg agttgctaga gttccatttt aaccagtttc   360
tgtaccctt taaacattgt aattgttgca tacacgccag cttattaaga aaatacaaat   420
tcaagtgtga ctactctgtt ccctcatttt gataggatta tcaaagatat cacattgaaa   480
caaaacagaa gcaactaaaa ancagtaaga tctctcacaa acaatataaa agatcgaaac   540
ctagaattga cataaaacaa aacattattg caaaatctca gtttgttgac aaaacaaaag   600
tgtgatagat aaaaaaacaca tccaaggaga gagacagggc aaagagatgg gataaactag   660
taacggccaa taccccaaac tctgataact ccatcggtgt atccactgaa caaggtgctt   720

```
ccatccgcac tccagctcag gctagtgcag taaataacct gtccaaaaaa gtaaatgttt      780
aagtctagtt tctcaatcta ggcaagaaaa aaaaacagtt cttaccaaaa tataaaaaca      840
ttcaaaaatt gccatagata gaaaaatcta tatcagatct atcgattaca ttcacatatt      900
gataaaacac tagccaacaa tatactgcaa tctatggcaa acatgtataa aagtaaattc      960
agacaaaaga acacaagaca tttgagcatc cacatgaaaa ac                       1002

<210> SEQ ID NO 53
<211> LENGTH: 1001
<212> TYPE: DNA
<213> ORGANISM: Brassica napus

<400> SEQUENCE: 53
gttgttgttg cagagataac cgcggctcag aggtaaggac gaagaagaat gcgacagctg       60
tctcataaga gacgtccctt gcggagccaa attaagagac gtcttctccg tgttttgtat      120
ttttcatttt tttttaatca caataaccta agagacatgc ttaggagact gcgataatgg      180
tgctcttaca gaccccacga caggagggct tgttcactgt attctaattg gtggaaaaga      240
aagctacggg aaagaaatac tcttgtgagc acatatgttg ttgttcaatt ctaagggcag      300
aaacgagttg ctagagttcc attttaacca gtttctgtac accttaaaac attgtaattg      360
ttgcatacac gccagcttat taagaaaata caaattcaag tgtgactact ctgttccctc      420
attttgatag gattatcaaa gatatcacat tgaaacaaaa cagaagcaac taaaaacagt      480
aagatctctc acaaacaata waaaagatcg aaacctagaa ttgacataaa acaaaacatt      540
attgcaaaat ctcagtttgt tgacaaaaca aaagtgtgat agataaaaaa cacatccaag      600
gagagagaca gggcaaagag atgggataaa ctagtaacgg ccaataccc aaactctgat       660
aactccatcg gtgtatccac tgaacaaggt gcttccatcc gcactccagc tcaggctagt      720
gcagtaaata acctgtccaa aaagtaaat gtttaagtct agtttctcaa tctaggcaag       780
aaaaaaaaac agttcttacc aaaatataaa aacattcaaa aattgccata gatagaaaaa      840
tctatatcag atctatcgat tacattcaca tattgataaa acactagcca acaatatact      900
gcaatctatg gcaaacatgt ataaaagtaa attcagacaa agaacacaa gacatttgag       960
catccacatg aaaacaaac atatttacaa aacataaaca a                          1001

<210> SEQ ID NO 54
<211> LENGTH: 1001
<212> TYPE: DNA
<213> ORGANISM: Brassica napus

<400> SEQUENCE: 54
agagacgtct tctccgtgtt ttgtattttt catttttttt taatcacaat aacctaagag       60
acatgcttag gagactgcga taatggtgct cttacagacc ccacgacagg agggcttgtt      120
cactgtattc taattggtgg aaaagaaagc tacgggaaag aaatactctt gtgagcacat      180
atgttgttgt tcaattctaa gggcagaaac gagttgctag agttccattt taaccagttt      240
ctgtacacct taaacattg taattgttgc atacacgcca gcttattaag aaaatacaaa       300
ttcaagtgtg actactctgt tccctcattt tgataggatt atcaaagata tcacattgaa      360
acaaaacaga agcaactaaa aacagtaaga tctctcacaa acaatataaa agatcgaaac      420
ctagaattga cataaacaa acattattg caaaatctca gtttgttgac aaaacaaaag       480
tgtgatagat aaaaaacaca wccaaggaga gagacagggc aaagagatgg gataaactag      540
```

```
taacggccaa tacccaaaac tctgataact ccatcggtgt atccactgaa caaggtgctt      600
ccatccgcac tccagctcag gctagtgcag taaataaccct gtccaaaaaa gtaaatgttt      660
aagtctagtt tctcaatcta ggcaagaaaa aaaaacagtt cttaccaaaa tataaaaaca      720
ttcaaaaatt gccatagata gaaaaatcta tatcagatct atcgattaca ttcacatatt      780
gataaaacac tagccaacaa tatactgcaa tctatggcaa acatgtataa agtaaattc      840 agacaaaaga acacaagaca tttgagcatc cacatgaaaa acaaacatat ttacaaaaca      900
taaacaagga tataaaacca caatcataac cataagcatg catcgtttat ttgcatttca      960
atagatcaat ccaaaagaac catttctata aacactatcc t                           1001
```

<210> SEQ ID NO 55
<211> LENGTH: 1001
<212> TYPE: DNA
<213> ORGANISM: Brassica napus

<400> SEQUENCE: 55

```
gataatggtg ctcttacaga ccccacgaca ggagggcttg ttcactgtat tctaattggt       60
ggaaaagaaa gctacgggaa agaaatactc ttgtgagcac atatgttgtt gttcaattct      120
aagggcagaa acgagttgct agagttccat tttaaccagt ttctgtacac ctttaaacat      180
tgtaattgtt gcatacacgc cagcttatta agaaaataca aattcaagtg tgactactct      240
gttccctcat tttgatagga ttatcaaaga tatcacattg aaacaaaaca gaagcaacta      300
aaaacagtaa gatctctcac aaacaatata aagatcgaa acctagaatt gacataaaac      360
aaaacattat tgcaaaatct cagtttgttg acaaacaaa agtgtgatag ataaaaaaca      420
catccaagga gagagacagg gcaaagagat gggataaact agtaacggcc aatacccccaa      480 actctgataa ctccatcggt rtatccactg aacaaggtgc ttccatccgc actccagctc      540
aggctagtgc agtaaataac ctgtccaaaa aagtaaatgt ttaagtctag tttctcaatc      600
taggcaagaa aaaaaaacag ttcttaccaa aatataaaaa cattcaaaaa ttgccataga      660
tagaaaaatc tatatcagat ctatcgatta cattcacata ttgataaaac actagccaac      720
aatatactgc aatctatggc aaacatgtat aaagtaaat tcagacaaaa gaacacaaga      780
catttgagca tccacatgaa aacaaacat atttacaaaa cataaacaag gatataaaac      840
cacaatcata accataagca tgcatcgttt atttgcattt caatagatca atccaaaaga      900
accatttcta taaacactat cctctatcaa cagtttacct aaactaaaga atattatcc      960 atacaataag catcaaactt gcatgtcttt gtacctttct t                           1001
```

<210> SEQ ID NO 56
<211> LENGTH: 1001
<212> TYPE: DNA
<213> ORGANISM: Brassica napus

<400> SEQUENCE: 56

```
tgtattctaa ttggtggaaa agaaagctac gggaagaaa tactcttgtg agcacatatg       60
ttgttgttca attctaaggg cagaaacgag ttgctagagt tccattttaa ccagtttctg      120 tacacctta acattgtaa ttgttgcata cacgccagct tattaagaaa atacaaattc      180
aagtgtgact actctgttcc ctcatttga taggattatc aaagatatca cattgaaaca      240
aaacagaagc aactaaaaac agtaagatct ctcacaaaca atataaaaga tcgaaaccta      300
gaattgacat aaaacaaaac attattgcaa aatctcagtt tgttgacaaa acaaagtgt      360 gatagataaa aaacacatcc aaggagagag acagggcaaa gagatgggat aaactagtaa      420
```

```
cggccaatac cccaaactct gataactcca tcggtgtatc cactgaacaa ggtgcttcca    480
tccgcactcc agctcaggct rgtgcagtaa ataacctgtc caaaaaagta aatgtttaag    540
tctagtttct caatctaggc aagaaaaaaa aacagttctt accaaaatat aaaaacattc    600
aaaaattgcc atagatagaa aaatctatat cagatctatc gattacattc acatattgat    660
aaaacactag ccaacaatat actgcaatct atggcaaaca tgtataaaag taaattcaga    720
caaaagaaca caagacattt gagcatccac atgaaaaaca aacatattta caaaacataa    780
acaaggatat aaaaccacaa tcataaccat aagcatgcat cgtttatttg catttcaata    840
gatcaatcca aaagaaccat ttctataaac actatcctct atcaacagtt tacctaaact    900
aaagaaatat tatccataca ataagcatca aacttgcatg tctttgtacc tttcttttgg    960
tggcagcagt accacttcca tcggacttct cagcctcagc c                      1001
```

<210> SEQ ID NO 57
<211> LENGTH: 1001
<212> TYPE: DNA
<213> ORGANISM: Brassica napus

<400> SEQUENCE: 57

```
gggcagaaac gagttgctag agttccattt taaccagttt ctgtacacct ttaaacattg     60
taattgttgc atacacgcca gcttattaag aaaatacaaa ttcaagtgtg actactctgt    120
tccctcattt tgataggatt atcaaagata tcacattgaa acaaaacaga agcaactaaa    180
aacagtaaga tctctcacaa acaatataaa agatcgaaac ctagaattga cataaaacaa    240
aacattattg caaaatctca gtttgttgac aaaacaaaag tgtgatagat aaaaaacaca    300
tccaaggaga gagacagggc aaagagatgg gataaactag taacggccaa taccccaaac    360
tctgataact ccatcggtgt atccactgaa caaggtgctt ccatccgcac tccagctcag    420
gctagtgcag taaataacct gtccaaaaaa gtaaatgttt aagtctagtt tctcaatcta    480
ggcaagaaaa aaaaacagtt sttaccaaaa tataaaaaca ttcaaaaatt gccatagata    540
gaaaaatcta tatcagatct atcgattaca ttcacatatt gataaaacac tagccaacaa    600
tatactgcaa tctatggcaa acatgtataa aagtaaattc agacaaaaga acacaagaca    660
tttgagcatc cacatgaaaa acaaacatat ttacaaaaca taaacaagga tataaaacca    720
caatcataac cataagcatg catcgtttat ttgcatttca atagatcaat ccaaaagaac    780
catttctata aacactatcc tctatcaaca gtttacctaa actaaagaaa tattatccat    840
acaataagca tcaaacttgc atgtctttgt acctttcttt tggtggcagc agtaccactt    900
ccatcggact tctcagcctc agccttgaga tcaaccttca agtcctcaac aacactcttg    960
ctctcaagat cccaaatctt aatacctgc tcagtcgcag c                       1001
```

<210> SEQ ID NO 58
<211> LENGTH: 1001
<212> TYPE: DNA
<213> ORGANISM: Brassica napus

<400> SEQUENCE: 58

```
agaaacgagt tgctagagtt ccattttaac cagtttctgt acacctttaa acattgtaat     60
tgttgcatac acgccagctt attaagaaaa tacaaattca agtgtgacta ctctgttccc    120
tcattttgat aggattatca agatatcac attgaaacaa acagaagca actaaaaaca    180 gtaagatctc tcacaaacaa tataaagat cgaaacctag aattgacata aacaaaaca    240
```

```
ttattgcaaa atctcagttt gttgacaaaa caaaagtgtg atagataaaa aacacatcca      300
aggagagaga cagggcaaag agatgggata aactagtaac ggccaatacc ccaaactctg      360
ataactccat cggtgtatcc actgaacaag gtgcttccat ccgcactcca gctcaggcta      420
gtgcagtaaa taacctgtcc aaaaaagtaa atgtttaagt ctagtttctc aatctaggca      480
agaaaaaaaa acagttctta mcaaaatata aaacattca aaaattgcca tagatagaaa       540
aatctatatc agatctatcg attacattca catattgata aaacactagc caacaatata      600
ctgcaatcta tggcaaacat gtataaaagt aaattcagac aaaagaacac aagacatttg      660
agcatccaca tgaaaaacaa acatatttac aaaacataaa caaggatata aaaccacaat      720
cataaccata agcatgcatc gtttatttgc atttcaatag atcaatccaa aagaaccatt      780
tctataaaca ctatcctcta tcaacagttt acctaaacta agaaatatt atccatacaa      840 taagcatcaa acttgcatgt cttttgtacct ttcttttggt ggcagcagta ccacttccat     900
cggacttctc agcctcagcc ttgagatcaa ccttcaagtc ctcaacaaca ctcttgctct      960
caagatccca aatcttaata ccctgctcag tcgcagcaca a                         1001
```

<210> SEQ ID NO 59
<211> LENGTH: 1001
<212> TYPE: DNA
<213> ORGANISM: Brassica napus

<400> SEQUENCE: 59

```
gagttgctag agttccattt taaccagttt ctgtacacct ttaaacattg taattgttgc       60
atacacgcca gcttattaag aaaatacaaa ttcaagtgtg actactctgt tccctcattt      120
tgataggatt atcaaagata tcacattgaa acaaaacaga agcaactaaa aacagtaaga      180
tctctcacaa acaatataaa agatcgaaac ctagaattga cataaaacaa acattattg       240 caaaatctca gtttgttgac aaaacaaaag tgtgatagat aaaaaacaca tccaaggaga      300
gagacagggc aaagagatgg ataaactag taacggccaa taccccaaac tctgataact       360
ccatcggtgt atccactgaa caaggtgctt ccatccgcac tccagctcag gctagtgcag      420
taaataacct gtccaaaaaa gtaaatgttt aagtctagtt tctcaatcta ggcaagaaaa      480
aaaaacagtt cttaccaaaa yataaaaaca ttcaaaaatt gccatagata gaaaatcta      540 tatcagatct atcgattaca ttcacatatt gataaaacac tagccaacaa tatactgcaa      600
tctatggcaa acatgtataa aagtaaattc agacaaaaga acacaagaca tttgagcatc      660
cacatgaaaa acaaacatat ttacaaaaca taaacaagga tataaaacca caatcataac      720
cataagcatg catcgtttat ttgcatttca atagatcaat ccaaaagaac catttctata      780
aacactatcc tctatcaaca gtttacctaa actaagaaaa tattatccat acaataagca      840
tcaaacttgc atgtctttgt accttttctt tggtggcagc agtaccactt ccatcggact      900
tctcagcctc agccttgaga tcaaccttca gtcctcaac aacactcttg ctctcaagat      960
cccaaatctt aataccctgc tcagtcgcag cacaaagcca g                         1001
```

<210> SEQ ID NO 60
<211> LENGTH: 1001
<212> TYPE: DNA
<213> ORGANISM: Brassica napus

<400> SEQUENCE: 60

```
cacattgaaa caaaacagaa gcaactaaaa acagtaagat ctctcacaaa caatataaaa       60
gatcgaaacc tagaattgac ataaaacaaa acattattgc aaaatctcag tttgttgaca      120
```

```
aaacaaaagt gtgatagata aaaaacacat ccaaggagag agacagggca aagagatggg      180
ataaactagt aacggccaat accccaaact ctgataactc catcggtgta tccactgaac      240
aaggtgcttc catccgcact ccagctcagg ctagtgcagt aaataacctg tccaaaaaag      300
taaatgttta agtctagttt ctcaatctag gcaagaaaaa aaaacagttc ttaccaaaat      360
ataaaaacat tcaaaaattg ccatagatag aaaaatctat atcagatcta tcgattacat      420
tcacatattg ataaaacact agccaacaat atactgcaat ctatggcaaa catgtataaa      480
agtaaattca gacaaaagaa sacaagacat ttgagcatcc acatgaaaaa caaacatatt      540
tacaaaacat aaacaaggat ataaaaccac aatcataacc ataagcatgc atcgtttatt      600
tgcatttcaa tagatcaatc caaagaacc atttctataa acactatcct ctatcaacag      660
tttacctaaa ctaagaaat attatccata caataagcat caaacttgca tgtctttgta      720
cctttctttt ggtggcagca gtaccacttc catcggactt ctcagcctca gccttgagat      780
caaccttcaa gtcctcaaca acactcttgc tctcaagatc ccaaatctta ataccctgct      840
cagtcgcagc acaaagccag tacctattag gactaaagca aagagcgtga atcacagagt      900
tggcttcaag agagtaaagc ttcttcccct cagccaaatc ccagagcaaa acgacaccgt      960
ctttgcctcc actagcacac agagaaccat caggcgacac a                         1001
```

<210> SEQ ID NO 61
<211> LENGTH: 1001
<212> TYPE: DNA
<213> ORGANISM: Brassica napus

<400> SEQUENCE: 61

```
cattgaaaca aaacagaagc aactaaaaac agtaagatct ctcacaaaca atataaaaga      60
tcgaaaccta gaattgacat aaaacaaaac attattgcaa aatctcagtt tgttgacaaa     120 acaaagtgt gatagataaa aaacacatcc aaggagagag acagggcaaa gagatgggat     180
aaactagtaa cggccaatac cccaaactct gataactcca tcggtgtatc cactgaacaa     240
ggtgcttcca tccgcactcc agctcaggct agtgcagtaa ataacctgtc aaaaaagta     300 aatgtttaag tctagtttct caatctaggc aagaaaaaaa aacagttctt accaaaatat     360 aaaacattc aaaaattgcc atagatagaa aaatctatat cagatctatc gattacattc     420
acatattgat aaaacactag ccaacaatat actgcaatct atggcaaaca tgtataaaag     480
taaattcaga caaagaaca yaagacattt gagcatccac atgaaaaaca acatattta     540 caaaacataa acaaggatat aaaaccacaa tcataaccat aagcatgcat cgtttatttg     600
catttcaata gatcaatcca aagaaccat ttctataaac actatcctct atcaacagtt      660
tacctaaact aagaaatat tatccataca ataagcatca aacttgcatg tctttgtacc     720
tttcttttgg tggcagcagt accacttcca tcggacttct cagcctcagc cttgagatca     780
accttcaagt cctcaacaac actcttgctc tcaagatccc aaatcttaat accctgctca     840
gtcgcagcac aaagccagta cctattagga ctaaagcaaa gagcgtgaat cacagagttg     900
gcttcaagag agtaaagctt cttcccctca gccaaatccc agagcaaaac gacaccgtct     960
ttgcctccac tagcacacag agaaccatca ggcgacacag c                         1001
```

<210> SEQ ID NO 62
<211> LENGTH: 1002
<212> TYPE: DNA
<213> ORGANISM: Brassica napus
<220> FEATURE:

<221> NAME/KEY: misc_feature
<222> LOCATION: (502)..(502)
<223> OTHER INFORMATION: where n is an insertion/deletion [+/A]

<400> SEQUENCE: 62

| | | | | | |
|---|---|---|---|---|---|
| aaaaacacat | ccaaggagag | agacagggca | aagagatggg | ataaactagt | aacggccaat | 60 |
| accccaaact | ctgataactc | catcggtgta | tccactgaac | aaggtgcttc | catccgcact | 120 |
| ccagctcagg | ctagtgcagt | aaataacctg | tccaaaaaag | taaatgttta | agtctagttt | 180 |
| ctcaatctag | gcaagaaaaa | aaaacagttc | ttaccaaaat | ataaaaacat | tcaaaaattg | 240 |
| ccatagatag | aaaaatctat | atcagatcta | tcgattacat | tcacatattg | ataaaacact | 300 |
| agccaacaat | atactgcaat | ctatggcaaa | catgtataaa | agtaaattca | gacaaaagaa | 360 |
| cacaagacat | ttgagcatcc | acatgaaaaa | caaacatatt | tacaaaacat | aaacaaggat | 420 |
| ataaaaccac | aatcataacc | ataagcatgc | atcgtttatt | tgcatttcaa | tagatcaatc | 480 |
| caaaagaacc | atttctataa | ancactatcc | tctatcaaca | gtttacctaa | actaaagaaa | 540 |
| tattatccat | acaataagca | tcaaacttgc | atgtctttgt | acctttcttt | tggtggcagc | 600 |
| agtaccactt | ccatcggact | tctcagcctc | agccttgaga | tcaaccttca | agtcctcaac | 660 |
| aacactcttg | ctctcaagat | cccaaatctt | aatacccctgc | tcagtcgcag | cacaaagcca | 720 |
| gtacctatta | ggactaaagc | aaagagcgtg | aatcacagag | ttggcttcaa | gagagtaaag | 780 |
| cttcttcccc | tcagccaaat | cccagagcaa | acgacaccg | tctttgcctc | cactagcaca | 840 |
| cagagaacca | tcaggcgaca | cagccacagt | actaacgtaa | ccagtgtgac | cagcaagagt | 900 |
| cgacctcagc | ttacagttcg | acaagttcca | aactttcacg | gtcttgtccc | acgacgccga | 960 |
| cacaatcgtc | ggctggagcg | tgttgggact | gaacctaacg | ca | | 1002 |

<210> SEQ ID NO 63
<211> LENGTH: 1001
<212> TYPE: DNA
<213> ORGANISM: Brassica napus

<400> SEQUENCE: 63

| | | | | | |
|---|---|---|---|---|---|
| ggccaatacc | ccaaactctg | ataactccat | cggtgtatcc | actgaacaag | gtgcttccat | 60 |
| ccgcactcca | gctcaggcta | gtgcagtaaa | taacctgtcc | aaaaagtaa | atgtttaagt | 120 |
| ctagtttctc | aatctaggca | agaaaaaaaa | acagttctta | ccaaaatata | aaacattca | 180 |
| aaaattgcca | tagatagaaa | aatctatatc | agatctatcg | attacattca | catattgata | 240 |
| aaacactagc | caacaatata | ctgcaatcta | tggcaaacat | gtataaagt | aaattcagac | 300 |
| aaaagaacac | aagacatttg | agcatccaca | tgaaaacaa | acatatttac | aaaacataaa | 360 |
| caaggatata | aaaccacaat | cataaccata | agcatgcatc | gtttatttgc | atttcaatag | 420 |
| atcaatccaa | agaaccatt | tctataaaca | ctatcctcta | tcaacagttt | acctaaacta | 480 |
| aagaaatatt | atccatacaa | waagcatcaa | acttgcatgt | ctttgtacct | ttcttttggt | 540 |
| ggcagcagta | ccacttccat | cggacttctc | agcctcagcc | ttgagatcaa | ccttcaagtc | 600 |
| ctcaacaaca | ctcttgctct | caagatccca | aatcttaata | ccctgctcag | tcgcagcaca | 660 |
| aagccagtac | ctattaggac | taaagcaaag | agcgtgaatc | acagagttgg | cttcaagaga | 720 |
| gtaaagcttc | ttcccctcag | ccaaatccca | gagcaaaacg | acaccgtctt | tgcctccact | 780 |
| agcacacaga | gaaccatcag | gcgacacagc | cacagtacta | acgtaaccag | tgtgaccagc | 840 |
| aagagtcgac | ctcagcttac | agttcgacaa | gttccaaact | ttcacggtct | tgtcccacga | 900 |
| cgccgacaca | atcgtcggct | ggagcgtgtt | gggactgaac | ctaacgcagc | tgacccagtc | 960 |

```
acggtgccct tcgcctcctt cggagattgt gtacttacac t                 1001
```

<210> SEQ ID NO 64
<211> LENGTH: 1001
<212> TYPE: DNA
<213> ORGANISM: Brassica napus

<400> SEQUENCE: 64

```
tccaaaaaag taaatgttta agtctagttt ctcaatctag gcaagaaaaa aaaacagttc    60
ttaccaaaat ataaaaacat tcaaaaattg ccatagatag aaaaatctat atcagatcta   120
tcgattacat tcacatattg ataaaacact agccaacaat atactgcaat ctatggcaaa   180
catgtataaa agtaaattca gacaaaagaa cacaagacat ttgagcatcc acatgaaaaa   240
caaacatatt tacaaaacat aaacaaggat ataaaaccac aatcataacc ataagcatgc   300
atcgtttatt tgcatttcaa tagatcaatc caaaagaacc atttctataa acactatcct   360
ctatcaacag tttacctaaa ctaaagaaat attatccata caataagcat caaacttgca   420
tgtctttgta cctttctttt ggtggcagca gtaccacttc catcggactt ctcagcctca   480
gccttgagat caaccttcaa rtcctcaaca cactcttgc tctcaagatc ccaaatctta    540
ataccctgct cagtcgcagc acaaagccag tacctattag gactaaagca aagagcgtga   600
atcacagagt tggcttcaag agagtaaagc ttcttcccct cagccaaatc ccagagcaaa   660
acgacaccgt ctttgcctcc actagcacac agagaaccat caggcgacac agccacagta   720
ctaacgtaac cagtgtgacc agcaagagtc gacctcagct tacagttcga caagttccaa   780
actttcacgg tcttgtccca cgacgccgac acaatcgtcg gctggagcgt gttgggactg   840
aacctaacgc agctgaccca gtcacggtgc ccttcgcctc cttcggagat tgtgtactta   900
cactccccca gagtgttcca gagcttgatc gtgcggtcac gggaggccga cacgatctga   960
cggttgtcga gcgagaaggc cacggagagg acgtctttgg t                     1001
```

<210> SEQ ID NO 65
<211> LENGTH: 1001
<212> TYPE: DNA
<213> ORGANISM: Brassica napus

<400> SEQUENCE: 65

```
tacctaaact aaagaaatat tatccataca ataagcatca aacttgcatg tctttgtacc    60
tttcttttgg tggcagcagt accacttcca tcggacttct cagcctcagc cttgagatca   120
accttcaagt cctcaacaac actcttgctc tcaagatccc aaatcttaat accctgctca   180
gtcgcagcac aaagccagta cctattagga ctaaagcaaa gagcgtgaat cacagagttg   240
gcttcaagag agtaaagctt cttcccctca gccaaatccc agagcaaaac gacaccgtct   300
ttgcctccac tagcacacag agaaccatca ggcgacacag ccacagtact aacgtaacca   360
gtgtgaccag caagagtcga cctcagctta cagttcgaca agttccaaac tttcacggtc   420
ttgtcccacg acgccgacac aatcgtcggc tggagcgtgt tgggactgaa cctaacgcag   480
ctgacccagt cacggtgccc ytcgcctcct tcggagattg tgtacttaca ctcccccaga   540
gtgttccaga gcttgatcgt gcggtcacgg gaggccgaca cgatctgacg gttgtcgagc   600
gagaaggcca cggagaggac gtctttggtg tgtccgacga atctgcgagt ggagacgccg   660
gcggcgaggt cccagagacg aagctcgccg tcccagctgc cggaaagcgc gaattggccg   720
tcggaggaga ggacgacgtc ttcgacgaag tgggagtggc cggtgaggcg tctctgggct   780
```

```
acgccgtagg atttgtcgtc ctttgtgagt ttccagacga tgatggattt gtcgcgggaa    840
gcggacacga tggtgtcgga gttgtcgatg ggggtggcga ttgcggtgac catgtcggtg    900
tgagcacgca tggtgccctt gaggacgagt ccttccgcca ttgtcgaagt ctggtgaagc    960
ttagggttat cagtttctcg ggggaggcgg agattcagac g                       1001
```

<210> SEQ ID NO 66
<211> LENGTH: 1001
<212> TYPE: DNA
<213> ORGANISM: Brassica napus

<400> SEQUENCE: 66

```
acaataagca tcaaacttgc atgtctttgt acctttcttt tggtggcagc agtaccactt     60
ccatcggact tctcagcctc agccttgaga tcaaccttca agtcctcaac aacactcttg    120
ctctcaagat cccaaatctt aataccctgc tcagtcgcag cacaaagcca gtacctatta    180
ggactaaagc aaagagcgtg aatcacagag ttggcttcaa gagagtaaag cttcttcccc    240
tcagccaaat cccagagcaa acgacaccg tctttgcctc cactagcaca cagagaacca    300
tcaggcgaca cagccacagt actaacgtaa ccagtgtgac cagcaagagt cgacctcagc    360
ttacagttcg acaagttcca aactttcacg gtcttgtccc cgacgccga cacaatcgtc    420 ggctggagcg tgttgggact gaacctaacg cagctgaccc agtcacggtg cccttcgcct    480
ccttcggaga ttgtgtactt rcactccccc agagtgttcc agagcttgat cgtgcggtca    540
cgggaggccg acacgatctg acggttgtcg agcgagaagg ccacggagag gacgtctttg    600
gtgtgtccga cgaatctgcg agtggagacg ccggcggcga ggtcccagag acgaagctcg    660
ccgtcccagc tgccggaaag cgcgaattgg ccgtcggagg agaggacgac gtcttcgacg    720
aagtgggagt ggccggtgag gcgtctctgg ctacgccgt aggatttgtc gtcctttgtg    780
agtttccaga cgatgatgga tttgtcgcgg gaagcggaca cgatggtgtc ggagttgtcg    840 atggggtgg cgattgcggt gaccatgtcg gtgtgagcac gcatggtgcc cttgaggacg    900
agtccttccg ccattgtcga agtctggtga agcttagggt tatcagtttc tcggggagg    960 cggagattca gacgaaatgg cgtcgagagg taagattcag t                       1001
```

<210> SEQ ID NO 67
<211> LENGTH: 1001
<212> TYPE: DNA
<213> ORGANISM: Brassica napus

<400> SEQUENCE: 67

```
tcagcctcag ccttgagatc aaccttcaag tcctcaacaa cactcttgct ctcaagatcc     60
caaatcttaa taccctgctc agtcgcagca caaagccagt acctattagg actaaagcaa    120
agagcgtgaa tcacagagtt ggcttcaaga gagtaaagct tcttcccctc agccaaatcc    180
cagagcaaaa cgacaccgtc tttgcctcca ctagcacaca gagaaccatc aggcgacaca    240
gccacagtac taacgtaacc agtgtgacca gcaagagtcg acctcagctt acagttcgac    300
aagttccaaa ctttcacggt cttgtcccac gacgccgaca caatcgtcgg ctggagcgtg    360
ttgggactga acctaacgca gctgacccag tcacggtgcc cttcgcctcc ttcggagatt    420
gtgtacttac actcccccag agtgttccag agcttgatcg tgcggtcacg ggaggccgac    480
acgatctgac ggttgtcgag sgagaaggcc acggagagga cgtctttggt gtgtccgacg    540
aatctgcgag tggagacgcc ggcggcgagg tcccagagac gaagctcgcc gtcccagctg    600
ccggaaagcg cgaattggcc gtcggaggag aggacgacgt cttcgacgaa gtgggagtgg    660
```

```
ccggtgaggc gtctctgggc tacgccgtag gatttgtcgt cctttgtgag tttccagacg    720
atgatggatt tgtcgcggga agcggacacg atggtgtcgg agttgtcgat ggggtggcg     780 attgcggtga ccatgtcggt gtgagcacgc atggtgccct tgaggacgag tccttccgcc    840
attgtcgaag tctggtgaag cttagggtta tcagtttctc gggggaggcg agattcaga    900 cgaaatggcg tcgagaggta agattcagtt tatatcagag acaacacaat ggattagggt    960
ttacttttat tgggctttga tgattaagtt taatgaatgg g                       1001
```

<210> SEQ ID NO 68
<211> LENGTH: 1001
<212> TYPE: DNA
<213> ORGANISM: Brassica napus

<400> SEQUENCE: 68

```
tacctattag gactaaagca aagagcgtga atcacagagt tggcttcaag agagtaaagc     60
ttcttcccct cagccaaatc ccagagcaaa acgacaccgt ctttgcctcc actagcacac    120
agagaaccat caggcgacac agccacagta ctaacgtaac cagtgtgacc agcaagagtc    180
gacctcagct tacagttcga caagttccaa actttcacgg tcttgtccca cgacgccgac    240
acaatcgtcg gctggagcgt gttgggactg aacctaacgc agctgaccca gtcacggtgc    300
ccttcgcctc cttcggagat tgtgtactta cactccccca gagtgttcca gagcttgatc    360
gtgcggtcac gggaggccga cacgatctga cggttgtcga gcgagaaggc cacggagagg    420
acgtctttgg tgtgtccgac gaatctgcga gtggagacgc cggcgcgag gtcccagaga    480 cgaagctcgc cgtcccagct kccggaaagc gcgaattggc cgtcggagga gaggacgacg    540
tcttcgacga agtgggagtg gccggtgagg cgtctctggg ctacgccgta ggatttgtcg    600
tcctttgtga gtttccagac gatgatggat tgtcgcggg aagcggacac gatggtgtcg    660
gagttgtcga ggggtggc gattgcggtg accatgtcgg tgtgagcacg catggtgccc    720
ttgaggacga gtccttccgc cattgtcgaa gtctggtgaa gcttagggtt atcagtttct    780
cgggggaggc ggagattcag acgaaatggc gtcgagaggt aagattcagt ttatatcaga    840
gacaacacaa tggattaggg tttacttta ttgggctttg atgattaagt ttaatgaatg    900
ggtcttgcgt aaatgggctt ttttttgtact ggtaagagtt ttttttggtttt acttggtgt    960 taagaattta ccaatgttcg agaatcggta actagactag c                       1001
```

<210> SEQ ID NO 69
<211> LENGTH: 1001
<212> TYPE: DNA
<213> ORGANISM: Brassica napus

<400> SEQUENCE: 69

```
cctccactag cacacagaga accatcaggc gacacagcca cagtactaac gtaaccagtg     60
tgaccagcaa gagtcgacct cagcttacag ttcgacaagt tccaaacttt cacggtcttg    120
tcccacgacg ccgacacaat cgtcggctgg agcgtgttgg gactgaacct aacgcagctg    180
acccagtcac ggtgcccttc gcctccttcg gagattgtgt acttacactc ccccagagtg    240
ttccagagct tgatcgtgcg gtcacgggag gccgacacga tctgacggtt gtcgagcgag    300
aaggccacgg agaggacgtc tttggtgtgt ccgacgaatc tgcgagtgga gacgccggcg    360
gcgaggtccc agagacgaag ctcgccgtcc cagctgccgg aaagcgcgaa ttggccgtcg    420
gaggagagga cgacgtcttc gacgaagtgg gagtggccgg tgaggcgtct ctgggctacg    480
```

| | |
|---|---|
| ccgtaggatt tgtcgtcctt kgtgagtttc cagacgatga tggatttgtc gcgggaagcg | 540 |
| gacacgatgg tgtcggagtt gtcgatgggg gtggcgattg cggtgaccat gtcggtgtga | 600 |
| gcacgcatgg tgcccttgag gacgagtcct tccgccattg tcgaagtctg gtgaagctta | 660 |
| gggttatcag tttctcgggg gaggcggaga ttcagacgaa atggcgtcga gaggtaagat | 720 |
| tcagtttata tcagagacaa cacaatggat tagggtttac ttttattggg ctttgatgat | 780 |
| taagtttaat gaatgggtct tgcgtaaatg ggcttttttt gtactggtaa gagttttttt | 840 |
| ggttttactt ggtgttaaga atttaccaat gttcgagaat cggtaactag actagcgcct | 900 |
| agacggatta ttcagaacct aaacgagatc tagatattaa cgaattatta atttatttta | 960 |
| tatttatata aaacatttta atttttaatt ataaaattat t | 1001 |

<210> SEQ ID NO 70
<211> LENGTH: 1001
<212> TYPE: DNA
<213> ORGANISM: Brassica napus

<400> SEQUENCE: 70

| | |
|---|---|
| gattcggcag gttattcctg aagatgacaa gcttaatcat cttttttttg tttcgcattg | 60 |
| gtgctaaatg tttgtgttga tatatgctgc agaagaaaac aacggagttg ttatcccgga | 120 |
| agctcataac tctgatgaag ttgagaaatt ggatacagca gaagaaggtt cattgtagca | 180 |
| tgagcatgac attttttttgt ttatgctttc tttgttcac tgtttaaaat ttggctatct | 240 |
| gtgggtcgtt tattagatgc gtaagacatt aactagtggt taagggaggg ttatactatc | 300 |
| atgagattgg atactgattc taatactagg tatcatcctt gctttgcaga cctgaaagac | 360 |
| aaggtggaag agtcagcacc ggttcctgat gagcaacaag gttcaatctt ttatcttctc | 420 |
| tttctgtctc attttctta acgtttagtt taatatatct gagtttggcg agttttattt | 480 |
| attttgctt gtcattggtg rtttcagtgt ccgaggatca tgatcaagaa gtgcaccatg | 540 |
| cagtgcataa cccagcgaaa ggttcataga tctctcattc tacagtcttc tcatcttatg | 600 |
| agcgttcatg ttgtctggtt gaagatttat ttatctcttt cgtatatttt atccattcag | 660 |
| ctaaagagaa ggcagcccaa gagaaggctg ccaaagagga agctgaagaa gaggcagaag | 720 |
| caaacaagaa aagacacttg aacgtggtgt tcatcgggca tgttggtatg gctacttgtt | 780 |
| gatttctttt catcagctct actttcataa tagatatatc atctgcactt gtttagactc | 840 |
| agggcttaaa agcgtatgta acacattctt gaaattagga tcatgagctt ttagtcggtg | 900 |
| tgttttaact tttaagcttc ttgatttaat ctttacatgg tcaccttttc aattgtagat | 960 |
| gctggaaagt ctacaattgg aggacaaatt ctcttcctta g | 1001 |

<210> SEQ ID NO 71
<211> LENGTH: 121
<212> TYPE: DNA
<213> ORGANISM: Brassica napus

<400> SEQUENCE: 71

| | |
|---|---|
| acrtttagtt taatatatct gagtttggcg agttttattt attttgctt gtcattggtg | 60 |
| rtttcagykt ccgaggatca tgatcwagaa gtgcaccatg cagtgcataa cccagcgaaa | 120 |
| g | 121 |

<210> SEQ ID NO 72
<211> LENGTH: 1001
<212> TYPE: DNA
<213> ORGANISM: Brassica napus

<400> SEQUENCE: 72

```
gaacgtggtg ttcatcgggc atgttggtat ggctacttgt tgatttcttt tcatcagctc    60
tactttcata atagatatat catctgcact tgtttagact cagggcttaa aagcgtatgt   120
aacacattct tgaaattagg atcatgagct tttagtcggt gtgttttaac ttttaagctt   180
cttgatttaa tctttacatg gtcacctttt caattgtaga tgctggaaag tctacaattg   240
gaggacaaat tctcttcctt agcggtcagg tggacgaccg acaaatccaa aagtatgaaa   300
aagaagcaaa agaaaaaagt agagaaagct ggtgggtggt tctgattaat ttgaaatgat   360
aaggaattct tttgttctct ttttcttttt gtttttataa acttgttatc gttctgtatg   420
ctaggtatat ggcttatata atggatacaa atgaagaaga gagggcgaag gtatttcctg   480
attttttatt tatgtttctt wgtgtgctat aaatgtgtca gagatgataa gaattcacgt   540
gtctgtagaa ttttcagcaa tgtttatggt tgaatttaac ttagctaact gttatgactt   600
acttgctaca ttgaacaggg caaaacagtt gaagttggaa gggctcattt tgaaactgcg   660
agtacgagat ttaccatttt ggatgctccg gtaagagacc aacttaaaag aataattttt   720
tgttcacttg tctttatgag agtattttgt tctaattctt ttgcgccttt tttgaacttg   780
tagggtcaca agagttatgt accaaatatg attagtggag catctcaagc ggacattggt   840
gtactggtaa gttattatct taatttggtc ggagtcgtta ctgtgtagtg tgcgtctttg   900
gtaggaagct tattaatttt catgtccttg tccctctgtt gtaggtgatt tcggctcgta   960
aaggtgaatt tgaaacggga tatgagaggg gtgggcagac c                     1001
```

<210> SEQ ID NO 73
<211> LENGTH: 1001
<212> TYPE: DNA
<213> ORGANISM: Brassica napus

<400> SEQUENCE: 73

```
ctacttgttg atttcttttc atcagctcta ctttcataat agatatatca tctgcacttg    60
tttagactca gggcttaaaa gcgtatgtaa cacattcttg aaattaggat catgagcttt   120
tagtcggtgt gttttaactt ttaagcttct tgatttaatc tttacatggt cacctttca    180
attgtagatg ctggaaagtc tacaattgga ggacaaattc tcttccttag cggtcaggtg   240
gacgaccgac aaatccaaaa gtatgaaaaa gaagcaaaag aaaaagtag agaaagctgg    300
tgggtggttc tgattaattt gaaatgataa ggaattcttt tgttctcttt ttcttttgt    360
ttttataaac ttgttatcgt tctgtatgct aggtatatgg cttatataat ggatacaaat   420
gaagaagaga gggcgaaggt atttcctgat ttttatttta tgtttcttag tgtgctataa   480
atgtgtcaga gatgataaga rttcacgtgt ctgtagaatt ttcagcaatg tttatggttg   540
aatttaactt agctaactgt tatgacttac ttgctacatt gaacagggca aaacagttga   600
agttggaagg ctcattttg aaactgcgag tacgagattt accattttgg atgctccggt    660
aagagaccaa cttaaaagaa taattttttg ttcacttgtc tttatgagag tattttgttc   720
taattctttt gcgcctttt tgaacttgta gggtcacaag agttatgtac caaatatgat    780
tagtggagca tctcaagcgg acattggtgt actggtaagt tattatctta atttggtcgg   840
agtcgttact gtgtagtgtg cgtctttggt aggaagctta ttaattttca tgtccttgtc   900
cctctgttgt aggtgatttc ggctcgtaaa ggtgaatttg aaacgggata tgagaggggt   960
gggcagaccc gtgaacatgt tcaacttgca aaacattgg g                      1001
```

<210> SEQ ID NO 74
<211> LENGTH: 1001
<212> TYPE: DNA
<213> ORGANISM: Brassica napus

<400> SEQUENCE: 74

| | | | | | |
|---|---|---|---|---|---|
| tcagctctac | tttcataata | gatatatcat | ctgcacttgt | ttagactcag | ggcttaaaag | 60 |
| cgtatgtaac | acattcttga | aattaggatc | atgagctttt | agtcggtgtg | ttttaacttt | 120 |
| taagcttctt | gatttaatct | ttacatggtc | accttttcaa | ttgtagatgc | tggaaagtct | 180 |
| acaattggag | gacaaattct | cttccttagc | ggtcaggtgg | acgaccgaca | aatccaaaag | 240 |
| tatgaaaaag | aagcaaaaga | aaaagtagaa | aaagctggt | gggtggttct | gattaatttg | 300 |
| aaatgataag | gaattctttt | gttctctttt | tcttttttgtt | tttataaact | tgttatcgtt | 360 |
| ctgtatgcta | ggtatatggc | ttatataatg | gatacaaatg | aagaagagag | ggcgaaggta | 420 |
| tttcctgatt | ttttatttat | gtttcttagt | gtgctataaa | tgtgtcagag | atgataagaa | 480 |
| ttcacgtgtc | tgtagaattt | ycagcaatgt | ttatggttga | atttaactta | gctaactgtt | 540 |
| atgacttact | tgctacattg | aacagggcaa | acagttgaa | gttggaaggg | ctcattttga | 600 |
| aactgcgagt | acgagattta | ccattttgga | tgctccggta | agagaccaac | ttaaaagaat | 660 |
| aatttttgt | tcacttgtct | ttatgagagt | attttgttct | aattcttttg | cgccttttt | 720 |
| gaacttgtag | ggtcacaaga | gttatgtacc | aaatatgatt | agtggagcat | ctcaagcgga | 780 |
| cattggtgta | ctggtaagtt | attatcttaa | tttggtcgga | gtcgttactg | tgtagtgtgc | 840 |
| gtctttggta | ggaagcttat | taattttcat | gtccttgtcc | ctctgttgta | ggtgatttcg | 900 |
| gctcgtaaag | gtgaatttga | acgggatat | gagagggtg | ggcagacccg | tgaacatgtt | 960 |
| caacttgcaa | aaacattggg | cgtgtcgaag | ctggttgtcg | t | | 1001 |

<210> SEQ ID NO 75
<211> LENGTH: 1001
<212> TYPE: DNA
<213> ORGANISM: Brassica napus

<400> SEQUENCE: 75

| | | | | | |
|---|---|---|---|---|---|
| gctctacttt | cataatagat | atatcatctg | cacttgttta | gactcagggc | ttaaaagcgt | 60 |
| atgtaacaca | ttcttgaaat | taggatcatg | agcttttagt | cggtgtgttt | taacttttaa | 120 |
| gcttcttgat | ttaatcttta | catggtcacc | ttttcaattg | tagatgctgg | aaagtctaca | 180 |
| attggaggac | aaattctctt | ccttagcggt | caggtggacg | accgacaaat | ccaaaagtat | 240 |
| gaaaagaag | caaagaaaa | agtagagaa | agctggtggg | tggttctgat | taatttgaaa | 300 |
| tgataaggaa | ttcttttgtt | ctcttttct | ttttgtttt | ataaacttgt | tatcgttctg | 360 |
| tatgctaggt | atatggctta | taatggat | acaaatgaag | aagagagggc | gaaggtattt | 420 |
| cctgattttt | tatttatgtt | tcttagtgtg | ctataaatgt | gtcagagatg | ataagaattc | 480 |
| acgtgtctgt | agaattttca | rcaatgttta | tggttgaatt | taacttagct | aactgttatg | 540 |
| acttacttgc | tacattgaac | agggcaaaac | agttgaagtt | ggaagggctc | attttgaaac | 600 |
| tgcgagtacg | agatttacca | ttttggatgc | tccggtaaga | gaccaactta | aaagaataat | 660 |
| ttttgttca | cttgtcttta | tgagagtatt | tgttctaat | tcttttgcgc | cttttttgaa | 720 |
| cttgtagggt | cacaagagtt | atgtaccaaa | tatgattagt | ggagcatctc | aagcggacat | 780 |
| tggtgtactg | gtaagttatt | atcttaattt | ggtcggagtc | gttactgtgt | agtgtgcgtc | 840 |
| tttggtagga | agcttattaa | ttttcatgtc | cttgtccctc | tgttgtaggt | gatttcggct | 900 |

```
cgtaaaggtg aatttgaaac gggatatgag aggggtgggc agacccgtga acatgttcaa    960
cttgcaaaaa cattgggcgt gtcgaagctg gttgtcgttg t                        1001
```

<210> SEQ ID NO 76
<211> LENGTH: 1001
<212> TYPE: DNA
<213> ORGANISM: Brassica napus

<400> SEQUENCE: 76

```
ggtcaccttt tcaattgtag atgctggaaa gtctacaatt ggaggacaaa ttctcttcct     60
tagcggtcag gtggacgacc gacaaatcca aaagtatgaa aaagaagcaa agaaaaaag    120 tagagaaagc tggtgggtgg ttctgattaa tttgaaatga taaggaattc ttttgttctc    180
tttttctttt tgtttttata aacttgttat cgttctgtat gctaggtata tggcttatat    240
aatggataca aatgaagaag agagggcgaa ggtatttcct gattttttat ttatgtttct    300
tagtgtgcta taaatgtgtc agagatgata agaattcacg tgtctgtaga attttcagca    360
atgtttatgg ttgaatttaa cttagctaac tgttatgact tacttgctac attgaacagg    420
gcaaaacagt tgaagttgga agggctcatt ttgaaactgc gagtacgaga tttaccattt    480
tggatgctcc ggtaagagac maacttaaaa gaataatttt ttgttcactt gtctttatga    540
gagtattttg ttctaattct tttgcgcctt ttttgaactt gtagggtcac aagagttatg    600
taccaaatat gattagtgga gcatctcaag cggacattgg tgtactggta agttattatc    660
ttaatttggt cggagtcgtt actgtgtagt gtgcgtcttt ggtaggaagc ttattaattt    720
tcatgtcctt gtccctctgt tgtaggtgat ttcggctcgt aaaggtgaat tgaaacggg    780 atatgagagg ggtgggcaga cccgtgaaca tgttcaactt gcaaaaacat gggcgtgtc    840 gaagctggtt gtcgttgtga acaaaatgga tgatccaact gtgaactggt cgaaagagag    900
gtatgtgcat tatcctttcg aattcatgct actgttttc gtatctactt ccattcatcc    960
gcgtatgtac tcttgtgcag gtacgatgaa atagaacaaa a                      1001
```

<210> SEQ ID NO 77
<211> LENGTH: 1001
<212> TYPE: DNA
<213> ORGANISM: Brassica napus

<400> SEQUENCE: 77

```
tcaattgtag atgctggaaa gtctacaatt ggaggacaaa ttctcttcct tagcggtcag     60
gtggacgacc gacaaatcca aaagtatgaa aaagaagcaa agaaaaaag tagagaaagc    120 tggtgggtgg ttctgattaa tttgaaatga taaggaattc ttttgttctc ttttctttt    180 tgttttata aacttgttat cgttctgtat gctaggtata tggcttatat aatggataca    240
aatgaagaag agagggcgaa ggtatttcct gattttttat ttatgtttct tagtgtgcta    300
taaatgtgtc agagatgata agaattcacg tgtctgtaga attttcagca atgtttatgg    360
ttgaatttaa cttagctaac tgttatgact tacttgctac attgaacagg gcaaaacagt    420
tgaagttgga agggctcatt ttgaaactgc gagtacgaga tttaccattt tggatgctcc    480
ggtaagagac caacttaaaa saataatttt ttgttcactt gtctttatga gagtattttg    540
ttctaattct tttgcgcctt ttttgaactt gtagggtcac aagagttatg taccaaatat    600
gattagtgga gcatctcaag cggacattgg tgtactggta agttattatc ttaatttggt    660
cggagtcgtt actgtgtagt gtgcgtcttt ggtaggaagc ttattaattt tcatgtcctt    720
```

```
gtccctctgt tgtaggtgat ttcggctcgt aaaggtgaat ttgaaacggg atatgagagg    780
ggtgggcaga cccgtgaaca tgttcaactt gcaaaaacat tgggcgtgtc gaagctggtt    840
gtcgttgtga acaaaatgga tgatccaact gtgaactggt cgaaagagag gtatgtgcat    900
tatcctttcg aattcatgct actgttttc gtatctactt ccattcatcc gcgtatgtac    960
tcttgtgcag gtacgatgaa atagaacaaa aaatggtacc a                      1001

<210> SEQ ID NO 78
<211> LENGTH: 1001
<212> TYPE: DNA
<213> ORGANISM: Brassica napus

<400> SEQUENCE: 78
aaagtctaca attggaggac aaattctctt ccttagcggt caggtggacg accgacaaat     60
ccaaaagtat gaaaaagaag caaagaaaa aagtagagaa agctggtggg tggttctgat    120
taatttgaaa tgataaggaa ttcttttgtt ctcttttct ttttgttttt ataaacttgt    180
tatcgttctg tatgctaggt atatggctta tataatggat acaaatgaag aagagagggc    240
gaaggtattt cctgattttt tatttatgtt tcttagtgtg ctataaatgt gtcagagatg    300
ataagaattc acgtgtctgt agaattttca gcaatgttta tggttgaatt taacttagct    360
aactgttatg acttacttgc tacattgaac agggcaaaac agttgaagtt ggaagggctc    420
attttgaaac tgcgagtacg agatttacca ttttggatgc tccggtaaga gaccaactta    480
aaagaataat ttttttgttca yttgtcttta tgagagtatt tgttctaat tcttttgcgc    540 cttttttgaa cttgtagggt cacaagagtt atgtaccaaa tatgattagt ggagcatctc    600
aagcggacat tggtgtactg gtaagttatt atcttaattt ggtcggagtc gttactgtgt    660
agtgtgcgtc tttggtagga agcttattaa ttttcatgtc cttgtccctc tgttgtaggt    720
gatttcggct cgtaaaggtg aatttgaaac gggatatgag aggggtgggc agacccgtga    780
acatgttcaa cttgcaaaaa cattgggcgt gtcgaagctg gttgtcgttg tgaacaaaat    840
ggatgatcca actgtgaact ggtcgaaaga gaggtatgtg cattatcctt tcgaattcat    900
gctactgttt tcgtatctta cttccattca tccgcgtatg tactcttgtg caggtacgat    960
gaaatagaac aaaaaatggt accatttctt aaatcctctg g                      1001

<210> SEQ ID NO 79
<211> LENGTH: 1001
<212> TYPE: DNA
<213> ORGANISM: Brassica napus

<400> SEQUENCE: 79
ctcttcctta gcggtcaggt ggacgaccga caaatccaaa agtatgaaaa agaagcaaaa     60
gaaaaaagta gagaaagctg gtgggtggtt ctgattaatt tgaaatgata aggaattctt    120
ttgttctctt tttctttttg tttttataaa cttgttatcg ttctgtatgc taggtatatg    180
gcttatataa tggatacaaa tgaagaagag agggcgaagg tatttcctga ttttttattt    240
atgtttctta gtgtgctata aatgtgtcag agatgataag aattcacgtg tctgtagaat    300
tttcagcaat gtttatggtt gaatttaact tagctaactg ttatgactta cttgctacat    360
tgaacagggc aaaacagttg aagttggaag ggctcatttt gaaactgcga gtacgagatt    420
taccattttg gatgctccgg taagagacca acttaaaaga ataatttttt gttcacttgt    480
ctttatgaga gtattttgtt ytaattcttt tgcgcctttt ttgaacttgt agggtcacaa    540
gagttatgta ccaaatatga ttagtggagc atctcaagcg gacattggtg tactggtaag    600
```

```
ttattatctt aatttggtcg gagtcgttac tgtgtagtgt gcgtctttgg taggaagctt      660
attaattttc atgtccttgt ccctctgttg taggtgattt cggctcgtaa aggtgaattt      720
gaaacgggat atgagagggg tgggcagacc cgtgaacatg ttcaacttgc aaaaacattg      780
ggcgtgtcga agctggttgt cgttgtgaac aaaatggatg atccaactgt gaactggtcg      840
aaagagaggt atgtgcatta tcctttcgaa ttcatgctac tgttttttcgt atctacttcc    900 attcatccgc gtatgtactc ttgtgcaggt acgatgaaat agaacaaaaa atggtaccat      960
ttcttaaatc ctctggctac aacacaaaga aaggtatgca g                         1001

<210> SEQ ID NO 80
<211> LENGTH: 760
<212> TYPE: DNA
<213> ORGANISM: Brassica napus

<400> SEQUENCE: 80
aattcttttg ttctcttttt cttttttgttt ttataaactt gttatcgtct tgtatgctag     60
gtatatggct tatataatgg atacaaatga agaagagagg gcgaaggtat ttcctgattt     120
ttttatttat gtttctttgt gtgctataaa tgtgtcagag atgataagag ttcacgtgtc     180
tgtagaattt tcagcaatgt ttatggttga atttaactta gctaactgtt atgacttact    240
tgctacattg aacagggcaa aacagttgaa gttggaaggg ctcatttttga aactgcgagt    300 acgagattta ccattttgga tgctccggta agagacmaac ttaaaasaat aattttttgt     360
tcacttgtct ttatgagagt attttgttct aattcttttg cgccttttttt gaacttgtag    420 ggtcacaaga gttatgtacc aaatatgatt agtggagcat ctcaagcgga cattggtgta    480
ctggtaagtt attatcttaa tttggtcgga gtcgttactg tgtagtgtgc gtctttggta    540
ggaagcttat taattttcat gtccttgtcc ctctgttgta ggtgatttcg gctcgtaaag    600
gtgaatttga aacgggatat gagagggtg ggcagacccg tgaacatgtt caacttgcaa      660
aaacattggg cgtgtcgaag ctggttgtcg ttgtgaacaa aatggatgat ccaactgtga    720
actggtcgaa agagaggtat gtgcattatc ctttcgaatt                           760

<210> SEQ ID NO 81
<211> LENGTH: 201
<212> TYPE: DNA
<213> ORGANISM: Brassica napus

<400> SEQUENCE: 81
ccagakgcaa aacygaatgt aagagaacat tactattaga aatcgagatc aagcttcctc      60
ttcagatgag atctatcggc actacaaaat gaacaacaac ragaagcttt taaaacacat    120
wcaakcttga gmctgtaaaa acaactaatc aaagagatcg ctctatttgc wcmtggtgat   180
ggttggtcgg kkaggaggcc g                                               201

<210> SEQ ID NO 82
<211> LENGTH: 121
<212> TYPE: DNA
<213> ORGANISM: Brassica napus

<400> SEQUENCE: 82
yagaaactgg tcgatgaggt aaccatgtgc accgtgaacc tccaccccat caaagcctat      60
rawtamcaca agtgtcatgt tcagctaaca tyatacatcc aaagggggaaa aagacttttc   120 t                                                                     121
```

<210> SEQ ID NO 83
<211> LENGTH: 121
<212> TYPE: DNA
<213> ORGANISM: Brassica napus

<400> SEQUENCE: 83 ratgcattttt cttcatcatt ggtaacatgg tgctttatgt yaacaataaa acctcttaat    60
ragctctaac tgattcgtaa tgaaaccaaa catatataaa taaacaatct tagatttgat   120
g                                                                  121

<210> SEQ ID NO 84
<211> LENGTH: 121
<212> TYPE: DNA
<213> ORGANISM: Brassica napus

<400> SEQUENCE: 84
gtcttttatc ttatttcaaa atatattagg tgtgacatgt gaaaaggttc tagaaactgg    60
ktggttatgc ttcctagact ccatcaagaa ataaagctga attgtttttt tacmcatcca   120
c                                                                  121

<210> SEQ ID NO 85
<211> LENGTH: 121
<212> TYPE: DNA
<213> ORGANISM: Brassica napus

<400> SEQUENCE: 85
aaactggktg gttatgcttc ctagactcca tcaagaaata aagctgaatt gttttttttac    60 mcatccactc atttttkatc aaacaggtac aagagaagaa gatcaagaaa atttctgaaa   120
t                                                                  121

<210> SEQ ID NO 86
<211> LENGTH: 121
<212> TYPE: DNA
<213> ORGANISM: Brassica napus

<400> SEQUENCE: 86
yactgcgata tcatctccta ttatacycca tgtttctttg aagaactctg ysgtataacc    60
rtctggccct ggagctttgc ttcctggcat cttaaataaa actcctttga tttcttcttt   120 r                                                                  121

<210> SEQ ID NO 87
<211> LENGTH: 121
<212> TYPE: DNA
<213> ORGANISM: Brassica napus

<400> SEQUENCE: 87
attattagtt tttccaaaat caaatgttat tagattgtac atataaaaaa aaacctaaga    60
raaaamaact catctcattc ttttatacta agakggtcta aagaaattaa tgatataaaa   120
a                                                                  121

<210> SEQ ID NO 88
<211> LENGTH: 1001
<212> TYPE: DNA
<213> ORGANISM: Brassica napus

<400> SEQUENCE: 88
ctatgtgtag tagataaagt atggtactga ccataggtat gtgacatttt agtttatatt    60

```
gaatgttaat atttgatatt gtatgctaac tataaacaca tgtgttattt taatagttga      120
accacaacca aagtcagcct ctatacatga ttacatccag ctggagatta catgacacat      180
gcaccagagg catacacact tggatctcta atcctaacac ctccaattac aggccaaaga      240
agacaaggat gttgttaaaa ggtgaattca aggtagacct aagctaactt cagctgatac      300
tgaacttgca ctgatgtgat tgttattaat atcattaatc gttattgaaa gttctcaaca      360
tcaaattgat tgttcatgaa acaaggtgtc atagggtgaa gagaaagaac ctgtaggaag      420
tgtggtgaaa ctgatcacag tcgcgctctc tgcaaaataa tgtataacac tattacttag      480
cggttacaca ttagttttga rccttgaagt tcacttgaaa acacgtagga gagaagcaaa      540
tagaacagcc actagcgtga tgcagatagg aatgcctata acatgtgtg cagttgtatt       600 cttgagaagg tggatgatat ggcagatcct tgtggcttga tgattcagta cataaaaggg      660
catatcagtt tctttgaaaa aggttctttg ttgtacctat aaaagaaagg agattgtttc      720
aaaaaagaac tacataaatc atgctagaga ctggatccag agtataaata ttcacctctt      780
cgtttggttt gtccctaaaa tgttctacag aatcagcttc ttcaagggaa tcacatccgt      840
gtgcatcaag aaactgtaga ctcagtggga gttttttccac tgatctgaga ttcttgcagt     900
tattaaggca aagagttacc agtgaggtaa gatctctgat gcttgatggc aatgcaacaa      960
actcatggcc gctgagatct aaatttgtca acttaatgaa a                         1001

<210> SEQ ID NO 89
<211> LENGTH: 201
<212> TYPE: DNA
<213> ORGANISM: Brassica napus

<400> SEQUENCE: 89
gagaaagaac ctgtaggaag tgtggtgaaa ctgatcacag tcgcgctctc tgcaaaataa       60
tgtataacac tattacttag cggttacaca ttagttttga rccttgaagt tcacttgaaa      120
acacgtagra gagaagcaam tagaacagcs actagcgtga tgcagatagg aatgcctata      180
aacatgwgtg cagttgtatt c                                                201

<210> SEQ ID NO 90
<211> LENGTH: 301
<212> TYPE: DNA
<213> ORGANISM: Brassica napus

<400> SEQUENCE: 90
aatggaactt cagttgataa tggagtwtat gaaggargga acacttgaag tcttccctgt       60
cttctatgga gttgatcctt ccaccgtcag gcatcagcta gggagtttct ctttagaacg      120
gtacaagggt cgtccagaaa tggtgcacaa rgttcacaag tggagagaag ctcttcacct      180
aatagctaac ctttcaggcc tggattcaag acaytggtaa gctcttctta ccataatata      240
gttacaaaaa tatatatact tacgtctttt ctttaaaaat atattttcta gtgttttcac      300
a                                                                      301

<210> SEQ ID NO 91
<211> LENGTH: 229
<212> TYPE: DNA
<213> ORGANISM: Brassica napus

<400> SEQUENCE: 91
tttaaattta gtgactaaac cagaatgaga caggtgaaac tcctagcgag atactattac       60
```

```
cttacgcgct tgattagtt tgttttgagt ctctagcttt gcacgttgct ccctcctcct    120
cataattgca tggagctgct tcrcattgac aaagacaggc tcatcttcaa tgaggtccag    180
tggtaaagga acccgaccca ccatttgggg attccatacc tgcaggtct               229

<210> SEQ ID NO 92
<211> LENGTH: 229
<212> TYPE: DNA
<213> ORGANISM: Brassica napus

<400> SEQUENCE: 92
tttaaattta gtgactaaac cagaatgaga caggtgaaac tcctagckag atactattac    60
cttacgcgct tgattagtt tgttttgagt ctctagcttt gcacgttgct ccctcctcct    120
cataattgca tggagctgct tcgcattgac aaagacaggc tcatcttcaa tgaggtccag    180
tggtaaagga acccgaccca ccatttgggg attccatacc tgcaggtct               229

<210> SEQ ID NO 93
<211> LENGTH: 121
<212> TYPE: DNA
<213> ORGANISM: Brassica napus

<400> SEQUENCE: 93
aaccaaaaga gtgtgcggtt tgatactcaa agtagtagtg atcttgaaac tgtggtgaga    60 yctttggta aacacawctc gcaagtgttg ttttgccaac tytttcctca ccacaaatgc    120
c                                                                    121

<210> SEQ ID NO 94
<211> LENGTH: 121
<212> TYPE: DNA
<213> ORGANISM: Brassica napus

<400> SEQUENCE: 94
ctcaaatatc tgaaaatyta caaccacagg cgttacaaaa gtttagattc waggacacag    60
rgcaatccaa acgaaatttt acaaccttat aaacttagat tgctacagtg ggatgcatat   120
c                                                                    121

<210> SEQ ID NO 95
<211> LENGTH: 970
<212> TYPE: DNA
<213> ORGANISM: Brassica napus

<400> SEQUENCE: 95
aaccggagat gaccatcatt acctagctat tgcccatcgt cttacataga agaagcacac    60
ccaaacatag agcaaaagcc attagtttca aggtttcgga gctaaaacgg tctgtgtaga   120
ttgttctgac actcctcatc cctcgatcaa gcgtattcaa tatcttaggt ttctggatgc   180
aagcacatag ctgtacctat taaacgaaat aaaaggaagt tagctttgcg tatagagatt   240
gagagaataa ggattacagt agagggttgt tttacctctt cactacgtct tcctgatgga   300
aaacgagtga attgacttaa aaactgattc ggttggaagc aagggctgag atcaaggtca   360
tcaacagaat gatcaactga aagggagaaa gtttctaagg acatgcagcc atgtgaatat   420
aggtgcttaa tgctcaatgg aagctctgaa agtgatttta gtttcatgca atagttgagg   480
cagagagtta tcagcgagga kaggtctttg atgcttgtag gcactgtttc aaatcgtgg    540 cgactgatat ctaaatacgt caactttgta aaaaaccgaa gctgatccga caatgtctcg   600 acatgttttgc agttgtcaag acgaagctca agcaaattgt attttccatg gtcttgttct   660
```

```
gcctgcgaaa tgctcaccaa tgtgtggagg ttggtacaat cagaaagtgt gagcgtctcc      720
agctgatata gttgtggcaa agcttcaagt ctacgacagt tacaaagcct cacatgtttt      780
aacttcgtaa gatgagtcat tgatgaaggt aaaccccctga agaagtttcc acttaggttc     840
```
```
aacttctcta gaacttgcat gtgatgaatg tcatctggta tttcttcgat gtttaagttg      900
attagattta gctccatcaa ccagggaaaa tatgaaaagc tataacactc gaaaggatcc      960
ctttgctcac                                                             970
```

<210> SEQ ID NO 96
<211> LENGTH: 201
<212> TYPE: DNA
<213> ORGANISM: Brassica napus

<400> SEQUENCE: 96

```
gataaaatgg tttgattgat aagtaacctt gcaaatgtag gaaacatatt aagaacagaa       60
agcttcaact tcaattctat tgagagaaag aaaaaagcca yaagaagca aatactgyac       120 ctctcctgca taatgcgata tcgtaaaatc agtctgagag agcttcggtt tggaaaatct      180
ctcgtgacct tgaacgtct g                                                 201
```

<210> SEQ ID NO 97
<211> LENGTH: 301
<212> TYPE: DNA
<213> ORGANISM: Brassica napus

<400> SEQUENCE: 97

```
acatgtgtat gataaatcaa ttgcaaaaca agaaaaatat attatttgtc catcaagaaa       60
ctgataccct tgatgactaaa ttttgtagct ttggggtctt tctgagcaga cgtggcagaa    120
cttgccagct tttatccttg tcgctctcga rtgataaagt aacgaggttg tcgaatgtga      180
agatcaattt gcagccgaaa tgaagcgcct aatgcatgta ttatcgaaac cataagcata      240
tatacagata tatatattca taatagattt atgaattaat tttattttag ttttactatt      300
t                                                                      301
```

<210> SEQ ID NO 98
<211> LENGTH: 121
<212> TYPE: DNA
<213> ORGANISM: Brassica napus

<400> SEQUENCE: 98

```
acaataaatt tataattgtt aaccragtgg tcttggccta gtggtaaatg agttctacct       60
rgagtttctg ccctaggttc gattcccgga ttaagtggca agaaaaaccg gatttatatg     120
g                                                                      121
```

<210> SEQ ID NO 99
<211> LENGTH: 698
<212> TYPE: DNA
<213> ORGANISM: Brassica napus

<400> SEQUENCE: 99

```
agctttcaca aatctccacc agcttggttt aagcccaacc ttggcccatc cgacaaccct       60
agtgccgaca gcttcctccc ttgtctcttt gtctttcttg tgaaatgaga aagtcgatct     120
tgactctctc tctctcttcc tcgtctctct cactcgcgac ccttctccgc cgattcggac      180
ttggtgtcgt cgtgaggagt tataggttgc tctgcctcgc aaccgtagct ccatgaaggt      240
```

```
ctcgtcagct ccaccgcgat ggcgtcgcat ctccttctct ccattcttcc ctcgaagtyt    300
cttcgccgaa cggcgatttg cttctctgat gatggctcac accatcgtga ctccatcatc    360
tttcctccct aatatcccca ggtacatcta atctctcctc ttcatgagcg attaggatca    420
tctgttaggg atactaagtg agtcttgtgg gaacttgagc taacttgagg attctttgcc    480
tttgcatgtc gtctcaggtg actcgtgact ctatctctag tcgcgattga gaacctgaca    540
tgtcggtaag ctcttgcctg agctccatca tcacgctcta cctctttcgt agataacgta    600
agctcatgtc ttaacgaacc ttctctaata tgcttttcac ttgtcgatct gactcttctg    660
tttctgtttc agaagccggt ttagctctgt gacgagct                            698

<210> SEQ ID NO 100
<211> LENGTH: 749
<212> TYPE: DNA
<213> ORGANISM: Brassica napus

<400> SEQUENCE: 100
agcttctggg cagaggcagc atctactgct atccatgtga tcaatagatc acctaactct     60
acactcgagt tcagaatgcc tgaagaattg tggaccggcg cgaaacctga cttgggacat    120
ctaagaactt ttggatgcac tgcgtatgtc cacataactg aggagaaaac aggacctaga    180
gccatcaaag gggtgtttgt ggggtaccct atgggtacta aaggctatcg agtttggata    240
gaggatgarg gcagatgcag aacaagtaga aatgttgttt caacgaagaa cgagctatac    300
aagcacaccg ttgctaaagc aaaagaaagc acaggagtga ctaaagatac agagaaacga    360
gctaaaaaga gggtctcatt cagtgatgat ttgatcagag ggccttctcc ttctgtcgaa    420
tccaaagaca catctgatca aggtggagaa gaatcatcat catctgagga gtcgagtagt    480
tcgagtgacc aagaacagaa tgacgaggtt gaaagtgaaa gtggtgacac tggatcttta    540
gacacctatg ttctagctcg agacagagca agaagacaga acgtgaggcc cccatctcgc    600
tatgaggatg gaaactttgt agcctatgcg ctaaatgtca tcaacgactt agaggttgaa    660
gaacctaaat cctacgctga ggcaatgaaa agtccacaga gaagttgtg gaaaaatgca    720 gctgaggagg agatggaatc tcataggaa                                      749

<210> SEQ ID NO 101
<211> LENGTH: 574
<212> TYPE: DNA
<213> ORGANISM: Brassica napus

<400> SEQUENCE: 101
aattcttgaa gctagttgca gatttaaaca atttgcaagt tgaagtatcc gaggaagttc     60
aagctatcct attgctaagt tctctaccaa acaagtatga tcaactcaaa gagactctca    120
agtatggaag agacacccta agcctagctg aggttacagg ggctgcaagg tcgaaagaaa    180
gagagttgat tgagagtggt aagtttacca ggtctggtgg agaaggtctg atggtgacag    240
acagaggaag atcagaccaa cgctctggca aaggaaatgg aaaatcctac aggggaagat    300
ccaagagcag acagggacgt tccaagtcgc gtcctaggaa caccaaaggc tcaaagggat    360
gttttgtatg cgggaaggag ggccactgga agcgtgactg ccctgataag aaaccttaca    420
aaacgccaga ctcagcaaat gttgtggcag agtccaakga acctctaatc ctcaccgtga    480
gcacccaata ctccaaggac gaatgggtga tggactctgg ctgctcgttc cacatcacac    540
cagacaagag ttttttgttt gacctggaag aatt                                574
```

<210> SEQ ID NO 102
<211> LENGTH: 524
<212> TYPE: DNA
<213> ORGANISM: Brassica napus

<400> SEQUENCE: 102

| | | |
|---|---|---|
| agcttctcat cggtgagaat agctttcagt ccaagcactc caaagtgagc aagcattctc | 60 |
| actttccata gggcgaagtc accatctcct tcgaaacggt cgatctcgat gcgttccttt | 120 |
| gacttcaccw ttgagaaggt actgagtatg cacctcctct gtctctctct ctatcctaag | 180 |
| caaccttgat gaaaaccgga gctctgatac cacttgtaga atgtaattag ctcaggttaa | 240 |
| cttaggttag aggttatatt gatctaggtc taatactgaa agtaaagaca caagcgattt | 300 |
| aacgacttcc cggccctcgg cgcggtacgt gtcgtgggag aacttctgct cccaaaatcc | 360 |
| actagatcaa agagtctcta gcaccactaa atcagtgtgc tagataggta ggttacaata | 420 |
| agatcccttc aacttagcta gggaatacaa caaccttaat atgagacaat agccttaagt | 480 |
| ctaagctagt tgtccttgtt gaagtctcct ttcccttgat gctg | 524 |

<210> SEQ ID NO 103
<211> LENGTH: 681
<212> TYPE: DNA
<213> ORGANISM: Brassica napus

<400> SEQUENCE: 103

| | | |
|---|---|---|
| aaagtgagca agcattctca ctttccatag ggcgaagtca ccatctcctt cgaaacggtc | 60 |
| gatctcgatg cgttcctttg acttcaccat tgagaaggta ctgagtatgc acctcctctg | 120 |
| tctctctctc tatcctaagc aaccttgatg aaaaccggaa gctctgatac cacttgtaga | 180 |
| atgtaattag ctcaggttaa cttaggttag aggttatatt gatctaggtc taatactgaa | 240 |
| agtaaagaca caagcgattt aacgacttcc cggccctcgg ctcggtacgt gtcgtgggag | 300 |
| aacttctgct cccaaaatcy actagatyaa agagtctcta gcaccactaa atcagtgtgc | 360 |
| tagataggta ggttacaata agatcccttc aacttagcta gggaatacaa caaccttaat | 420 |
| atgagacaat agccttaagt ctaagctagt tgtccttgtt gaagtctcct ttcccttgat | 480 |
| gctgtatctt gttgactgat ctctgatgct ataacctgct gttgttgctt ctatccggta | 540 |
| accctaatca cccatactaa cattgtatat atatgtgtcg tatgtgatca ggtagtgcaa | 600 |
| cctggagtgg gcctgcgcat gacttcggcc catcagatgt gatgctgctg ctggcccatc | 660 |
| acgcagggat aaacccaagc t | 681 |

<210> SEQ ID NO 104
<211> LENGTH: 519
<212> TYPE: DNA
<213> ORGANISM: Brassica napus

<400> SEQUENCE: 104

| | | |
|---|---|---|
| gctgcaatcg cctttgtgg gaggttgatg caagggaata gatacatagc tccttcagct | 60 |
| ctgttgcatg ttacaccktc taacttgttc aaagcttctt caagggtctg tgtggctcaa | 120 |
| ctcaaaactc attaaaacca taacaaaaat ctagttccat gattgctagt aagttctgtg | 180 |
| agaatggcta acctttgcac gtgttgctaa agacgagagg atcccctctt tctctgctat | 240 |
| gtatgaatca tacgagtcat caccaggctg atcaaattac attaaagagc tgttaaagac | 300 |
| aattgagctt ttaaaccaaa ccagctgtta aagtaataca ataccttggg agggctcatg | 360 |
| acgaggctgg cgagaatttg accagagatg ttggagcaaa gattgacaga agccactttg | 420 |

```
tatatctgtt ctcttacatc agaagtgaat ccggtaacct ccatgtaacc gcctctcttc      480
ccacactctc cataataccc tattgaaaga aaggagtac                             519

<210> SEQ ID NO 105
<211> LENGTH: 946
<212> TYPE: DNA
<213> ORGANISM: Brassica napus

<400> SEQUENCE: 105
tatatgttct gaacctcact acaattcagc atctgagctt gttttttttt ctttcttcta       60
gtggtgtaag attttgttta accaatggat gttgcaattt ttctatcagt tcggattcta      120
ttgatcgtgc ttggaagatc ctcgaccaaa tccccgggaa agctaccggt gcttacagcc      180
acagccaggt tttgtggcct tgtcaatct  taaacagtga atgatggatg atacactctc      240
ttaatcttct gctttgtctc tcagggtatc aagggactac gtgatcgat  agctgctgga      300 atcgaagccc gtgacggttt ccctgctgat cctaatgata ttttcatgac agatggtgca      360
agccctgggg taaccagtca tcaaactttc cctaaactta tataaattac agaaaaaagg      420
ttagtaatgt tactctcgtt cttttaggtt cacatgatga tgcaactcct cataagttca      480
gagaaagatg gaatcctttg ycctattcct cagtacccct tgtactcagc ttctattgcc      540
cttcacggcg gtagtctggt atgttccttt atgtctctct gatgcatgtc tatagtgact      600
tctgattgct gtcatcttct tgaggtaggt tccatactac ctagacgaag catcagggtg      660
gggtcttgaa atatctgagc tgaagaagca gcttgaggat gctaagtcaa aaggcatcac      720
tgtaagagcc ttggcggtta ttaaccctgg taaccctaca ggacaggtaa agactaaacc      780
acaaatctat ttccatccaa attcaacact ttgtctgaac tctagcctgt tattttcctg      840
gttaaaggtt ctgtcagaag aaaaccagcg tgacattgtt gatttctgta agaaagaagg      900
cttggtgctt ctagcagacg aggtttatca ggaaacgttt acgtcc                    946

<210> SEQ ID NO 106
<211> LENGTH: 121
<212> TYPE: DNA
<213> ORGANISM: Brassica napus

<400> SEQUENCE: 106
tctcgtgacc cataatcaag cattgaatat atattctgag agaagccata tatattcaaa       60
ytaattaaaa actaatmtat tcwgaaagta twgtgaaata ttgaatatta cgagcaagta     120
g                                                                     121

<210> SEQ ID NO 107
<211> LENGTH: 121
<212> TYPE: DNA
<213> ORGANISM: Brassica napus

<400> SEQUENCE: 107
atcaacaaga gaaaagctaa caagacttgc acataaytct aaacaggaag aaaaactgag       60
yagaacatga acagagacca aaaggtccaa aactgatttg atttaagggc cagtttgaat      120
a                                                                     121

<210> SEQ ID NO 108
<211> LENGTH: 408
<212> TYPE: DNA
<213> ORGANISM: Brassica napus

<400> SEQUENCE: 108
```

```
agtttggttt aatgtgatta acaattgtgg tttaggtgta tggtccaacg aggttgatat    60 gggagcgaa aggagaggag caagaggcgg ggacgaagga gttcattgag atgctcaaga   120
tgctagagtc tgagcttgga gacaagactt actttggagg ygaaacattc ggttatgtgg   180
atatagctat gattggattc tactgctggt tcgacgtttt ggagaagtgt gggaatttta   240
gcatcgaagc agagtgtcca aagctgattg cttgggctaa aaggtgtatg aagagagaga   300
gtgtggctaa gtctcttcct gattcaaaca agatcactaa gttcgttcct gagctaaaga   360
aaaaaattgg catcgagtag ttctgttata atttaatctg tgttctgt               408
```

<210> SEQ ID NO 109
<211> LENGTH: 301
<212> TYPE: DNA
<213> ORGANISM: Brassica napus

<400> SEQUENCE: 109

```
tgaagcataa cctcaaacgc ctcagcaaca tcttcacagt aaagatagct acgaacatta    60
gtaccatctc tatgaatagg aagagctttc cctcttatca ccaacaaaaa taaacttagg   120
tccaacaaca gcatcttcat ctgtctcagc yatwaacctc atctgctctc acatgtataa   180
mcctcctgat ctatcctcta gtcactttac aagcctcgag aaggacatgc gttccgtaga   240
tattgttttt tagtgaactc gaaactgtta cggaaggagt tgtccacgtg agttctgtga   300
g                                                                   301
```

<210> SEQ ID NO 110
<211> LENGTH: 301
<212> TYPE: DNA
<213> ORGANISM: Brassica napus
<220> FEATURE:
<221> NAME/KEY: misc_feature
<222> LOCATION: (242)..(271)
<223> OTHER INFORMATION: where n is a, t, c, or g

<400> SEQUENCE: 110

```
acaaagctgt aattaaaaga taagacacga gtttcggttt ggttttgtgg ataaaaggat    60
aagaagagca ttttcccctt ttttatcgta attttttgttt tataaaagga taattatatt   120 aagtttatttt tgtttataca acgatcaatg kttttttgtaa ttctcattta tataacgatt   180
ctcacacctt tattgtttta gatggatatg ttgggtgaca actcacaagt agattttttc   240
annnnnnnnn nnnnnnnnnn nnnnnnnnnn ngctagttgg taaaaagaaa aagaaaagaa   300
g                                                                   301
```

<210> SEQ ID NO 111
<211> LENGTH: 1212
<212> TYPE: DNA
<213> ORGANISM: Brassica napus
<220> FEATURE:
<221> NAME/KEY: misc_feature
<222> LOCATION: (78)..(78)
<223> OTHER INFORMATION: where n is a, t, c, or g
<220> FEATURE:
<221> NAME/KEY: misc_feature
<222> LOCATION: (1113)..(1113)
<223> OTHER INFORMATION: where n is a, t, c, or g

<400> SEQUENCE: 111

```
cccgcgtccg ctgacggaca cggagatggc attgtgttac tggaaagctc tgttactact    60
actgctttca tgcctctntc agtgtttcgt atgctagtct cggcgatgcc gatccaaact   120
```

-continued

```
acagggcatg tgttggagaa tgcgagataa gcggctgcgt tggacaacta tgctttcctc      180
agtgcaactc ttcatccaac actggtccat ggtacacaca agagcctctg tacctacaat      240
ggcaaaagtg gggatgtcaa ggtgattgcc gttaccactg tatggttaac agagagaaag      300
aacgcgaaac tctcggtcaa cccccactca agtatcatgg taaatggcct ttcaagcgtc      360
tccttgggat tcaggagcct gcttctgttg ctttctctgt gctcaaccta gcgatgcatt      420
tccacggctg gatctccttc ttcattacgc tttactataa gctgcctctc agagaagata      480
agacggctta ctatgaatac gttggtctgt ggcatatcta cggtttcttg tcaatgaact      540
cttggttctg gagtgcggtt ttccacactc gggatgttga catcactgag aggttggact      600
actcgtctgc aatagcggtt atcggattct cactcattgt atccatcttg agaacgtttg      660
atgttcgggt agaggctgca agagtcatgg tatctgctcc agtgctagct tttgtcacca      720
ctcacatact gtatattaac ttctacaagc tcgactatgg ttggaacatg attgtgtgtg      780
tggccatggg agtcgctcag cttctcctat gggcaagatg ggctgctgtc tctagacatc      840
cttctaastg gaaactttgg atggtggtga tagcttcagg cttagctatg cttttggaga      900
tatatgactt tcctccatat gaaggctact tcgatgctca ctccatttgg catgctgcaa      960
ccattcctct aactgttctc tggtggagct ttattagaga cgatgctgag ttcagaactt     1020
ctagtcttct caagaaatct aagacaaagg ctaagtaagc ttatttgtct gacagatgca     1080
gaggtttctt gagtttttat ttccaatgtt ttntattcag agatttgtct tggccgtcct     1140
tacttttggt caattgagat ttgatattag tttctcattc atacacacgc ttatgctaat     1200 cttttttggac tc                                                        1212
```